United States Patent
Williams et al.

(10) Patent No.: US 12,396,997 B2
(45) Date of Patent: *Aug. 26, 2025

(54) METHODS OF TREATMENT WITH AN IBOGA ALKALOID

(71) Applicants: The Board of Trustees of the Leland Stanford Junior University, Stanford, CA (US); SONEIRA INC., P.B.C., Incline Village, NV (US)

(72) Inventors: Nolan R. Williams, Half Moon Bay, CA (US); John Philip Coetzee, San Francisco, CA (US); Andrew Dedinas Geoly, Stanford, CA (US); AnnaMarie Daniels, Denver, CO (US); Gregory Bird, Denver, CO (US)

(73) Assignees: The Board of Trustees of the Leland Stanford Junior University, Stanford, CA (US); SONEIRA INC., P.B.C., Incline Village, NV (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/817,153

(22) Filed: Aug. 27, 2024

(65) Prior Publication Data

US 2024/0415844 A1 Dec. 19, 2024

Related U.S. Application Data

(63) Continuation of application No. PCT/US2023/074200, filed on Sep. 14, 2023.

(60) Provisional application No. 63/375,679, filed on Sep. 14, 2022, provisional application No. 63/382,474, filed on Nov. 4, 2022, provisional application No. 63/448,116, filed on Feb. 24, 2023.

(51) Int. Cl.
| | |
|---|---|
| *A61K 31/55* | (2006.01) |
| *A61B 5/00* | (2006.01) |
| *A61K 9/00* | (2006.01) |
| *A61K 33/06* | (2006.01) |
| *A61K 45/06* | (2006.01) |
| *A61P 9/06* | (2006.01) |
| *A61P 25/00* | (2006.01) |
| *A61P 25/24* | (2006.01) |

(52) U.S. Cl.
CPC ............ *A61K 31/55* (2013.01); *A61B 5/4064* (2013.01); *A61K 9/0053* (2013.01); *A61K 33/06* (2013.01); *A61K 45/06* (2013.01); *A61P 9/06* (2018.01); *A61P 25/00* (2018.01); *A61P 25/24* (2018.01)

(58) Field of Classification Search
CPC . A61K 31/55; A61P 9/06; A61P 25/24; A61P 25/00
See application file for complete search history.

(56) References Cited

U.S. PATENT DOCUMENTS

| | | | |
|---|---|---|---|
| 2,813,873 A | 11/1957 | Janot et al. | |
| 2,877,229 A | 3/1959 | Taylor | |
| 4,499,096 A | 2/1985 | Lotsof | |
| 5,629,307 A | 5/1997 | Olney | |
| 5,925,634 A | 7/1999 | Olney | |
| 7,638,651 B2 | 12/2009 | Gant et al. | |
| 9,561,233 B2 | 2/2017 | Friedhoff | |
| 9,592,239 B2 | 3/2017 | Maillet | |
| 9,617,274 B1 | 4/2017 | Moriarty et al. | |
| 10,383,835 B2 | 8/2019 | Guedes et al. | |
| 10,421,710 B2 | 9/2019 | Gant et al. | |
| 10,426,786 B2 | 10/2019 | Rogawski et al. | |
| 11,554,106 B2 | 1/2023 | Petitjean et al. | |
| 11,651,491 B2 * | 5/2023 | Siemionow | G06T 7/0014 382/131 |
| 2005/0215571 A1 | 9/2005 | Romano | |
| 2005/0222270 A1 | 10/2005 | Olney et al. | |
| 2005/0288375 A1 | 12/2005 | Hobden et al. | |
| 2008/0280886 A1 | 11/2008 | Gant et al. | |
| 2012/0253037 A1 | 10/2012 | Moriarty et al. | |
| 2013/0165647 A1 | 6/2013 | Moriarty et al. | |
| 2013/0303756 A1 | 11/2013 | Mash et al. | |
| 2016/0220579 A1 | 8/2016 | Weis et al. | |
| 2016/0271271 A1 | 9/2016 | Molokanova et al. | |
| 2016/0331759 A1 | 11/2016 | Rand | |
| 2017/0072005 A1 | 3/2017 | Moskal | |
| 2019/0038646 A1 | 2/2019 | Bright et al. | |
| 2020/0000822 A1 | 1/2020 | Kruse et al. | |
| 2020/0165680 A1 | 5/2020 | Bahado-singh | |
| 2020/0230128 A1 | 7/2020 | Bosse et al. | |

(Continued)

FOREIGN PATENT DOCUMENTS

| | | |
|---|---|---|
| EP | 1903028 A1 | 3/2008 |
| WO | 2013040471 A2 | 3/2013 |

(Continued)

OTHER PUBLICATIONS

Goel et al., "Fish, Fish Oils and Cardioprotection: Promise or Fish Tale?", International Journal of Molecular Sciences, vol. 19, No. 12, pp. 3703/1-3703/13 (2018).*

(Continued)

*Primary Examiner* — Kevin E Weddington

(74) *Attorney, Agent, or Firm* — KPPB LLP

(57) ABSTRACT

Methods for treating a neuropsychiatric disorder by administering an *iboga* alkaloid and a cardioprotective agent in conjunction with analysis of brain image data is described. Also described are methods to improve brain health and to slow or reverse brain aging by disorder by administering an *iboga* alkaloid and a cardioprotective agent, where analysis of brain image data is used to monitor and/or evaluate treatment effectiveness.

13 Claims, 21 Drawing Sheets

(56) References Cited

U.S. PATENT DOCUMENTS

| | | | |
|---|---|---|---|
| 2020/0357119 | A1 | 11/2020 | Siemionow et al. |
| 2021/0322447 | A1 | 10/2021 | Plakogiannis et al. |
| 2022/0304980 | A1 | 9/2022 | Arnold et al. |
| 2023/0059204 | A1 | 2/2023 | Plakogiannis et al. |
| 2023/0100844 | A1 | 3/2023 | Rao et al. |
| 2024/0100061 | A1 | 3/2024 | Williams et al. |
| 2024/0100062 | A1 | 3/2024 | Williams et al. |
| 2024/0415845 | A1 | 12/2024 | Williams et al. |

FOREIGN PATENT DOCUMENTS

| | | | |
|---|---|---|---|
| WO | WO-2017184531 | A1 * | 10/2017 |
| WO | 2020181194 | A1 | 9/2020 |
| WO | 2022020352 | A1 | 1/2022 |
| WO | 2022261263 | A1 | 12/2022 |
| WO | 2024059713 | A2 | 3/2024 |
| WO | 2024059717 | A1 | 3/2024 |
| WO | 2024059713 | A3 | 4/2024 |

OTHER PUBLICATIONS

Hashiesh et al., "Pharmacological potential of JWH133, a cannabinoid type 2 receptor agonist in neurodegenerative, neurodevelopmental and neuropsychiatric diseases", European Journal of Pharmacology, vol. 909, pp. 174398 (2021).*
Cherian et al., "Magnesium-ibogaine therapy in veterans with traumatic brain injuries", Nature Medicine, vol. 30, Jan. 5, 2024, pp. 373-381.
Hart, Jr. et al., "Neuroimaging of Cognitive Dysfunction and Depression in Aging Retired National Football League Players", JAMA Neurol., (2013) 70(3):326.
Jordan et al., "Apolipoprotein E ∈4 Associated With Chronic Traumatic Brain Injury in Boxing", JAMA. 1997;278(2):136-140.
Kutner et al., "Lower Cognitive Performance of Older Football Players Possessing Apolipoprotein E ε4", Neurosurgery, (2000) 47(3):651.
Mckee et al., "The first NINDS/NIBIB consensus meeting to define neuropathological criteria for the diagnosis of chronic traumatic encephalopathy", Acta Neuropathol., (2016) 131(1):75-86.
International Search Report and Written Opinion for International Application No. PCT/US2023/074195, Search completed Nov. 24, 2023, Mailed Feb. 15, 2024, 13 Pgs.
International Search Report and Written Opinion for International Application No. PCT/US2023/074200, Search completed Nov. 25, 2023, Mailed Jan. 26, 2024, 11 Pgs.
Third-Party Submission Under 37 CFR 1.290 for U.S. Appl. No. 18/467,324, filed Jul. 10, 2024, 54 pgs.
"Clinical Guidelines for Ibogaine-assisted Detoxification", The Global Ibogaine Alliance, Feb. 25, 2016, https://ibogaineguidelines.com/, 5 pgs.
"Lactated Ringers-sodium chloride, sodium lactate, potassium chloride, and calcium chloride injection, Solution", B. Braun Medical Inc. Aug. 2022, 18 pages, Dailymed.
"Magnesium Sulfate—Magnesium Sulfate Heptahydrate Injection, Solution", Fresenius Kabi USA LLC, Feb. 2021, 5 pages, Dailymed.
"Pre-post Evaluation of the Safety and Efficacy of Ibogaine-Magnesium Therapy in Veterans With Repeated Blast Exposure", ClinicalTrials.gov ID NCT04313712, accessed from: https://clinicaltrials.gov/study/NCT04313712?term=ibogaine&rank=4&a=1&tab=history, Last updated: Aug. 9, 2023, Version 3: Mar. 22, 2022, 6pgs.
"Pre-post Evaluation of the Safety and Efficacy of Ibogaine-Magnesium Therapy in Veterans With Repeated Blast Exposure", ClinicalTrials.gov ID NCT04313712, accessed from: https://clinicaltrials.gov/study/NCT04313712?term=ibogaine&rank=4&a=1&tab=history, Last updated: Aug. 9, 2023, Version 2: Oct. 19, 2021, 6 pages.
"Pre-post Evaluation of the Safety and Efficacy of Ibogaine-Magnesium Therapy in Veterans With Repeated Blast Exposure", ClinicalTrials.gov, ID NCT04313712, accessed from: https://clinicaltrials.gov/study/NCT04313712?term=ibogaine&rank=4&a=1&tab=history, Last updated: Aug. 9, 2023, Version 1: Mar. 16, 2020, 6 pages.
"Safety of Ibogaine (Part2)", YouTube, ICEERS, Presentation by Jeffrey D. Kamlet M.D., Apr. 9, 2011, Retrieved from: https://www.youtube.com/watch?v=Nd7ljxttGZ8&ab_channel=ICEERS.
Alexander, "Pharmacotherapy for Post-traumatic Stress Disorder In Combat Veterans Focus on Antidepressants and Atypical Antipsychotic Agents", Pharm. Ther., 2012, 37, 32-38.
Alper, "Ibogaine: A Review", The Alkaloids, (2001), vol. 56, Chapter 1, pp. 1-38.
Barsuglia et al., "Chapter 5—A case report SPECT study and theoretical rationale for the sequential administration of ibogaine and 5-MeO-DMT in the treatment of alcohol use disorder", Prog. Brain. Res., 2018, 424:121-158.
Bastos-Leite et al., "Cerebral Blood Flow by Using Pulsed Arterial Spin-Labeling in Elderly Subjects with White Matter Hyperintensities", Am. J. Neuroradiol, 2008,29(7):1296-1301.
Beidel et al., "Trauma Management Therapy and Prolonged Exposure Therapy for PTSD in an active duty sample: Design and methodology of a randomized clinical trial", Contemp. Clin. Trials Commun., 2020, 17, 100491.
Benjamini et al., "Controlling the false discovery rate: a practical and powerful approach to multiple testing", J. R. Stat. Soc. Ser. B Methodol., 1995, 57, 289-300.
Bruss et al., "Hamilton Anxiety Rating Scale Interview guide: joint interview and test-retest methods for interrater reliability", Psychiatry Res., 1994, 53, 191-202.
Bryan et al., "Moral injury, posttraumatic stress disorder, and suicidal behavior among National Guard personnel.", Psychol. Trauma Theory Res. Pract. Policy, 2018, 10, 36-45.
Cameron et al., "A non-hallucinogenic psychedelic analogue with therapeutic potential", Nature, 2021, 589, 474-479.
Cole et al., "Predicting Age Using Neuroimaging: Innovative Brain Ageing Biomarkers", Trends in Neurosciences, 2017, 40(12):681.
Cole et al., "Predicting brain age with deep learning from raw imaging data results in a reliable and heritable biomarker", NeuroImage, 2017, 163:115-124.
Cole et al., "Prediction of Brain Age Suggests Accelerated Atrophy after Traumatic Brain Injury", Annals of Neurology, 2015, 77(4):571.
Corkery, "Chapter 8—Ibogaine as a treatment for substance misuse: Potential benefits and practical dangers", Progress in Brain Research, 2018, 242:217-257.
Crofts et al., "Imaging functional recovery following ischemic stroke: clinical and preclinical fMRI studies", J. Neuroimaging, 2020, 30:5-14.
Davis et al., "Open-label study of consecutive ibogaine and 5-MeO-DMT assisted-therapy for trauma-exposed male Special Operations Forces Veterans: prospective data from a clinical program in Mexico", The American Journal of Drug and Alcohol Abuse, pp. 1-10, published online on Sep. 21, 2023, accessed from: https://doi.org/10.1080/00952990.2023.2220874, (2023).
De Haan et al., "Quality of life after stroke: impact of stroke type and lesion location", Stroke, 1995, 26(3):402-408.
Dickinson et al., "Clinical Guidelines for Ibogaine-Assisted Detoxification", Ibogaine Safety Guidlelines, 1st Edition, Ver 1.1 (Feb. 25, 2016), 4 pgs, accessed from: https://ibogaineguidelines.com/clinical-guidelines, and section "12. Treatment" 6 pages, accessed from: https://ibogaineguidelines.com/clinical-guidelines/treatment/ (2015).
Dickinson et al., "Clinical Guidelines for Ibogaine-Assisted Detoxification", The Global Ibogaine Therapy Alliance, 1st Edition, Version 1.1, Originally Published: Sep. 2015, Current Version: Feb. 25, 2016, 62 pgs.
Dimyan et al., "Neuroplasticity in the context of motor rehabilitation after stroke", Nat. Rev. Neurol., 2011, 7:76-85.
Dukart et al., "JuSpace: A tool for spatial correlation analyses of magnetic resonance imaging data with nuclear imaging derived neurotransmitter maps", J et al., Hum. Brain Mapp., 2021, 42:555-556.
Franke et al., "Ten Years of BrainAGE as a Neuroimaging Biomarker of Brain Aging: What Insights Have We Gained?", Frontiers in Neurology, 2019, 10(789):1-26.

(56) References Cited

OTHER PUBLICATIONS

Gold, "DSM-5 and the assessment of functioning: the World Health Organization Disability Assessment Schedule 2.0 (WHODAS 2.0)", J. Am. Acad. Psychiatry Law, 2014,42,9.

Han et al., "Brain Age Prediction: A Comparison between Machine Learning Models Using Brain Morphometric Data", Sensors, 2022, 22:8077.

Hoshino et al., "Studies of Magnesium in Congenital Long QT Syndrome", Pediatr. Cardiol. May 1, 2014:23(1):41-48. doi: 10.1007/s00246-001-0011-5.

Huffman et al., "A formal synthesis of (.+-.)-ibogamine", J. Org. Chem, 1985, 50, 1460-1464.

Inoue et al., "Veteran and Military Mental Health Issues", StatPearls (StatPearls Publishing, 2022).

Kamlet, "Ibogaine", http://www.slideserve.com/nailah/ibogaine, Presentation Nov. 2009.

Kelly-Hayes et al., "The influence of gender and age on disability following ischemic stroke: the Framingham study", J. Stroke Cerebrovasc Dis., 2003, 12(3):119-126.

Knuijver et al., "Safety of Ibogaine Administration in Detoxification of Opioid-Dependent Individuals: A Descriptive Open-Label Observational Study", Addiction, Aug. 9, 2021, vol. 117(1), 11 pages, DOI: 10.1111/add.15448.

Koenig et al., "The Moral Injury Symptom Scale-Military Version", J. Relig Health, (2018) 57:249-265.

Leucht et al., "What does the MADRS mean? Equipercentile linking with the CGI using a company database of mirtazapine studies", J. Affect. Disord., 2017,210, 287-293.

Maas et al., "Traumatic brain injury: progress and challenges in prevention, clinical care, and research", Lancet Neurol.2022, 21, 1004-1060.

Marton et al., "Ibogaine Administration Modifies GDNF and BDNF Expression in Brain Regions Involved in Mesocorticolimbic and Nigral Dopaminergic Circuits", Front. Pharmacol., 2019, 10.

Mash, "A Study of Oral Ibogaine in Opioid Withdrawal", Clinical Trials, Aug. 2, 2022.

Mash et al., "Ibogaine Detoxification Transitions Opioid and Cocaine Abusers Between Dependence and Abstinence: Clinical Observations and Treatment Outcomes", Frontiers in Pharmacology, Jun. 2018, vol. 9, Article 529.

Matza et al., "Identifying HAM-A cutoffs for mild, moderate, and severe generalized anxiety disorderm", Int. J. Methods Psychiatr. Res., 2010, 19, 223-232.

McIntyre et al., "Quetiapine Adjunct to Selective Serotonin Reuptake Inhibitors or Venlafaxine In Patients With Major Depression, Comorbid Anxiety, And Residual Depressive Symptoms: A Randomized, Placebo-Controlled Pilot Study", Depress. Anxiety, 2007, 24, 487-494.

Mitchell et al., "MDMA-assisted therapy for severe PTSD: a randomized, double-blind, placebo-controlled phase 3 study", Nature Medicine, (2021) vol. 27, pp. 1025-1033.

Mitra et al., "Lag threads organize the brain's intrinsic activity", PNAS, 2015, E2235-E2244.

Montgomery et al., "A new depression scale designed to be sensitive to change", Br J Psychiatry, Apr. 1979; 134:382-9. doi: 10.1192/bjp.134.4.382.

Morissette et al., "Deployment-related TBI, persistent postconcussive symptoms, PTSD, and depression in OEF/OIF veterans.", Rehabil Psychol., 2011, 56(4):240-350.

Muller et al., "Differentiating moderate and severe depression using the Montgomery-Åsberg depression rating scale (MADRS)", J. Affect. Disord., 2003, 77, 255-260.

Ona et al., "The adverse events of ibogaine in humans: an updated systematic review of the literature (2015-2020)", Psychopharmacology, 1977-1987 (2022), 239.

Polusny et al., "Longitudinal Effects of Mild Traumatic Brain Injury and Posttraumatic Stress Disorder Comorbidity on Postdeployment Outcomes in National Guard Soldiers Deployed to Iraq", Arch Gen Psychiatry, 2011, 68(1):79-89.

Rimel et al., "Disability Caused by Minor Head Injury", Neurosurgery, 1981, 9(3):221-229.

Ruud et al., "How toxic is ibogaine?", Clin. Toxicol., 2016, 54, 297-302.

Schneiderman et al., "Understanding Sequelae of Injury Mechanisms and Mild Traumatic Brain Injury Incurred during the Conflicts in Iraq and Afghanistan: Persistent Postconcussive Symptoms and Posttraumatic Stress Disorder", Am J. Epidemiol, 2008, 167:144601452.

Shear et al., "Reliability and validity of a structured interview guide for the Hamilton Anxiety Rating Scale (SIGH-A)", Depress. Anxiety, 2001, 13, 166-178.

Steenkamp et al., "First-line Psychotherapies for Military-Related PTSD", JAMA, 2020, 323, 656-657.

Steenkamp et al., "Psychotherapy for Military-Related PTSD A Review of Randomized Clinical Trials", JAMA2015, 314, 489-500.

Su et al., "Enhancing brain plasticity to promote stroke recovery", Front Neurol., 2020, 11:554089.

Ustun et al., "Measuring health and disability: Manual for WHO disability assessment schedule WHODAS 2.0", World Health Organization, 2010.

Vanderploeg et al., "Long-term morbidities following self-reported mild traumatic brain injury", J. Clinical and Experimental Neuropsychology, 2007, 29(6):585-598.

Wasko et al., "DARK Classics in Chemical Neuroscience: Ibogaine", ACS Chem. Neurosci., 2018, 9, 2475-2483.

Weathers et al., "The Clinician-Administered PTSD Scale for DSM-5 (CAPS-5): Development and initial psychometric evaluation in military veterans.", Psychol. Assess. 2018, 30, 383-395.

Wisco et al., "Posttraumatic stress disorder in the US veteran population: Results from the National Health and Resilience in Veterans Study", J. Clinical Psychiatry, 2014, 75(12):1338-1346.

International Preliminary Report on Patentability for International Application PCT/US2023/074195, Report issued Mar. 1, 2025, Mailed Mar. 27, 2025, 10 pgs.

International Preliminary Report on Patentability for International Application PCT/US2023/074200, Report issued Mar. 1, 2025, Mailed Mar. 27, 2025, 6 pgs.

Caron et al., "Effects of Intravenous Magnesium Sulfate on the QT Interval in Patients Receiving Ibutilide", Pharmacotherapy, vol. 23, No. 3, Mar. 2003, pp. 296-300, doi: 10.1592/phco.23.3.296.32109.

Dicarlo et al., "Effects of Magnesium Sulfate on Cardiac Conduction and Refractories in Humans", Journal of the American College of Cardiology, vol. 7, No. 6, Jun. 1986, pp. 1356-1362, doi: 10.1016/s0735-1097(86)80157-7.

Farkas, "A Better Approach to Torsade de Pointes", PulmCrit (EMCrit), electronic article, date published Jul. 2, 2018, URL:https://emcrit.org/pulmcrit/tdp-magnesium/, 11 pgs.

Foster et al., "Ibutilide: A Review of its Pharmacological Properties and Clinical Potential in the Acute Management of Atrial Flutter and Fibrillation".

Drugs, vol. 54, No. 2, Aug. 1997, pp. 312-330, doi: 10.2165/00003495-199754020-00010.

Galgano et al., "Traumatic Brain Injury: Current Treatment Strategies and Future Endeavors", Cell Transplantation, vol. 26, No. 7, Jul. 30, 2017, pp. 1118-1130, doi: 10.1177/0963689717714102.

Goutarel et al., "Pharmacodynamics and Therapeutic Applications of Iboga and Ibogaine", Psychedelic Monographs and Essays, vol. 6, 1993, Accessed from The Ibogaine Dossier, Obtained from: https://ibogainedossier.com/bwiti1.html, pp. 70-111.

Grissinger, "Avoiding Patient Harm from a Magnesium Bolus Dose", P&T: a peer-reviewed journal for formulary management, vol. 39, No. 2, Feb. 2014, pp. 81 and 129.

Ikonomidou et al., "Why did NMDA receptor antagonists fail clinical trials for stroke and traumatic brain injury?", The Lancet Neurology, vol. 1, No. 6, Oct. 2002, pp. 383-386, doi: 10.1016/s1474-4422(02)00164-3.

Irimia et al., "Comparison of Acute and Chronic Traumatic Brain Injury Using Semi-Automatic Multimodal Segmentation of MR Volumes", Journal of Neurotrauma, vol. 28, No. 11, Nov. 2011, pp. 2287-2306, doi: 10.1089/neu.2011.1920.

Noordam et al., "Effects of Calcium, Magnesium and Potassium Concentrations on Ventricular Repolarization in Unselected Indi-

(56) References Cited

OTHER PUBLICATIONS viduals", Journal of the American College of Cardiology, vol. 73, No. 24, Jun. 25, 2019, pp. 3118-3131, doi: 10.1016/j.jacc.2019.03.519.

Satoh et al., "Effects of Magnesium Sulfate on the Haloperidol-Induced QT Prolongation Assessed in Canine In Vivo Model Under the Monitoring of Monophasic Action Potential", Japanese circulation journal, vol. 64, No. 6, Jun. 2000, pp. 445-451, doi: 10.1253/jcj.64.445.

Sillans, "Otto Gollnhofer 1934-1994", Journal des Africanistes, vol. 65, No. 2, 1995, Obtained from: https://www.persee.fr/doc/jafr_0399-0346_1995_num_65_2_2638, pp. 251-255. (French Language Only).

Corrigan et al., "Traumatic Brain Injury as a Chronic Health Condition", Archives of Physical Medicine and Rehabilitation, vol. 94, 2013, pp. 1199-1201.

Haarbauer-Krupa et al., "Epidemiology of Chronic Effects of Traumatic Brain Injury", Journal of Neurotrauma, vol. 38, Dec. 1, 2021, pp. 3235-3247.

Manley et al., "A new characterisation of acute traumatic brain injury: the NIH-NINDS TBI Classification and Nomenclature Initiative", The Lancet Neurology, vol. 24, 2025, pp. 512-523.

Masel et al., "Traumatic Brain Injury: A Disease Process, Not an Event", Journal of Neurotrauma, vol. 27, pp. 1529-1540, Aug. 2010.

* cited by examiner

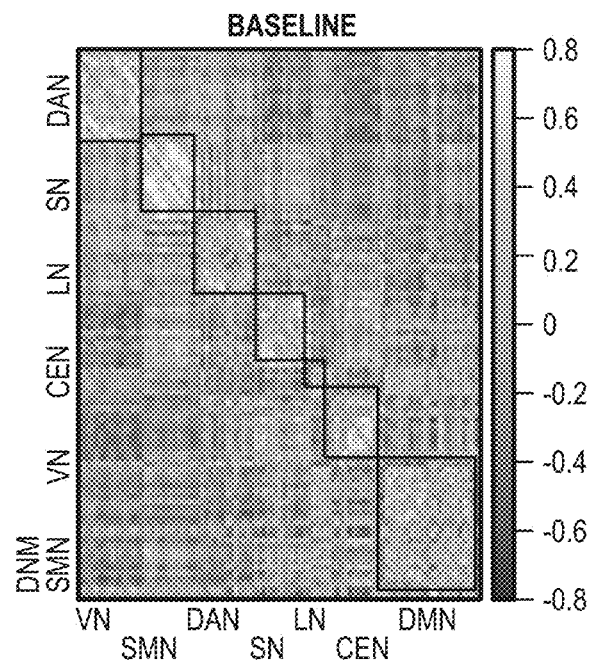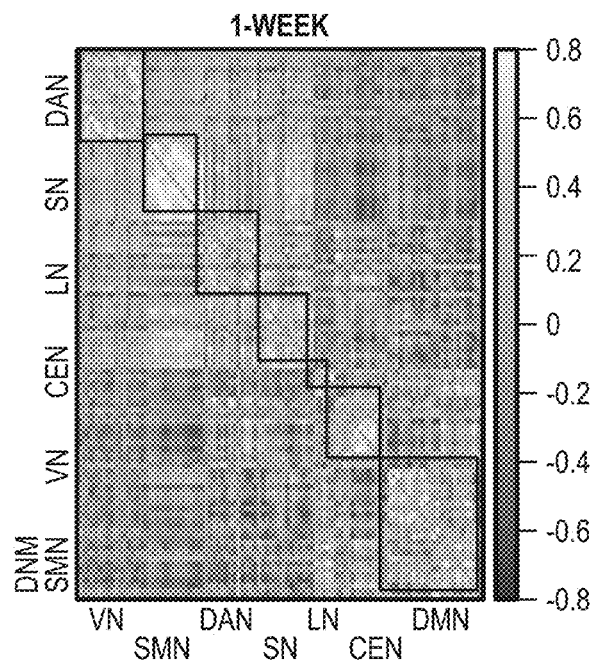
FIG. 1A          FIG. 1B
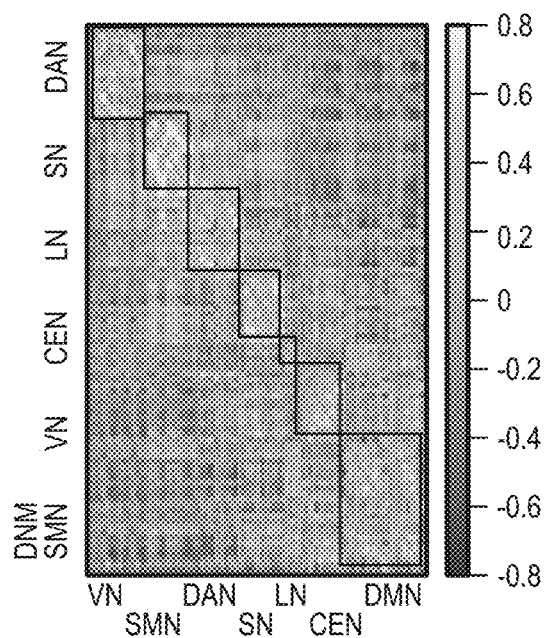
FIG. 1C

Mean Baseline Volume & 1-Month Post Volume (mm³)

Absolute Improvement in Disability Symptoms

Absolute Improvement in Depression Symptoms

METHODS OF TREATMENT WITH AN IBOGA ALKALOID

CROSS-REFERENCE TO RELATED APPLICATIONS

This application is a continuation of International Application No. PCT/US2023/074200, filed Sep. 14, 2023, which claims the benefit of U.S. Provisional Application No. 63/375,679, filed Sep. 14, 2022, U.S. Provisional Application No. 63/382,474, filed Nov. 4, 2022, and U.S. Provisional Application No. 63/448,116, filed Feb. 24, 2023, each of which is incorporated herein by reference in its entirety.

TECHNICAL FIELD

The subject matter described herein relates to methods for treating a neuropsychiatric condition, for slowing brain aging and/or for improving brain health, with an *iboga* alkaloid compound in conjunction with analysis of brain image data.

BACKGROUND

Neuropsychiatric disorders encompass brain diseases or dysfunctions that cause a psychiatric symptom. Neuropsychiatric disorders include depression, schizophrenia, post-traumatic stress disorder, and anxiety disorders. They also include neurodegenerative diseases such as Alzheimer's disease, Parkinson's disease, Huntington's disease ataxia, Lewy body disease and others. Many of these neuropsychiatric disorders have few treatment options and there remains a need for treating the disorders and their symptoms.

Aging in an organism is accompanied by an accumulation of changes over time. As human lifespan increases, a greater fraction of the population suffers from aging-associated cognitive impairments, making it crucial to elucidate means by which to maintain cognitive integrity by slowing and/or reversing brain aging, in healthy subjects and in subjects with a neuropsychiatric disorder.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In an embodiment, a method for treating a neuropsychiatric condition in a subject is provided. The method comprises administering, or instructing to administer, to a subject a cardioprotective agent in an amount effective to achieve a physiologic effect to reduce risk of long QT syndrome and an *iboga* alkaloid or salt thereof; and monitoring the subject by analyzing image data from a brain image. In an embodiment, the image data is analyzed with a model to determine a predicted brain age.

In one embodiment, the method further comprises continuing to administer, or the instructing to administer, or recommending an alternative to the administering or instructing to administer, based on the monitoring of the subject and/or based on the analyzing image data.

In one embodiment, the subject has a chronological age, and the method further comprising comparing the predicted brain age to the chronological age.

In one embodiment, the method further comprises repeating the administering or instructing to administer if the predicted brain age is greater than the chronological age. In one embodiment, the repeating the administering or instructing to administer is with the same *iboga* alkaloid and/or the same cardioprotective agent as the prior administering or instructing to administer. In an embodiment, the repeating the administering or instructing to administer is at the same dose and/or the same route of administration and/or with the same *iboga* alkaloid and/or the same cardioprotective agent as the prior administering or instructing to administer. In an embodiment, the repeating the administering or instructing to administer is at a different dose and/or a different route of administration and/or with a different *iboga* alkaloid (or other drug) and/or a different cardioprotective agent as the prior administering or instructing to administer.

In one embodiment, the repeating of the monitoring determines a post-treatment predicted brain age, and the post-treatment predicted brain age is compared to the chronological age.

In one embodiment, the method comprises repeating of the administering or instructing to administer if the post-treatment predicted brain age is greater than the chronological age.

In one embodiment, the method comprises repeating the administering or instructing to administer if the post-treatment predicted brain age is equal to or less than the precited brain age.

In one embodiment, the method comprises recommending an alternative to the administering or instructing to administer if the post-treatment predicted brain age is equal to or greater than the predicted brain age.

In one embodiment, the predicted brain age is a prior determined predicted brain age of the subject, where the prior determined predicted brain agent may be prior to treatment with an *iboga* alkaloid or may be after treatment with one or more doses of an *iboga* alkaloid.

In one embodiment, monitoring comprises analyzing image data from a brain image using an algorithm or brain age prediction model.

In one embodiment, the method further comprises prior to the administering, or instructing to administer, analyzing image data from a brain image using an algorithm (or brain age prediction model) to determine a pre-treatment predicted brain age.

In an embodiment, a treatment method is provided that is comprised of obtaining image data from an image of a subject's brain, the subject having a chronological age, analyzing the image data to determine a predicted brain age, and administering, or instructing to administer, an *iboga* alkaloid or salt thereof and a cardioprotective agent in an amount effective to achieve a physiologic effect to reduce risk of long QT syndrome based on the analyzing.

In an embodiment, a method of improving brain health is provided. The method comprises obtaining image data from an image of a subject's brain, the subject having a chronological age and analyzing the image data to determine a predicted brain age. In one embodiment, if the predicted brain age is greater than the chronological age, administering, or instructing to administer, an *iboga* alkaloid or salt thereof and a cardioprotective agent in an amount effective to achieve a physiologic effect to reduce risk of long QT syndrome.

In one embodiment, analyzing comprises applying an algorithm or brain prediction model to the image data.

In one embodiment, analyzing reveals the predicted brain age is greater than the chronological age of the subject, and said administering or instructing to administer is performed based thereon.

In one embodiment, obtaining image data comprises obtaining the image of the subject's brain.

In one embodiment, the method further comprises repeating the steps of obtaining and/or analyzing.

In one embodiment, if the predicted brain age is (i) greater than the subject's chronological age or (ii) equal to or greater than a previously determined predicted brain age for the subject, recommending a treatment protocol selected from
  (a) repeating said administering or instructing to administer,
  (b) waiting a period of time and repeating said monitoring,
  (c) no further treatment with the *iboga* alkaloid, and
  (d) administering a therapy other than an *iboga* alkaloid.

In one embodiment, if the predicted brain age is (i) equal to or less than the subject's chronological age or (ii) less than a previously determined predicted brain age for the subject, recommending a treatment protocol selected from
  (a) repeating said administering or instructing to administer,
  (b) waiting a period of time and repeating said monitoring,
  (c) no further treatment with the *iboga* alkaloid, and
  (d) administering a therapy other than an *iboga* alkaloid.

In one embodiment, the step of repeating the administering or instructing to administer comprises repeating the administering or instructing to administer at a dose or route different from a prior administering or instructing to administer.

In one embodiment, the step of repeating the administering or instructing to administer comprises repeating the administering or instructing to administer the *iboga* alkaloid or salt thereof and/or the cardioprotective agent in a formulation different from that in a prior administering or instructing to administer.

In an embodiment, a method for treating a neuropsychiatric condition in a subject is provided. The method comprises analyzing a first image data of a subject's brain using a brain age model to determine a first estimated brain age of the brain, where the first image data is captured prior to administration of an *iboga* alkaloid or salt thereof: administering, or instructing to administer, to the subject a cardioprotective agent in an amount effective to achieve a physiologic effect to reduce risk of long QT syndrome and the *iboga* alkaloid or salt thereof: analyzing a second image data of the subject's brain using the brain age model to determine a second estimated brain age of the brain, where the second image data is captured after administration of the *iboga* alkaloid or salt thereof; and evaluating or verifying treatment efficacy based on the first and second estimate brain ages. In an embodiment, when the first estimated brain age is greater than the second estimated brain age treatment efficacy is verified.

In one embodiment, verifying treatment efficacy comprises verifying a previously administered dose of *iboga* alkaloid or salt thereof is a correct dosage amount for the subject. In one embodiment, verifying treatment efficacy comprises verifying a previously administered dose of *iboga* alkaloid or salt thereof is an incorrect dosage amount for the subject. In one embodiment, the method further comprises recommending an adjustment in the dosage amount, the route of administration, the drug administered, or the pharmaceutical formulation.

In one embodiment, the method further comprises administering, or instructing to administer, to the subject an additional dose of the cardioprotective agent in an amount effective to achieve a physiologic effect to reduce risk of long QT syndrome and the *iboga* alkaloid or salt thereof.

In one embodiment, the brain age model, also referred to herein as an algorithm, is a linear model or non-linear model. In one embodiment, the brain age model is a parametric model, a non-parametric model, or an ensemble learning model. In one embodiment, the brain age model is the brain age prediction model BrainAGE (Franke, K. et al., Frontiers in Neurology. 10 (789): 1-26 (2019)).

In one embodiment, the image data is obtained from an image obtain using magnetic resonance imaging (MRI), an image from a computerized tomography (CT) scan, an image from a positron emission tomography (PET) scan, or an image from a single-positron emission computerized tomography (SPECT) scan.

In one embodiment, the MRI is a T1-weighted MRI image or a diffusion-weighted MRI (DWI). In one embodiment, the T1-weighted MRI image data is raw T1-weighted structural MRI image data. In one embodiment, the DWI is diffusion tensor imaging (DTI).

In one embodiment, the image data is processed using voxel-based morphometry. In one embodiment, the voxel-based morphometry is applied to a brain tissue selected from gray matter and white matter.

In one embodiment, the image data is analyzed to obtain a measure of one or more of total intracranial volume, cortical thickness, surface area and subcortical volume.

In one embodiment, the algorithm, also referred to herein as a model, is a linear algorithm or non-linear algorithm. In one embodiment, the algorithm is a parametric algorithm, a non-parametric algorithm, or an ensemble learning algorithm. In one embodiment, the algorithm is the brain age prediction model BrainAGE (Franke, K. et al., Frontiers in Neurology, 10 (789): 1-26 (2019)).

In one embodiment, the subject is a healthy individual. In one embodiment, the subject has a known risk of cognitive decline or is at risk of a cognitive decline due to a neuropsychiatric condition. In one embodiment, the subject is at risk of a cognitive decline due to a genetic disorder. In one embodiment, the genetic disorder is presence of a gene variant or presence of a gene mutation. In one embodiment, the subject the genetic disorder is presence of a gene variant selected from apolipoprotein E-4 (ApoE4) gene, amyloid precursor protein (APP), presenilin 1 (PSEN1) and presenilin 2 (PSEN2). In one embodiment, the subject the genetic disorder is a mutation selected from a leucine rich repeat kinase 2 (LRRK2) mutation, a tau gene mutation, and a glucocerebrosidase (GBA) gene mutation.

In one embodiment, the subject is at risk of a cognitive decline due to a family history of cognitive decline or substance abuse disorder. In one embodiment, the subject the substance abuse disorder is alcohol abuse. In one embodiment, the subject the subject is diagnosed with mild cognitive impairment.

In one embodiment, the subject has a traumatic brain injury or has a history of one or more traumatic brain injuries. In one embodiment, the subject the subject has a post-traumatic stress disorder.

In one embodiment, the *iboga* alkaloid or salt thereof is ibogaine or an analog of ibogaine.

In one embodiment, the *iboga* alkaloid or salt thereof is ibogaine hydrochloride. In one embodiment, the subject the *iboga* alkaloid or salt thereof is administered orally, parenterally or intrathecally.

In one embodiment, the cardioprotective agent is selected from the group consisting of a mineral, a sodium channel blocker (a class 1B antiarrhythmic), a potassium channel blocker, an hERG (human ether-a-go-go-related gene) channel agonist, and beta adrenoceptor agonists.

In one embodiment, the sodium channel blocker is selected from the group consisting of mexiletine, tocainide, lidocaine, flecainide, and R-56865 (2-benzothiazolamine, N-(1-(4-(4-fluorophenoxy)butyl)-4-piperidinyl)-N-methyl).

In one embodiment, the subject the potassium channel blocker is selected from the group consisting of amiodarone and ranolazine.

In one embodiment, the mineral is selected from the group consisting of magnesium, calcium and potassium.

In one embodiment, the mineral is in the form a salt, and wherein said administering or instructing to administer the cardioprotective agent comprises administering or instructing to administer concurrent with and/or subsequent to the administering the *iboga* alkaloid or salt thereof.

In one embodiment, the cardioprotective agent is administered in an amount effective to achieve a physiologic effect to reduce risk of a drug-induced or acquired long QT syndrome.

In one embodiment, the cardioprotective agent is an electrolyte. In one embodiment, the subject the electrolyte is magnesium, potassium or calcium. In one embodiment, the subject the electrolyte is a salt form of the electrolyte. In one embodiment, the electrolyte is a salt form of magnesium selected from the group consisting of magnesium aspartate, magnesium aspartate hydrochloride, magnesium bisglycenate, magnesium carbonate, magnesium chloride, magnesium citrate, magnesium gluconate, magnesium glycinate, magnesium hydroxide, magnesium malate, magnesium oxide, magnesium sulfate, and magnesium taurate.

In one embodiment, the cardioprotective agent is a magnesium salt, and wherein said magnesium salt is administered in an amount of between about 50-8000 mg per day.

In one embodiment, the *iboga* alkaloid or salt thereof is a salt of ibogaine and wherein said administering the salt of ibogaine comprises administering between about 200-2500 mg.

In one embodiment, the predicted brain age is greater than the chronological age by 3 years or more. In one embodiment, the predicted brain age is greater than the chronological age by 1 year or more, 2 years or more, 4 years or more, 5 years or more, 6 years or more, 7 years or more, 8 years or more, 9 years or more or 10 years or more. In an embodiment, the predicted brain age is greater than the chronological age by between about 1-10 years, 1-8 years, 1-6 years, 1-5 years, 1-4 years, 1-3 years, 1-2 years, 2-10 years, 2-8 years, 2-6 years, 2-5 years, 2-4 years, or 2-3 years.

In one embodiment, the cardioprotective agent is an electrolyte.

In one embodiment, the electrolyte is magnesium, potassium or calcium.

In one embodiment, the electrolyte is a salt form of the electrolyte.

In one embodiment, the electrolyte is a salt form of magnesium selected from the group consisting of magnesium aspartate, magnesium aspartate hydrochloride, magnesium bisglycenate, magnesium carbonate, magnesium chloride, magnesium citrate, magnesium gluconate, magnesium glycinate, magnesium hydroxide, magnesium malate, magnesium oxide, magnesium sulfate, and magnesium taurate.

In one embodiment, the cardioprotective agent is a magnesium salt for administration to the subject of at a dose of between about 50-8000 mg.

Treatments described herein utilize ibogaine and/or other biosimilar *iboga* alkaloids to treat conditions not previously understood to be safely treatable using these drugs. Also, as described infra, the dangerous cardiovascular side effects can be avoided by co-treatment using magnesium ions, calcium ions, and/or potassium ions. Dosing of patients using one or a combination of these ions can stabilize hERG potassium channels and prevent torsades de pointes. In many embodiments, prior to treatment using ibogaine or a similar *iboga* alkaloid, electrolyte levels in the patient are stabilized. Subsequently, the patient is dosed with the positive ions along with the delivery of ibogaine (or similar *iboga* alkaloid) which mitigates and/or prevents the deleterious cardiovascular side effects. This co-administration of compounds enables a significantly safer administration of ibogaine, enabling patients to benefit from the treatment effects discussed below.

In an embodiment, ibogaine's cardiotoxicity can be sufficiently negated by delivering ibogaine (or a cardiotoxic ibogaine analog or any salt thereof) in combination with any of: lidocaine, mexiletine, R-56865, flecanide, amiodarone, and ranolazine. In particular, mexiletine is well tolerated and considered safe for oral use. In an embodiment, a combination pill having a ratio of 4 mg mexiletine to 18 mg ibogaine is provided. However, in practice these ratios may be shifted from anywhere between 2-6 mg mexiletine to 15-20 mg ibogaine. Further, the total mass per dose can be increased in order to comfortably dose patients at a ratio of approximately 4 mg/kg mexiletine to 15-20 mg/kg ibogaine. In an embodiment, the resulting combination drug of mexiletine/ibogaine can be administered orally for convenience, and further to ensure that no raw ibogaine is packaged and sent to the public facing medical system. The combination drug can be used to treat addiction as well as any number of different brain conditions such as, but not limited to post-traumatic stress disorder, traumatic brain injury, depression, insomnia, Parkinson's disease, chronic traumatic encephalopathy, and/or any other condition for which ibogaine provides therapeutic effect. In an embodiment, a pharmaceutical composition comprising mexiletine or a salt thereof and ibogaine or a salt thereof, in the ratio of 2-6 mg mexiletine to 15-20 mg ibogaine is provided. In another embodiment, the composition is prepared to be orally administered. In another embodiment, a pharmaceutical composition comprising ibogaine or a salt thereof, in combination with any of: lidocaine, mexiletine, R-56865, flecanide, amiodarone, ranolazine, or any salt thereof is provided.

Provided are methods and compositions where an *iboga* alkaloid, such as ibogaine, in order to repair brain tissue which can be used to treat neurodegenerative diseases and to reverse or slow brain aging. Furthermore, empirical verification that brain age can be reversed via ibogaine treatment is provided. In embodiments, an magnetic resonance imaging (MRI) scan is conducted prior to treatment and/or after treatment, such as 1-7 days post treatment or 1-month post treatment, in order to confirm regrowth and therefore efficacy of the treatment. Brain age algorithms can be used as empirical verification of treatment.

In an aspect, a treatment of a neurodegenerative disease is provided. The treatment comprises stabilizing a patient's electrolyte level, administering to the patient a therapeutically effective amount of ibogaine, ibogaine derivative, or a pharmaceutically acceptable salt and/or solvate thereof; and co-administering a human ether-a-go-go related gene (hERG) stabilizing amount of magnesium ion, calcium ion, or potassium ion. Before or after the administering brain image data of the patient is analyzed to determine a predicted brain age. The predicted brain age is compared with the patient's chronological age, and difference in the two is used to guide treatment.

In an embodiment, the neuropsychiatric disorder is a neurodegenerative disease, such as Alzheimer's disease, mild cognitive impairment, Lewy-body dementia, progressive supranuclear palsy, Parkinson's disease, or frontotemporal dementia. In an embodiment, the neuropsychiatric disease is one that is not a neurodegenerative disease, such as depression, obsessive compulsive disorder, Tourette's syndrome, post-traumatic stress disorder and traumatic brain injury.

In addition to the exemplary aspects and embodiments described above, further aspects and embodiments will become apparent by reference to the drawings and by study of the following descriptions.

Additional embodiments of the present methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

BRIEF DESCRIPTION OF THE DRAWINGS

FIGS. 1A-IC show a correlation matrix of functional connectivity network changes in regions of interest in the brain, as measured using functional MRI, in subjects at baseline, one week after treatment and one month after treatment.

DETAILED DESCRIPTION

I. Definitions

Figure 2:
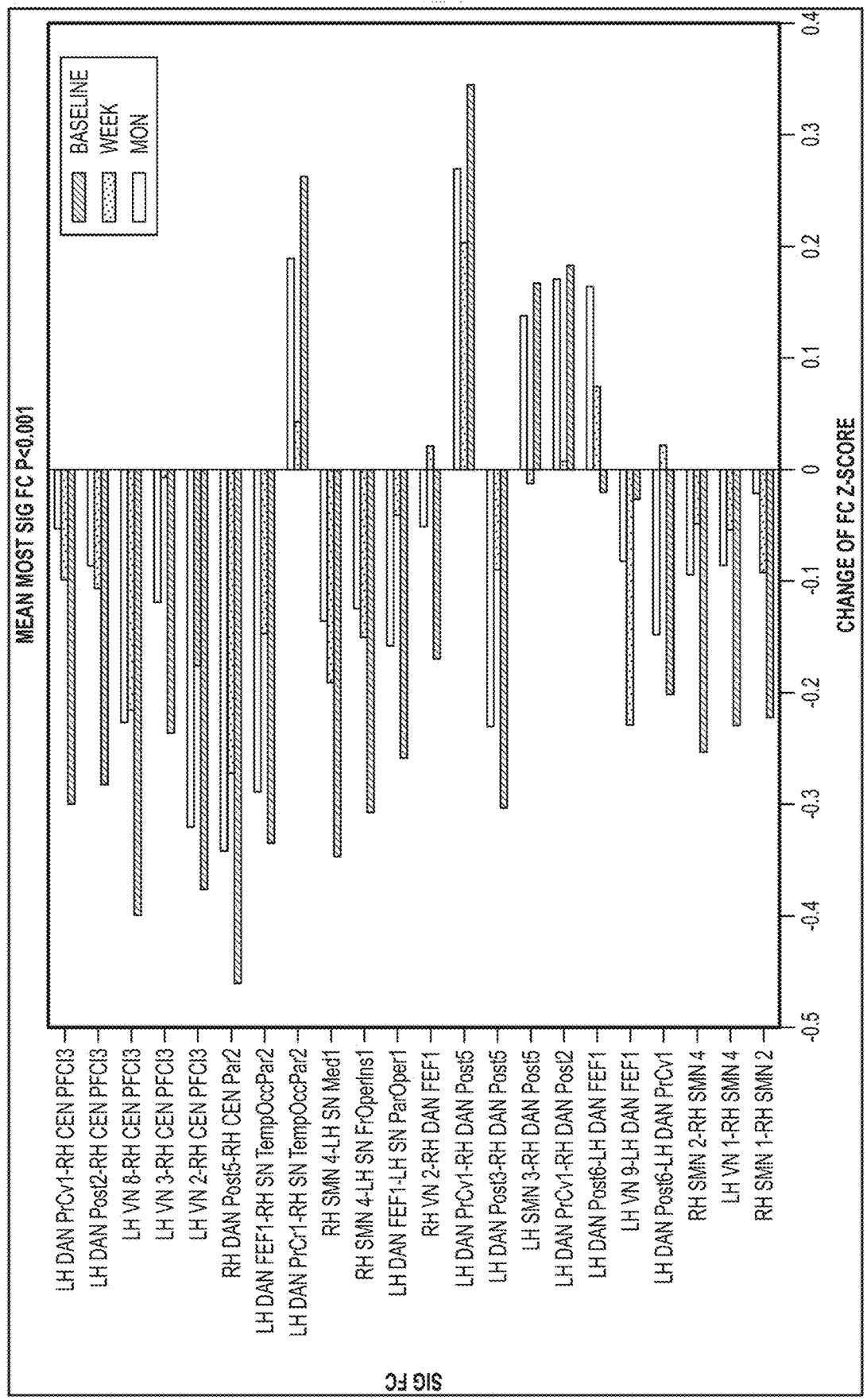
FIG. 2 is a graph showing changes in functional connectivity Z-scores for significant functional connectivity networks subjects at baseline, one week after treatment and one month after treatment.

Various aspects now will be described more fully hereinafter. Such aspects may, however, be embodied in many different forms and should not be construed as limited to the embodiments set forth herein: rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The compositions of the present disclosure can comprise, consist essentially of, or consist of, the components disclosed.

All percentages, parts and ratios are based upon the total weight of the composition and all measurements made are at about 25° C., unless otherwise specified.

"Administration" refers to introducing an agent, such as an *iboga* alkaloid, into a subject or patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The agent, such as an *iboga* alkaloid, may be administered by direct blood stream delivery, e.g. sublingual, buccal, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Ibogaine" refers to the compound:

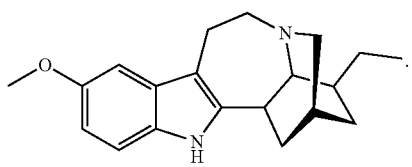

as well as pharmaceutically acceptable salts and pharmaceutically acceptable solvates thereof. It should be understood that where "ibogaine" is mentioned herein, one or more polymorphs of ibogaine can be utilized and are contemplated. Ibogaine is isolated from *Tabernanth iboga*, a shrub of West Africa. Reference to a derivative of ibogaine or an ibogaine derivative intends a compound other than ibogaine and based on the molecular core of ibogaine, and non-limiting examples of ibogaine derivatives are provided, for example, in WO2017/184531, which are incorporated by reference herein.

"Noribogaine" refers to the compound:

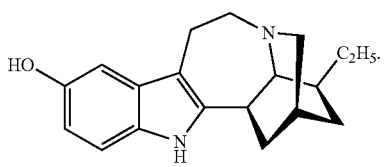

as well as pharmaceutically acceptable salts thereof or solvates thereof. Noribogaine can be prepared by demethylation of naturally occurring ibogaine. Demethylation may be accomplished by conventional techniques such as by reaction with boron tribromide/methylene chloride at room temperature followed by conventional purification. See, for example, Huffman, et al., *J. Org. Chem* 50:1460 (1985). Noribogaine can be synthesized as described, for example, in U.S. Patent Pub. Nos. 2013/0165647, 2013/0303756, and 2012/0253037, PCT Patent Publication No. WO 2013/040471 (includes description of making noribogaine polymorphs), and U.S. Pat. No. 9,617,274, each of which is incorporated herein by reference in its entirety.

"Neuropsychiatric" is used herein with reference to disorders of affect, cognition, and/or behavior that arise from a disorder in cerebral structure and/or function and/or from indirect effects of an extracerebral disease. Neuropsychiatric disorders include neurological disorders and neurodegenerative disorders.

As used herein, the term "patient" or "subject" refers to mammals and includes humans and non-human mammals.

The phrase "pharmaceutically acceptable" is employed herein to refer to those compounds, salts, compositions, dosage forms, etc., which are within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

"Pharmaceutically acceptable salt" refers to salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount may vary depending upon the patient and the condition being treated, the gender, weight and age of the subject, the severity of the condition, presence of co-morbidities, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of an agent, in the context of treating a neurodegenerative disease or a movement disorder and/or symptoms thereof, refers to an amount of the agent that attenuates the disease or disorder: attenuates, reverses, or reduces the severity of a symptom or symptoms thereof; and/or prevents, delays, or reduces the severity of progression of the disease or disorder.

A "therapeutic level" of a drug is an amount of *iboga* alkaloid or pharmaceutically acceptable salt or solvate thereof that is sufficient to treat or prevent the disease or disorder and/or symptoms thereof, but not high enough to pose any significant risk to the patient. Therapeutic levels of drugs can be determined by tests that measure the actual concentration of the compound in the blood of the patient. This concentration is referred to as the "serum concentration."

The term "treating" is used herein, for instance, in reference to methods of treating a neuropsychiatric disorder, and generally includes the administration of a compound or composition which reduces the frequency of, or delays the onset of, symptoms of a medical condition (e.g., a neuropsychiatric disorder or a neurological disorder or a neurodegenerative disorder) in a subject relative to a subject not receiving the compound or composition. This can include reversing, reducing, or arresting the symptoms, clinical signs, biological signed, and/or underlying pathology of a condition in a manner to improve or stabilize a subject's condition.

The term "unit dose" refers to a dose of drug provided to a patient to provide a therapeutic result, independent of the weight of the patient. The unit dose can be a standard form (e.g., a tablet or capsule). The unit dose may be administered as a single dose or a series of subdoses that collectively equal the single dose.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Iboga Alkaloid Compositions

Iboga alkaloids are alkaloid constituents of the *Tabernathe iboga*. Ibogaine, ibogaline, ibogamine and tabernathine are representative molecules, and are psychoactive. Despite being known for over a century, the full scope of effects on the human body have remained unclear. For example, ibogaine has been reported to be effective in treating substance addiction, such as alcohol addiction and drug addiction, including opioid and stimulant drugs, but has remained a less used pharmaceutical option due to its hallucinogenic (oneirogenic) effect and potential for neurotoxic and cardiovascular side effects. Approximately 1 in 300 people may suffer from cardiac arrest when treated with ibogaine. Given the dangers of the drug, ibogaine has been classified in the United States as a Schedule I controlled substance.

An exemplary *iboga* alkaloid is ibogaine. Ibogaine is a naturally occurring psychoactive molecule found in plants in the family Apocynaceae, most familiarly in *Tabernanthe iboga*. Ibogaine when orally administered to humans has a half-life of about 7.5 hours, and possibly longer in subjects that are poor CYP2D6 metabolizers. Ibogaine can cause long QT syndrome by blocking hERG potassium channels in the heart, leading to death. Ibogaine's cardiotoxicity renders it unsafe for use in patient treatment. The compositions and methods described herein provide a solution. Another exemplary *iboga* alkaloid is noribogaine, which has half-life of 28-49 hours. These compounds are lipophilic and distribute widely in the body and accumulate in fatty tissues, such as brain, heart and adipose.

Compositions comprising an *iboga* alkaloid or salt thereof and a cardioprotective agent are provided. The compositions are not limited to any particular chemical form of *iboga* alkaloid, and the compound may be present in the composition as a free base or as a pharmaceutically acceptable salt. The cardioprotective agent is, in an embodiment, a compound with activity to reduce risk of a drug-induced long QT syndrome and/or with activity to mitigate risk associated with drug-induced long QT syndrome. In other embodiments, the cardioprotective agent is a compound with activity to reduce long QT syndrome or QT prolongation in a subject. In other embodiments, the cardioprotective agent has a stabilization effect on cardiac membrane that is independent of QT changes.

Ibogaine and its principal metabolite noribogaine demonstrate moderate-to-weak affinity for a number of neurotransmitter receptors including N-methyl-D-aspartate, kappa and mu opioid, sigma-1 and -2, nicotinic acetylcholine, serotonin transporter, and dopamine transporter, among others (Litjens, R. P. W. et al., *Clin. Toxicol.*, 54, 297-302 (2016); Corkery, J. M., *Progress in Brain Research*. 242: 217-257 (Elsevier, 2018): Wasko, M. J. et al., *ACS Chem. Neurosci.* 9, 2475-2483 (2018)). Ibogaine also increases the transcription of neurotrophic factors including brain-derived neurotrophic factor (BDNF) and glial cell line-derived neurotrophic factor (GDNF) (Marton, S. et al., *Front. Pharmacol.* 10. (2019)) and increases cortical neuron dendritic arbor complexity in vitro (Cameron, L. P. et al., *Nature.* 589, 474-479 (2021)).

The *iboga* alkaloid may be present in the composition as a free base or as a salt, and in an embodiment, as a pharmaceutically acceptable acid addition salt. In an embodiment, the *iboga* alkaloid is a hydrochloride salt, exemplified by ibogaine hydrochloride, however other salts derived from organic or inorganic acids may also be used. Examples of such acids include, without limitation, those described above as pharmaceutically acceptable salts and the like.

In embodiments, the cardioprotective agent is a mineral, a sodium channel blocker (a class 1B antiarrhythmic), a potassium channel blocker, an hERG (human ether-a-go-go-related gene) channel agonist, and/or a beta adrenoceptor agonist. Exemplary sodium channel blockers are mexiletine, tocainide, lidocaine, flecainide, and R-56865 (2-benzothiazolamine, N-(1-(4-(4-fluorophenoxy)butyl)-4-piperidinyl)-N-methyl). Exemplary potassium channel blockers are amiodarone and ranolazine. Exemplary minerals are magnesium, calcium and/or potassium. Exemplary hERG channel agonists include RPR260243 ([(3R,4R)-4-[3-(6-methoxy-quinolin-4-yl)-3-oxo-propyl]-1-[3-(2,3,5 trifluorophenyl)-prop-2-ynyl]-piperidine-3-carboxylic acid]), PD-118057 ([2-(4-[2-(3,4-dichloro-phenyl)-ethyl]-phenylamino)-benzoic acid]), and NS1643 (N,N'-bis[2-hydroxy-5-(trifluoromethyl)phenyl]-urea). An exemplary beta adrenoceptor agonist is isoproterenol. The cardioprotective agent can be in salt, base or elemental form.

In an embodiment, the cardioprotective agent is not a CYP2D6 inhibitor, a CYP2D6 inhibitor administered at a dose ineffective to inhibit CYP2D6, and/or amiodarone.

In an embodiment, the cardioprotective agent is a mineral, and in an embodiment, the mineral is present in the composition in the form a salt. In an embodiment, the mineral salt is an electrolyte. In an embodiment, the electrolyte is calcium, sodium, potassium, phosphate, magnesium and/or chloride. Exemplary salts of magnesium include magnesium aspartate, magnesium aspartate hydrochloride, magnesium bisglycenate, magnesium carbonate, magnesium chloride, magnesium citrate, magnesium gluconate, magnesium glycinate, magnesium hydroxide, magnesium lactate, magnesium malate, magnesium oxide, magnesium sulfate, and magnesium taurate. Exemplary salts of potassium and calcium include potassium chloride, potassium citrate, potassium bicarbonate, calcium gluconate, calcium chloride, calcium citrate, calcium glubionate, calcium gluceptate, calcium carbonate, and calcium acetate.

In an embodiment, the salt form of the mineral or electrolyte is not a fatty acid salt form of the mineral or electrolyte. In an embodiment, a fatty acid refers to a carboxylic acid with a saturated or unsaturated, branched or linear, aliphatic chain. In an embodiment, the aliphatic chain has about four or more, five or more, six or more carbon atoms. For example, the aliphatic chain may have between about 4-26, 5-26, 6-26, 7-26 or 8-26 carbon atoms. In an embodiment, the cardioprotective agent is not a magnesium salt of a fatty acid. In an embodiment, the cardioprotective agent is not magnesium stearate.

In an embodiment, the cardioprotective agent is a magnesium salt that ionizes in an aqueous medium to a magnesium cation and an anion or anion pair, the anion or the anion pair having a molecular mass of less than about 200 g/mol, 225 g/mol, 250 g/mol. 275 g/mol or 280 g/mol. In an embodiment, the cardioprotective agent is a magnesium salt that is essentially completely soluble in water at 25° C. In an embodiment, the cardioprotective agent is a magnesium salt that has a water solubility at 25° C. of greater than about 5 g/L, 10 g/L, 25 g/L or 50 g/L.

In embodiments, the cardioprotective agent is in the composition in an amount effective to achieve a physiologic effect to reduce risk of a drug-induced long QT syndrome. For example, in embodiments where the cardioprotective agent is magnesium, potassium or calcium, the composition can include a salt of magnesium, potassium or calcium, where the salt form is present in the composition in an amount effective to achieve a physiologic effect on the QT interval. In embodiments, the cardioprotective agent is administered in an amount effective to shorten the QT interval and/or to reduce risk of developing drug-induced QT prolongation. In an embodiment, the effective amount is an amount to reduce risk associated with a drug-induced long QT syndrome. In an embodiment, the effective amount is an amount to stabilize a cardiac membrane independent of QT change.

In embodiments where the cardioprotective agent is magnesium, potassium or calcium, the composition can include a salt of magnesium, potassium or calcium in an amount that provides a dose of the mineral (i.e., an elemental dose or amount) effective to achieve a physiologic effect on the QT interval, to shorten the QT interval, to reduce risk of developing a prolonged QT interval, to stabilize a cardiac membrane, and/or to reduce risks of a long QT interval. In an embodiment, the effective amount is an elemental amount to reduce risk of a drug-induced long QT syndrome.

In studies performed herein, and discussed below with reference to Example 1, the cardioprotective agent magnesium was administered to the subjects. The amount (weight) of magnesium salt in the composition will vary according to its salt form, as can be appreciated. In an embodiment, the composition comprises magnesium salt in an amount between about 50-8000 mg, 250-8000 mg, 500-8000 mg, 1000-8000 mg, 50-6000 mg, 250-6000 mg, 500-6000 mg, 1000-6000 mg, 1500-6000 mg, 50-5000 mg, 250-5000 mg, 500-5000 mg, 2000-5000 mg, 50-4000 mg, 250-4000 mg, or 500-4000 mg.

In other embodiments, the composition comprises an amount of a mineral salt, such as a potassium, a chloride, or a magnesium salt, that provides a dose of elemental mineral of between about 0.01-500 moles, 0.01-300 moles, 0.01-250 moles, 0.01-200 moles, 0.01-150 moles, 0.01-100 moles, 0.01-50 moles, 0.5-500 moles, 0.5-300 moles, 0.5-250 moles, 0.5-200 moles, 0.5-150 moles, 0.5-100 moles, 0.5-50 moles, 1-500 moles, 1-300 moles, 1-250 moles, 1-200 moles, 1-150 moles, 1-100 moles, 2-500 moles, 2-300 moles, 2-250 moles, 2-200 moles, 2-150 moles, 2-100 moles, 5-500 moles, 5-300 moles, 5-250 moles, 5-200 moles, 5-150 moles, 5-100 moles, 10-500 moles, 10-300 moles, 10-250 moles, 10-200 moles, 10-150 moles, or 10-100 moles. In other embodiments, the dose of elemental mineral provides between about 1-500 mEq, 1-300 mEq, 1-250 mEq, 1-200 mEq, 2-500 mEq, 2-300 mEq, 2-250 mEq, 2-200 mEq, 5-500 mEq, 5-300 mEq, 5-250 mEq, 5-200 mEq, or 5-150 mEq.

In an embodiment, the cardioprotective agent is magnesium administered in the form of a salt, such as magnesium sulfate or magnesium oxide.

The cardioprotective agent can be administered prior to, concurrently with, and/or subsequent to administration of the *iboga* alkaloid. The cardioprotective agent can be administered via any route of administration, and examples are discussed infra.

The composition comprises an amount of the *iboga* alkaloid or salt thereof in a amount to provide a desired therapeutic effect, as discussed herein with regard to treating neuropsychiatric disorders. Studies were performed, as discussed with reference to Example, with the *iboga* alkaloid ibogaine. More particularly, ibogaine in its hydrochloride salt form was used as a model agent to demonstrate the compositions and methods described herein. In an embodiment, the composition comprises a salt of ibogaine in an amount of between about 200-5000 mg, 200-3000 mg, 200-2500 mg, 200-2000 mg, 200-1800 mg, 200-1500 mg, 250-2500 mg, 250-2000 mg, 250-1800 mg, 250-1500 mg, 300-5000 mg, 300-3000 mg, 300-2500 mg, 300-2000 mg, 300-1800 mg, 300-1500 mg, 350-5000 mg, 350-3000 mg, 350-2500 mg, 350-2000 mg, 350-1800 mg, 350-1500 mg, 400-5000 mg, 400-3000 mg, 400-2500 mg, 400-2000 mg, 400-1800 mg, 400-1500 mg, 450-5000 mg, 450-3000 mg, 450-2500 mg, 450-2000 mg, 450-1800 mg, 450-1500 mg, 500-5000 mg, 500-3000 mg, 500-2500 mg. 500-2000 mg, 500-1800 mg, 500-1500 mg, 500-1600 mg, 500-1250 mg, 550-5000 mg, 550-3000 mg, 550-2500 mg, 550-2000 mg, 550-1800 mg, 550-1600 mg, 550-1500 mg, 500-1250 mg, 600-5000 mg, 600-3000 mg, 600-1500 mg, 650-5000 mg, 650-3000 mg, 650-1500 mg. 650-1400 mg, 650-1400 mg, 700-5000 mg, 700-3000 mg, 700-2000 mg, 700-2500 mg, 700-1500 mg, 700-1400 mg, 700-1600 mg, 750-1600 mg, 750-1850 mg, 800-5000 mg, 800-3000 mg, 800-2500 mg, 800-2400 mg, 800-2250 mg, 800-2000 mg, 800-1800 mg, 800-1500 mg, 800-1600 mg, 800-1250, 850-5000 mg, 850-3000 mg, 850-2500 mg, 850-2400 mg, 850-2250 mg, 850-2000 mg, 850-1800 mg, 850-1600 mg, 850-1500 mg, or 850-1250 mg.

The composition comprising the *iboga* alkaloid and cardioprotective agent can be of any form. In embodiments, and as can be appreciated, the form of the composition may depend on the intended route of administration. In embodiments, the *iboga* alkaloid and cardioprotective agent are formulated together in a single dosage form. In embodiments, the *iboga* alkaloid and cardioprotective agent are formulated each in a single dosage form for administration sequentially or concurrently.

The composition can be a solid dosage form. In an embodiment, the solid dosage form in intended for oral ingestion. Examples of orally ingestible dosage forms include a powder, a capsule, a pill, or a tablet. In other embodiments, the solid dosage form is for sublingual, buccal, rectal or topical administration. The dosage form can be formulated to provide immediate release of one or both of the *iboga* alkaloid and cardioprotective agent upon oral administration. For example, a dosage form that releases the *iboga* alkaloid or salt thereof at least about 0.25 hours, 0.5 hours, 1 hour, 1.5 hours, 2 hours, 2.5 hours or 3 hours after release of the cardioprotective agent is contemplated.

An exemplary dosage form is an orally ingestible powder, capsule, pill, or tablet comprising an amount of an *iboga* alkaloid and an amount of a cardioprotective agent. In an embodiment, the *iboga* alkaloid is ibogaine. In an embodiment, the *iboga* alkaloid is a salt form of ibogaine, such as ibogaine hydrochloride. In an embodiment, the cardioprotective agent is an electrolyte, such as magnesium or any of the other minerals mentioned herein. The dosage form comprises an amount of ibogaine and an amount of cardioprotective agent in any of the amounts mentioned herein.

In embodiments, the composition can be suitable for a variety of delivery modes including, without limitation, oral, sublingual, buccal, intrapulmonary, or intranasal delivery. Compositions suitable for internal, rectal, vaginal, lingual, intravenous, intraarterial, intramuscular, intraperitoneal, intracutaneous and subcutaneous routes may also be used. Other dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A Oslo editor, Easton Pa. 1980).

In one embodiment, an *iboga* alkaloid or pharmaceutically acceptable salt or solvate thereof is administered orally, which may conveniently be provided in tablet, caplet, sublingual, liquid or capsule form. Solutions can be prepared using water or physiologically compatible organic solvents such as fatty alcohols, triglycerides, glycerine and the like. Parenteral compositions containing *iboga* alkaloid or pharmaceutically acceptable salt or solvate thereof may be prepared using conventional techniques that may include sterile isotonic saline, water, Ringer's solution, etc. Compositions for sublingual administration, for example as sublingual tablets may be designed to dissolve rapidly and can contain in addition to the *iboga* alkaloid and/or the cardioprotective agent, an excipients such as lactose, sucrose, dextrose or mannitol.

In other embodiments, a kit comprising a device comprising a plurality of unit doses of a cardioprotective agent and a unit dose of an *iboga* alkaloid or salt thereof and instructions for use is provided. In one embodiment, the plurality of unit doses of cardioprotective agent comprises a plurality of unit doses for oral administration of the cardioprotective agent. For example, each unit dose of cardioprotective agent in the kit can be a solid dosage form, such as a pill, capsule, tablet, caplet, or a powder. Each unit dose of cardioprotective agent, in other embodiments, can be a liquid dosage form, such as a solution, suspension, elixir, or syrup. In other embodiments, the plurality of unit doses of cardioprotective agent comprise a first set that is a solid dosage form and a second set that is a liquid dosage form: that is, the unit doses in the plurality are a mixture of solid dosage forms and liquid dosage forms. In embodiments, one or more of the unit doses is a solid, such as a powder, that is mixed with a liquid, such as water or juice, for ingestion by the patient. In other embodiments, one or more of the unit doses of cardioprotective agent is a liquid suitable for nasal administration or parenteral administration.

In embodiments, the kit or device of the kit comprises a unit dose of *iboga* alkaloid or salt thereof in the form of a solid or a liquid. The solid unit dose can be, for example, a pill, capsule, tablet, caplet, or a powder. The liquid unit dose can be, for example, an elixir, a syrup, a suspension or a solution. In other embodiments, the unit dose of *iboga* alkaloid or salt thereof is a liquid suitable for nasal administration or parenteral administration.

In an embodiment, the device comprising the unit dose of *iboga* alkaloid or salt thereof and/or the plurality of unit doses of cardioprotective agent is a blister pack. In other embodiments, the kit comprises a device comprising the unit dose of *iboga* alkaloid and a container or collection of packets with a plurality of doses of the cardioprotective agent. In other embodiments, the kit comprises a blister pack with at least one unit dose of *iboga* alkaloid or salt thereof and at least one unit dose of a cardioprotective agent. In other embodiments, the kit comprises a blister pack with at least one unit dose of *iboga* alkaloid or salt thereof and two or more unit dose of a cardioprotective agent. In embodiments, each unit dose in the blister pack is in a separate blister of the blister pack. By way of example, a kit comprising a plurality of doses of a magnesium salt, calcium salt or potassium salt (or combination of mineral salts) is provided, where in embodiments the plurality of doses are in a blister pack of individual unit doses, in a collection of containers each with a unit dose, or in a single container comprising the plurality of doses. The kit further comprises at least one dose of, for example, ibogaine hydrochloride.

In an embodiment, the device further comprises a second unit dose of the *iboga* alkaloid or salt thereof. In an embodiment, the second unit dose of the *iboga* alkaloid or salt thereof is at a dose different than the first unit dose or at the same dose as the first unit dose. In an embodiment, the second unit dose of the *iboga* alkaloid or salt thereof is at a dose less than the dose of the *iboga* alkaloid or salt thereof in the first unit dose. In an embodiment, the plurality of unit doses of cardioprotective agent comprise a plurality of unit doses at different doses and/or of unit doses formulated for different routes of administration.

III. Methods of Treatment

In an embodiment, a method for treating a neuropsychiatric disorder is provided. The method comprises administering, or instructing to administer, to a subject a cardioprotective agent in an amount effective to achieve a physiologic effect to reduce risk of long QT syndrome and administering an *iboga* alkaloid or salt thereof and monitoring the subject by analyzing image data from a brain image. In an embodiment, the image data is analyzed with a model to determine a predicted brain age. In embodiments, the neuropsychiatric disorder is a neurological disorder or a neurodegenerative disease.

A study was conducted to evaluate safety and efficacy of ibogaine, as an exemplary *iboga* alkaloid, in special operations veterans with combat and/or blast exposure, as described in Example 1. Veterans are more likely to have chronic conditions. Substance use in four times higher in veterans than the general population, with an incidence of lifetime trauma a primary predictor of developing substance use disorder (Barsuglia et al., *Prog. Brain. Res.,* 424:121-158 (2018)). Traumatic brain injury is a signature injury of veterans, with almost half (46%) of returning U.S. military personnel from conflicts in Iraq and Afghanistan screening positive for TBI (Morissette et al., *Rehabil Psychol.,* 56 (4): 240-350 (2011)). Common mechanisms of injury include blasts, car accidents and falls (Schneiderman et al., *Am J. Epidemiol,* 167:144601452 (2008)). A majority of traumatic brain injuries are mild or moderate, and form the basis of most TBI research. Most patients with a mild or moderate TBI (mTBI) recover within weeks, but many develop symptoms that last for months or years (Vanderploeg et al, *J. Clinical and Experimental Neuropsychology,* 29 (6): 585-598 (2007)). In a sample of patients with mTBI three months after initial injury, 79% complained of at least one persistent symptom and 34% still had a functional disability (Rimel et al., *Neurosurgery,* 9 (3): 221-229 (1981)). TBI is highly comorbid with PTSD, with 33-39% of soldiers with mTBI having PTSD (Polusny et al., *Arch Gen Psychiatry,* 68 (1): 79-89 (2011)). Other estimates are that PTSD prevalence after TBI in the general population range from 1-50%. PTSD is the most common psychiatric condition among veterans with TBI. Psychosocial and functional impairments are common in both disorders, as psychological trauma often co-occurs with biomechanical trauma. Damage to the frontal cortex during TBI may make patients more vulnerable to uncontrolled anxiety and fear reactions. Patients suffering from TBI and PTSD tend to complain of more severe neurocognitive symptoms.

In an embodiment, the neuropsychiatric disorder is traumatic brain injury (TBI) and a method for treating TBI is provided. TBI is a leading cause of disability worldwide and is a signature injury of US Veterans from recent military conflicts, most often caused by blast exposure. Clinically, sequelae of TBI can include posttraumatic stress disorder (PTSD), major depressive Disorder (MDD), and anxiety disorders, but efficacy of treatments for these complications is limited. For example, first-line therapies for PTSD are less effective in veteran populations (Beidel, D. C. et al. *Contemp. Clin. Trials Commun.* 17, 100491 (2020); Bryan, C. J. et al., *Psychol. Trauma Theory Res. Pract. Policy* 10, 36-45 (2018); Steenkamp, M. M. et al., *JAMA* 323, 656-657 (2020))), and overall remission rates of available treatments for these complications range from 20-40% (Steenkamp, M. M. et al., *JAMA* 314, 489-500 (2015): Alexander, W., *Pharm. Ther.* 37, 32-38 (2012)). Perhaps most concerningly, veterans make up 20% of suicides in the US despite making up only 6.4% of the general population (Inoue, C. et al., *StatPearls* (StatPearls Publishing, 2022). As mentioned above, ibogaine is linked to neuro- and cardiotoxicity concerns (Litjens, R. P. W. et al., *Clin. Toxicol.* 54, 297-302 (2016): Ona, G. et al. *Psychopharmacology (Berl.)* 239, 1977-1987 (2022)). In regards to the former, only transient ataxia has been reported in humans (Litjens et al., supra). In the case of the latter, however, lengthening of the time of ventricular depolarization and repolarization (QT interval prolongation) with instances of subsequent fatal arrhythmia has occurred (Ona, G. et al., supra). High doses of ibogaine, pre-existing conditions, drug-drug interactions, and lack of vital sign monitoring may have played critical roles in these cases (Litjens et al., supra).

As described in Example 1, subjects that were special operations veterans were enrolled for treatment with ibogaine and psychological testing, neuropsychological testing, fMRI, EEG and self-report measures On the day of treatment, participants were administered one gram of prophylactic magnesium sulfate intravenously and 12.1±1.2 (mean±SD) mg/kg of oral ibogaine while under medical supervision. An additional dose of magnesium was administered approximately 12 hours later.

For simplicity, reference herein to "post treatment", "after treatment", "post ibogaine treatment" and "after ibogaine treatment", and variations of these phrases, refer to the period subsequent to the treatment regimen of Example 1 where a cardioprotective agent was administered in conjunction with (e.g., prior to, during or after administration of) an *iboga* alkaloid, exemplified by ibogaine. Reference to 'immediate post' treatment. '4 days post treatment' and '1 week post treatment' refer to the first assessment made post treatment with ibogaine (as an exemplary *iboga* alkaloid) and a cardioprotective agent, which was typically 4 days after ibogaine administration or in some cases 1 week after ibogaine administration. Reference to "one-month post treatment" refers to the assessment made one month after treatment with ibogaine (as an exemplary *iboga* alkaloid) and cardioprotective agent.

To assess for cognitive effects of ibogaine in combination with a cardioprotective agent a neuropsychological battery was administered to participants at all three timepoints. A summary of the results is in Table 1 and Table 1-6 of Example 1. Results indicated statistically significant improvements in processing speed with large effect sizes (D=0.97-1.34) and executive functioning (including inhibition, cognitive flexibility, problem-solving, phonemic fluency, and working memory: with effects ranging from small to large: D=0.31-1.22) both immediately post-ibogaine and at the one-month follow-up. Mean performances on these tests moved from the Average to High Average score range relative to age peers in all but one instance (phonemic fluency was High Average at baseline and improved to the Superior range relative to age peers at the one-month follow-up: (D=1.11). Learning and memory tests showed a significant improvement in visual memory at both timepoints and in verbal memory at the one-month follow-up. Sustained attention showed a significant improvement in accuracy (detection) at both time points with large effect sizes (D=0.86-1.05), and a weak but significant slowing of reaction time (D=0.29-0.52), consistent with a prioritization of accuracy over speed and reduced impulsivity. No significant performance changes were observed in language (semantic fluency). No declines were noted across any performance domain. In Table 1, neuropsychological test scores are represented as a T score (mean of 50, SD of 10). Unless stated otherwise, a higher score represents better performance.

TABLE 1

Baseline and follow-up statistics of neuropsychological testing. All results presented as mean ± SD.

| Neuropsych. Construct | Test Item | Baseline | 1-wk post | Baseline vs 1-wk post $F^a$ | p(FDR) | D | 1-mo. post | Baseline vs 1-month post $F^a$ | p(FDR) | D |
|---|---|---|---|---|---|---|---|---|---|---|
| Sustained Attention | | | | | | | | | | |
| Detectionb | CPT-3 Detection | 46.6 ± 10.3 | 41.2 ± 8.2 | 13.11 | 0.002* | 1.05 | 39.5 ± 7.5 | 19.90 | <0.001 | 0.86 |
| Reaction Time | CPT-3 Reaction Time | 43.0 ± 7.7 | 44.1 ± 6.8 | 1.38 | 0.285 | 0.29 | 46.4 ± 8.1 | 9.49 | 0.007* | 0.52 |
| Sustained Attention | CPT-3 Hit Reaction Time Block Change | 51.5 ± 8.8 | 50.8 ± 7.9 | 0.01 | 0.952 | 0.02 | 51.2 ± 7.7 | 0.39 | 0.583 | 0.29 |
| Learning and Memory | | | | | | | | | | |
| Verbal Memory | HVLT-R | 47.4 ± 10.1 | 49.0 ± 9.2 | 0.42 | 0.583 | 0.17 | 53.1 ± 8.8 | 6.47 | 0.024* | 0.47 |
| Visuospatial Memory | BVMT-R | 53.9 ± 11.4 | 58.8 ± 7.1 | 9.73 | 0.007 | 0.50 | 58.3 ± 6.6 | 4.41 | 0.052 | 0.32 |
| Processing speed | | | | | | | | | | |
| Processing Speed | PSI (WAIS-IV) | 53.8 ± 10.6 | 59.2 ± 9.7 | 27.85 | <0.001* | 0.97 | 61.6 ± 10.7 | 43.43 | <0.001* | 1.34 |

TABLE 1-continued

Baseline and follow-up statistics of neuropsychological testing. All results presented as mean ± SD.

| Neuropsych. Construct | Test Item | Baseline | 1-wk post | Baseline vs 1-wk post | | | 1-mo. post | Baseline vs 1-month post | | |
|---|---|---|---|---|---|---|---|---|---|---|
| | | | | $F^a$ | p(FDR) | D | | $F^a$ | p(FDR) | D |
| Executive Function | | | | | | | | | | |
| Cognitive Inhibition | D-KEFS Color/Word Interference, Condition 3 | 55.1 ± 8.8 | 59.9 ± 6.4 | 21.30 | <0.001* | 1.22 | 59.9 ± 7.5 | 15.79 | 0.001* | 0.62 |
| Cognitive Flexibility Composite | Average of: (1) D-KEFS TMT, Condition 4; (2) D-KEFS Color/Word Interference, Condition 4; (3) D-KEFS Verbal Fluency, Category Switching | 54.0 ± 8.0 | 56.6 ± 5.7 | 4.73 | 0.045* | 0.43 | 59.3 ± 5.0 | 17.62 | <0.001* | 0.74 |
| Phonemic Fluency | D-KEFS Verbal Fluency | 57.0 ± 11.7 | 60.8 ± 10.3 | 7.53 | 0.016* | 0.52 | 64.0 ± 10.1 | 21.99 | <0.001* | 1.11 |
| Working Memory | WMI (WAIS-IV) | 55.1 ± 8.3 | 57.0 ± 9.5 | 5.32 | 0.034* | 0.37 | 57.6 ± 9.2 | 6.02 | 0.027* | 0.31 |
| Problem Solving | D-KEFS TT, Total Achievement Score | 55.7 ± 6.4 | 59.1 ± 7.1 | 5.38 | 0.034* | 0.49 | 59.5 ± 7.9 | 6.42 | 0.024* | 0.44 |
| Language | | | | | | | | | | |
| Semantic Fluency | D-KEFS Verbal Fluency | 60.4 ± 11.4 | 60.2 ± 12.2 | 0.18 | 0.688 | 0.02 | 63.6 ± 7.8 | 2.00 | 0.200 | 0.24 |

[a] Degrees of freedom (df) were (1, 63) for CPT3, (1, 75) for working memory, verbal memory, and problem solving; and (1, 76) for visuospatial memory, cognitive inhibition, cognitive flexibility, phonemic fluency, semantic fluency, and processing speed.
[b] Lower score indicates better performance.
SD = Standard Deviation; CPT-3 = Conners Continuous Performance Test; HVLT-R = Hopkins Verbal Learning Test-Revised; BVMT-R = Brief Visuospatial Memory Test-Revised; PSI = Processing Speed Index; WAIS-IV = Wechsler Adult Intelligence Scale 4th Edition; D-KEFS = Delis-Kaplan Executive Function System; TMT = Trail Making Test; WMI = Working Memory Index; TT = Tower Test.

With regard to safety, there were no unexpected or serious treatment-emergent side effects, and there were no instances of a concerning prolongation of QTc. All participants experienced transient cerebellar signs such as mild ataxia and intention tremor that resolved within 24 hours. While experiencing the oneirogenic effects of ibogaine. 12 participants (40%) were treated for headache. 7 (23%) for nausea. 3 (10%) for anxiety. 2 (7%) for hypertension, and 1 (3%) for insomnia.

The data from the study of Example 1 revealed clinically and statistically significant improvements in functioning both immediately and one-month post-treatment with an *iboga* alkaloid, exemplified by ibogaine, and a cardioprotective agent. Secondary analyses showed that remission rates for comorbid PTSD, depression, and anxiety were around 80%. There were no unexpected or serious adverse events. The safety and efficacy of ibogaine treatment in combination with a cardioprotective agent was evaluated in subjects with a history of TBI. At baseline, study participants were experiencing clinically significant levels of disability. PTSD, depression, and anxiety. Following ibogaine treatment in combination with a cardioprotective agent, participants showed a remarkable reduction in these symptoms with large effect sizes (Cohen's D>2 on clinician rated psychiatric assessments), and the benefits were sustained at the one-month follow-up. Indeed, disability measures continued to improve, and psychiatric symptom remission and response rates one-month post-treatment remained high. With regard to safety, no serious or unexpected adverse events occurred, and management of AEs was uncomplicated. The study demonstrates the potential of ibogaine in combination with a cardioprotective agent to be a powerful therapeutic for the transdiagnostic psychiatric symptoms that can emerge following TBI, including suicidality. Considering that the average time since discharge from the military in the tested subjects was nearly eight years, these findings further suggest that ibogaine in combination with a cardioprotective agent is effective even when administered years following the injuries.

Functional magnetic resonance imaging (fMRI) was performed on the subjects enrolled in the study described in Example 1. Neuroimaging is a branch of medical imaging that focuses on the brain. It utilizes techniques of physics, optics, and mathematics to quantify brain structure and function. Most neuroimaging techniques are non-invasive or minimally invasive, and are used to diagnose and assess brain health and function. fMRI provides an indirect measure of hemodynamic response blood oxygenation level dependency and is underpinned by the theory that if metabolic resources are being allocated to areas, it suggests that neurons in that area must be firing and this means activation. fMRI observes time dependent changes in blood flow. During resting, subjects are asked to do nothing and the aim is to observe the brain at rest. When the subject is asked to perform a task, the aim is to observe how the brain works in response to the task. Other magnetic resonance based imaging techniques include: anatomical, which measures cortical thickness, area, gyrification, and volume; arterial spin labelling, which quantitatively measures tissue perfusion, cerebral blood flow, where perfusion refers to the delivery of oxygen and nutrients to tissue by means of blood flow; and, diffusion tensor imaging, which measures diffusion of water through white natter, such as neural fiber tracts. fMRI can provide a series of images that form a film, as opposed to a single image obtained in MRI.

The human brain is a series of well-organized and optimized series of efficient networks. Disease states can be characterized as abnormalities or inefficiencies in the networks and/or the global organization. Resting-state functional connectivity is one method to characterize disease states and effects of interventions. The functional connectivity networks evaluated in a region of interest in the brain included those identified in Table 2-1 of Example 2. Data from the fMRI study is presented in FIGS. 1-6.

FIGS. 1A-1C show a correlation matrix of functional networks in the brain, as measured using functional MRI, in subjects at baseline, one week after treatment and one month after treatment.

FIG. 2 is a graph showing significant changes in brain functional connectivity in Z-scores for subjects at baseline, one week after treatment and one month after treatment.

Figure 3A:
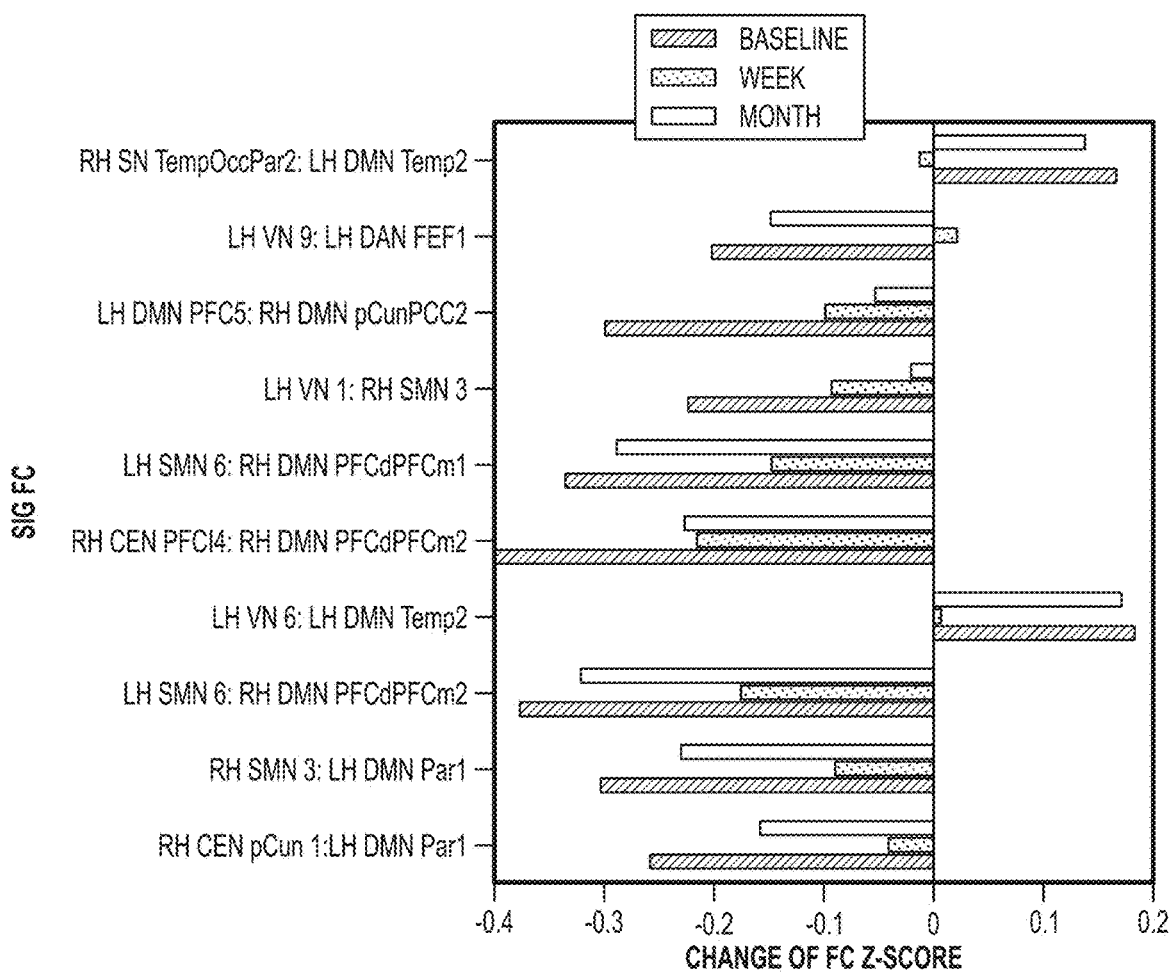
FIGS. 3A-3B are graphs showing changes in functional connectivity Z-scores for significant functional connectivity networks in subjects at baseline, one week after treatment and one month after treatment, with FIG. 3B offering a detail of the change in functional connectivity of the right hemisphere (RH) central executive network (CEN) in the precuneus brain region to the left hemisphere (LH) default mode network (DMN) in the parietal brain region.
Figure 3B:
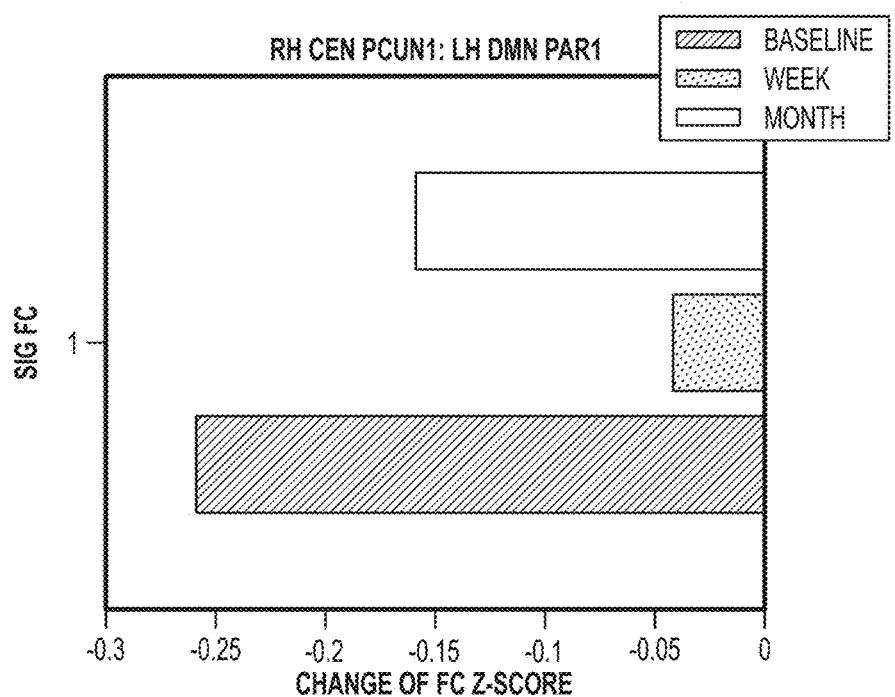

FIGS. 3A-3B are graphs showing significant changes in functional connectivity in Z-scores for subjects at baseline, one week after treatment and one month after treatment. FIG. 12B shows the change in functional connectivity of the right hemisphere (RH) central executive network (CEN) in the precuneus brain region to the left hemisphere (LH) default mode network (DMN) in the parietal brain region.

Figures 4A, 4B:
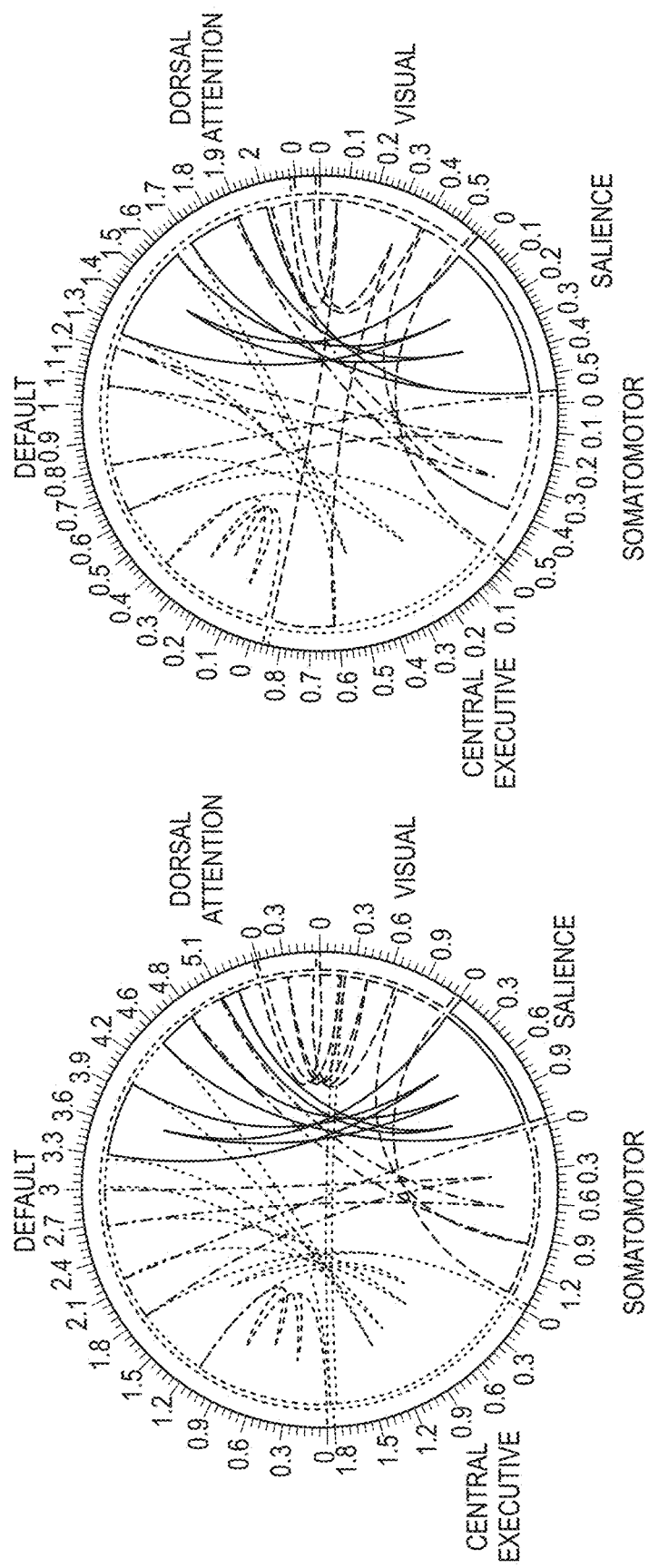
FIGS. 4A-4C provide visual representations of the reorganization of certain functional connectivity pairs in the brain network in subjects at baseline (FIG. 4A), one week after treatment (FIG. 4B), and one month after treatment (FIG. 4C).
Figure 4C:
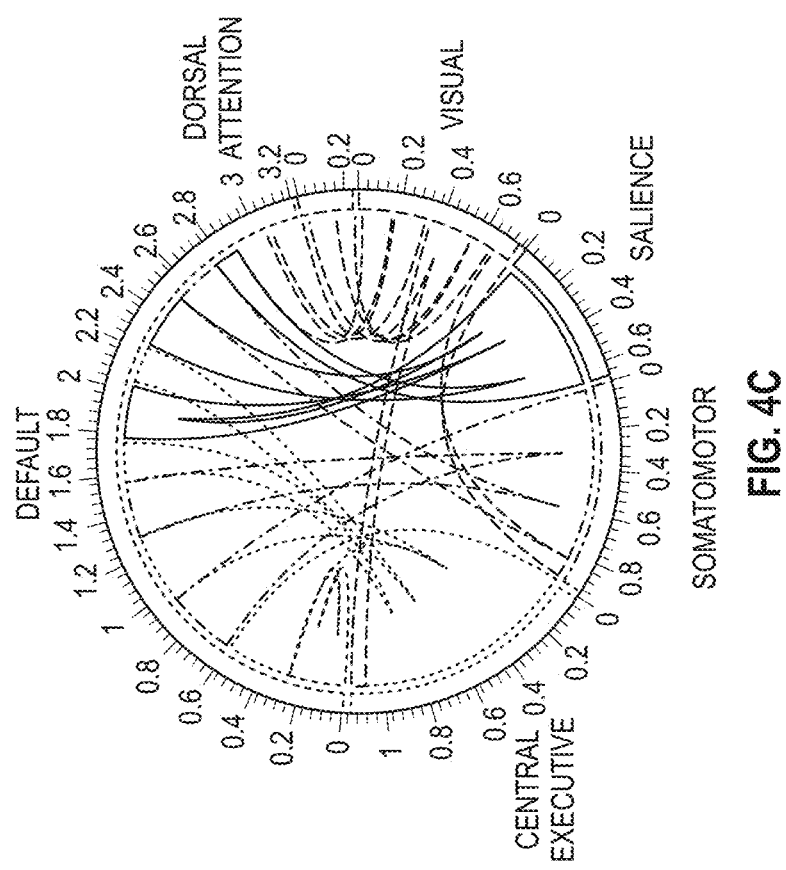

FIGS. 4A-4C provide visual representations of certain functional connectivity pairs in the brain network in subjects at baseline (FIG. 4A), one week after treatment (FIG. 4B), and one month after treatment (FIG. 4C), demonstrating changes in functional connectivity after treatment.

Figure 5:
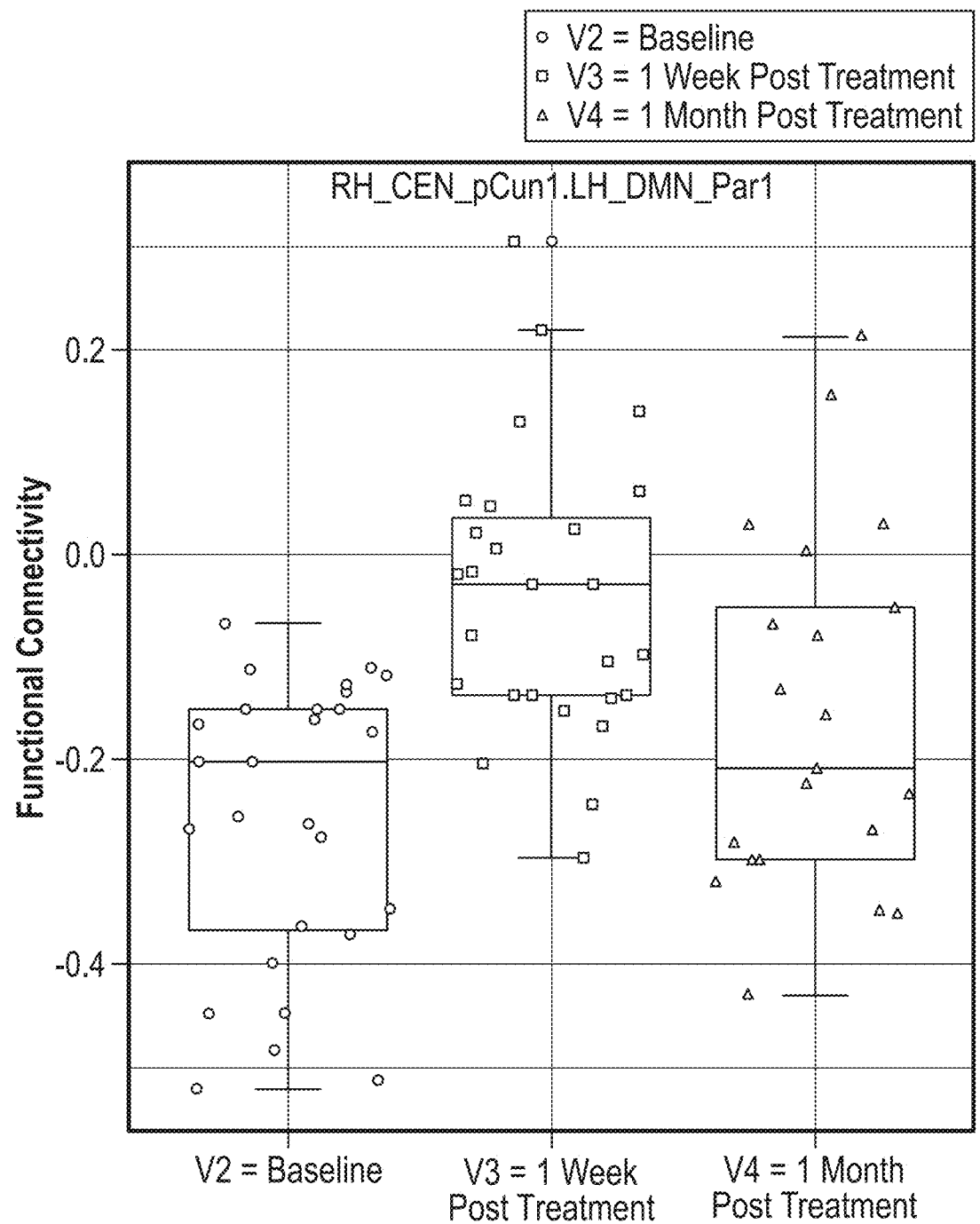
FIG. 5 is a graph showing group wide distribution of the functional connectivity of the right hemisphere (RH) central executive network (CEN) in the precuneus brain region to the left hemisphere (LH) default mode network (DMN) in the parietal brain region in subjects at baseline (v2), one week after treatment (v3) and one month after treatment (v4).

FIG. 5 is a graph showing group wide distribution of the functional connectivity of the right hemisphere (RH) central executive network (CEN) in the precuneus brain region to the left hemisphere (LH) default mode network (DMN) in the parietal brain region in subjects at baseline (v2), one week after treatment (v3) and one month after treatment (v4).

Figure 6:
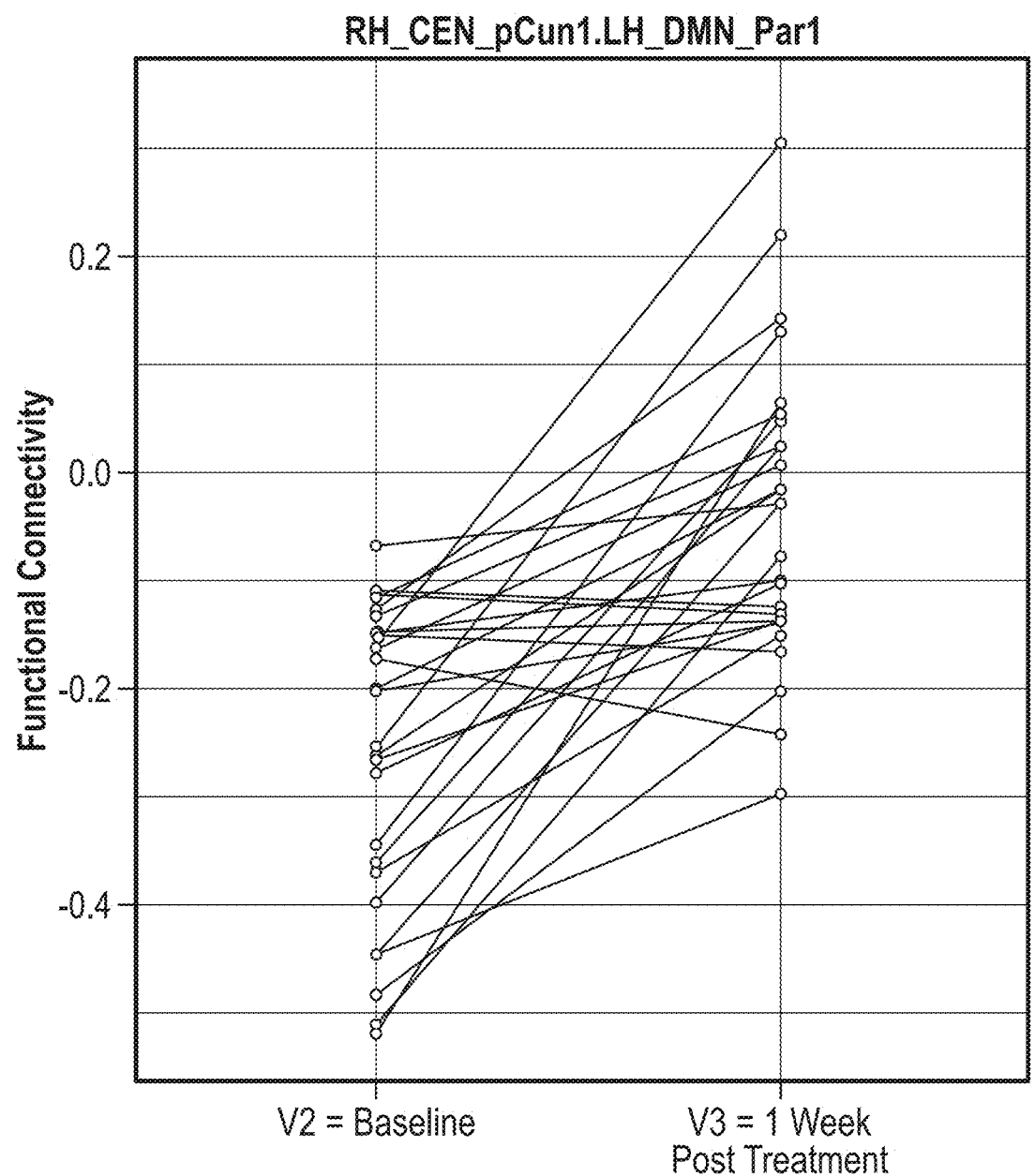
FIG. 6 is a graph showing changes in individual subjects of the functional connectivity of the right hemisphere (RH) central executive network (CEN) in the precuneus brain region to the left hemisphere (LH) default mode network (DMN) in the parietal brain region in subjects at baseline (v2) and one week after treatment (v3).

FIG. 6 is a graph showing changes in individual subjects of the functional connectivity of the right hemisphere (RH) central executive network (CEN) in the precuneus brain region to the left hemisphere (LH) default mode network (DMN) in the parietal brain region in subjects at baseline (v2) and one week after treatment (v3).

The data in FIGS. 1-6 demonstrate the resting-state functional connectivity (or differences in such connectivity pre- to post-treatment) observed between and within the most commonly described large scale brain networks as well as specific brain structures of interest. The data in Example 2 demonstrates that treatment with an *iboga* alkaloid as an intervention changes the functional connectivity architecture of the subjects.

fMRI data was also analyzed to inspect activity patterns as a function of time. A lag projection analysis measures temporal dynamics of blood oxygen level-dependent (BOLD) fMRI (Mitra et al., *PNAS*. E2235-E2244, 2015). Directed flow transfer of information is analyzed by comparing lag-correlation shift between voxel pairs. The average lag structure of a voxel indicates relative earliness or lateness in the brain, as a measure of whether the region is a source or sink of information. A paired T-test of fMRI images at baseline and about four days post treatment was done. A relative slowing in the following regions was observed (fwec p<0.001): left orbitofrontal gyrus (lateral and anterior) and inferior frontal gyrus (orbital and triangular, i.e., pars triangularis). These regions are involved in language formation, response inhibition and regulating goal-directed behavior. Slowing may reflect sustained processing and influence over the brain across long time scales.

Structural imaging of the brain was also conducted on some of the subjects of Example 1. Gray matter constitutes about 40% of the brain and white matter constitutes about 60% of the brain. Gray matter contains most of the brain's neuronal cell nodes, it is fully developed once a person reaches their 20's and interprets sensor information from various parts of the body. White matter is made up of bundles which connect various gray matter areas, it develops throughout the 20's and peaks in middle age. Typical metrics analyzed in anatomical (T1-weighted. "T1w") imaging include volume and/or shape of nuclei (e.g. caudate), volume and/or shape of ventricles of the brain, and cortical thickness (mm). These metrics can be used to study normal and abnormal neuroanatomy and are primarily used to quantify gray matter. A tool called FreeSurfer was applied to images for a T1w structural analysis (volume, cortical thickness) to adjust for bias, remove non-brain matter, segments by tissue, parcels the brain into standardized regions, and provides measurements of those regions. Free-Surfer measurements of whole brain volume, volume by tissue (gray, white, CSF), estimated intracranial volume (ICV), subcortical gray matter volume, cortical volume by region were done. Regional volume and cortical thickness were estimated at baseline and 1-month post treatment in 17 of the enrolled test subjects to probe for loss of brain tissue and/or indications of damaging effects after treatment with ibogaine. In particular, analysis was done to determine if there was any loss in gray matter volume or cortical thickness, whether there was a loss in white matter volume or an increase in presence of white matter hypotensities. Results are summarized in Table 2 and shown in FIGS. 7A-7B and FIGS. 8A-8B.

TABLE 2

Whole Brain Index Volumes - Baseline vs. one month post treatment

| Region of Interest | Statistical Analysis |
|---|---|
| Total Gray Matter | Two-tailed: no significant differences (p = 0.4755; alpha = 0.05) |
| Cortical Gray Matter | Two-tailed: no significant differences (p = 0.4847; alpha = 0.05) |
| Subcortical Gray Matter | Two-tailed: no significant differences (p = 0.0949; alpha = 0.05) Left tailed: p = 0.0475; alpha = 0.05 |
| Cerebral White Matter | Mean increase in volume = 2500 mm$^3$ Two-tailed: p = 0.03; alpha = 0.05 Left-tailed: p = 0.0150; alpha = 0.05 |
| White matter hypointensities (corrected for cerebral white matter) | Two-tailed: no significant differences (p = 0.0789; alpha = 0.05) Left tailed: p = 0.9606; alpha = 0.05 Right-tailed: p = 0.0394; alpha = 0.05 |

The data in Table 2 shows that the increase in white matter volume appears consistent with a hypothesis that ibogaine is triggering neurotrophic repair process.

Figure 7A:
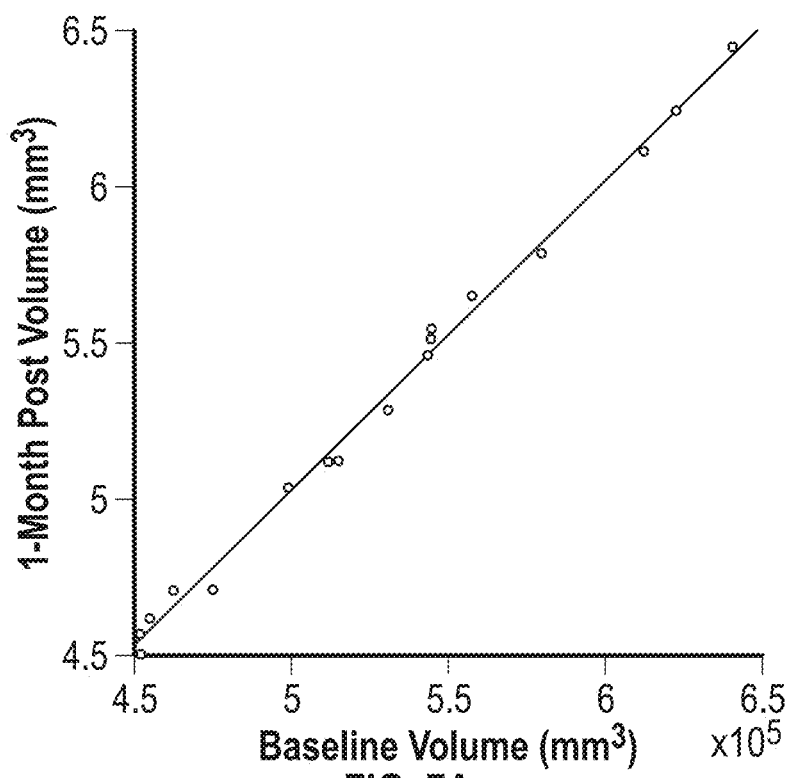
FIG. 7A is a graph of cerebral white matter volume, in $mm^3$, one month after treatment as a function of cerebral white matter volume, in $mm^3 \times 10^5$, at baseline (before treatment).
Figure 7B:
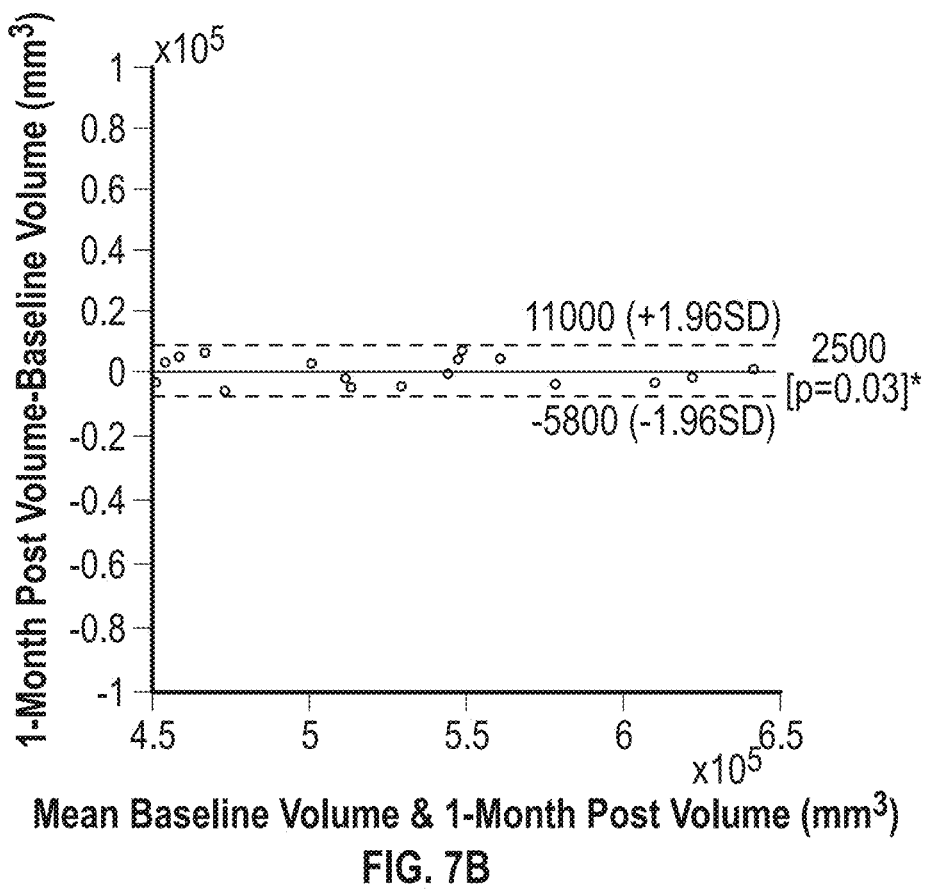
FIG. 7B is a graph of the change in cerebral white matter volume, in $mm^3$, taken as the difference in cerebral white matter volume one month after treatment and at baseline, as a function of cerebral white matter mean volume, in $mm^3 \times 10^5$, at baseline (before treatment) and one month after treatment.

FIG. 7A is a graph of cerebral white matter volume, in mm$^3$, one month after treatment as a function of cerebral white matter volume, in mm$^3 \times 10^5$, at baseline (before treatment). FIG. 7B is a graph of the change in cerebral white matter volume, in mm$^3$, taken as the difference in cerebral white matter volume one-month after treatment and at baseline, as a function of cerebral white matter mean volume, in mm$^3 \times 10^5$, at baseline (before treatment) and one month after treatment. The Bland-Altman plot is often used in test-retest reliability analyses, where the X-axis is the mean of test and re-test; here, the x-axis is the mean of baseline and 1-month post treatment and the Y-axis is the difference between the two. A mean increase in cerebral white matter volume of about 2500 mm$^3$ was observed (two-tailed, p=0.030; alpha=0.05; left-tailed, p=0.0150, alpha=0.05).

Figure 8A:
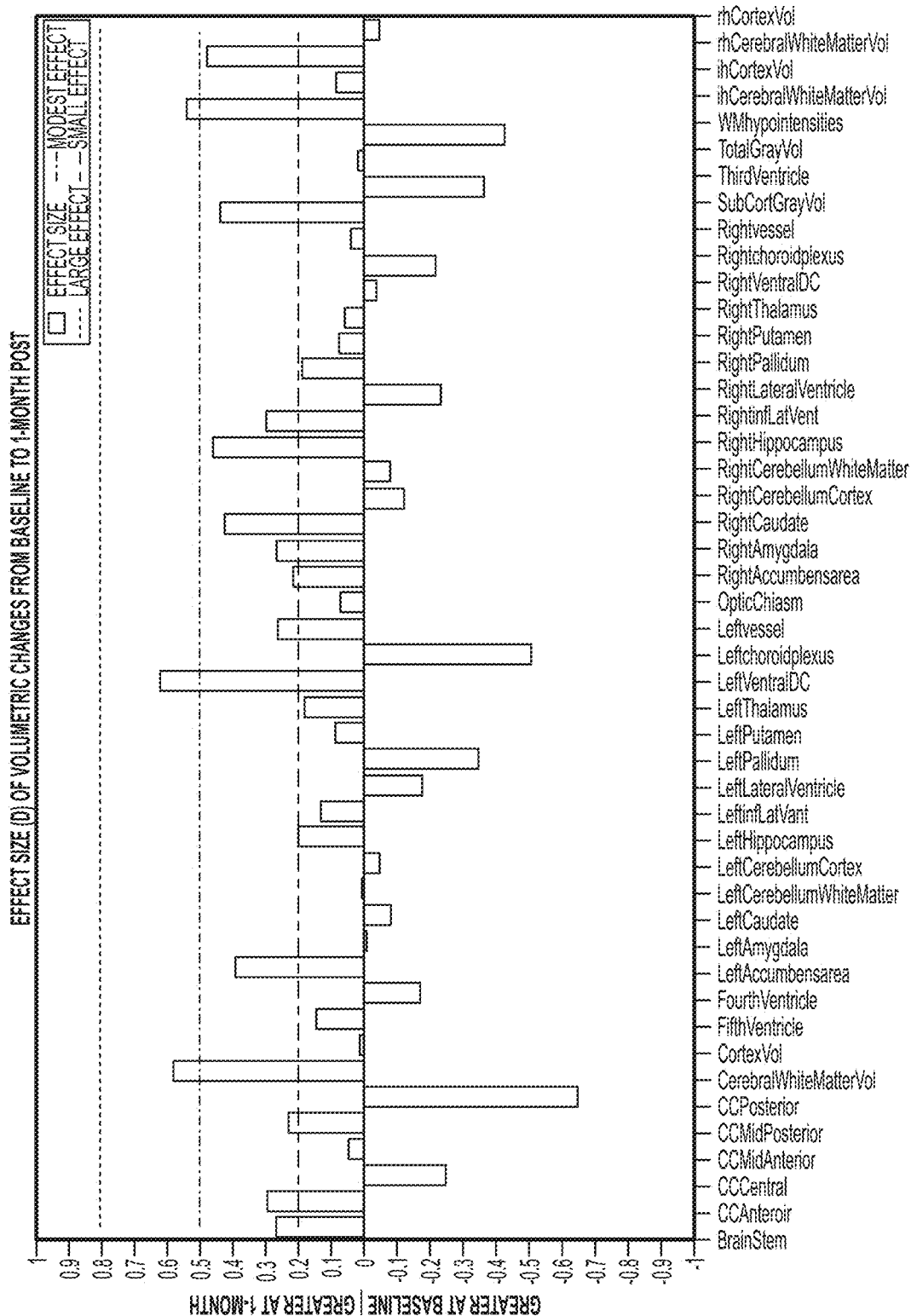
FIG. 8A is a bar graph showing the effect size of a change in cerebral white matter volume in 47 brain regions as indicated along the x-axis, one month after treatment.
Figure 8B:
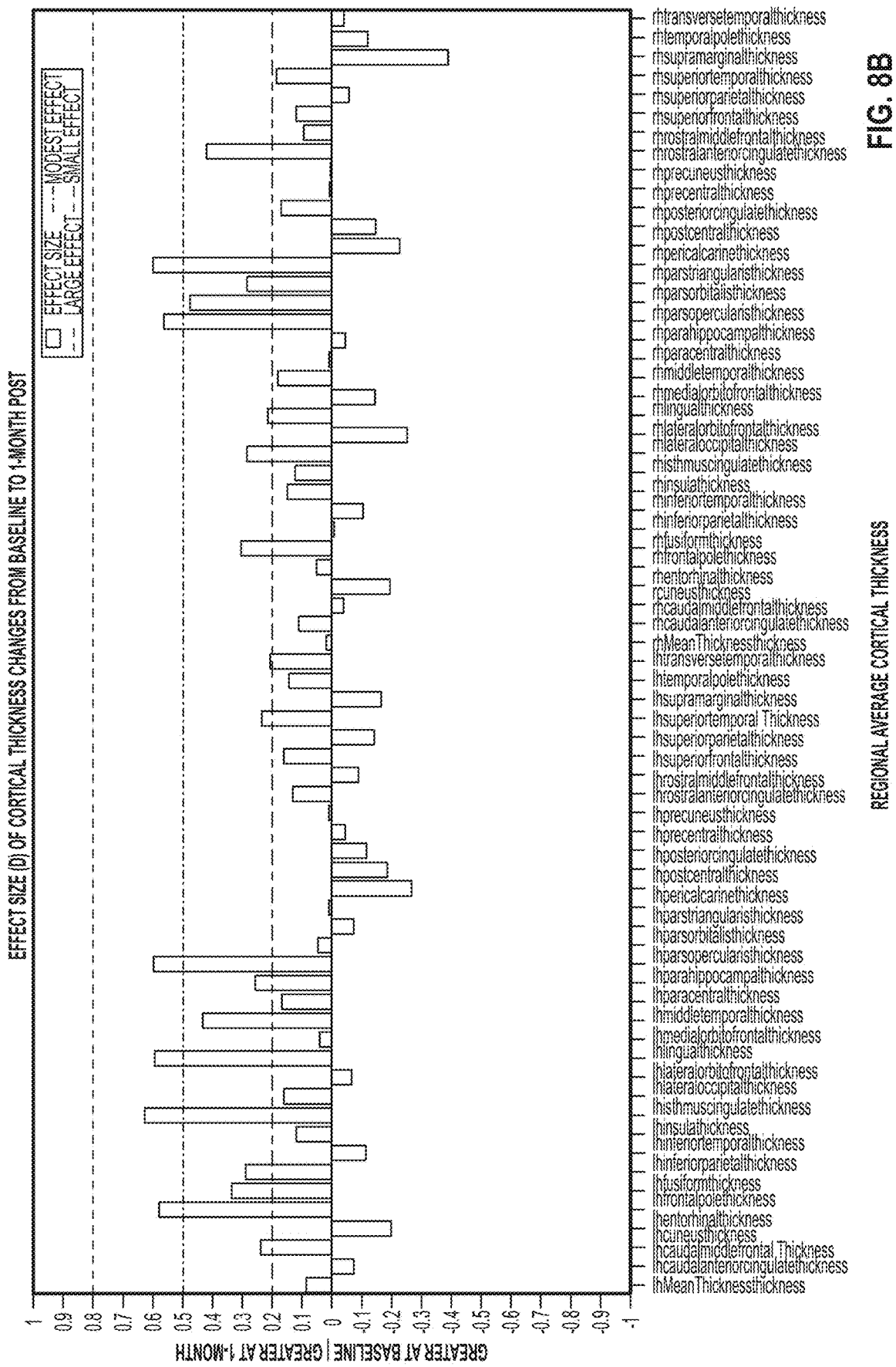
FIG. 8B is a bar graph showing the effect size of a cortical thickness change from baseline to one month after treatment for the brain regions indicated along the x-axis.

The fMRI images were also inspected to determine the difference in volume in regional areas of the brain from baseline to one month after treatment. FIG. 8A is a bar graph showing the effect size of a change in volume in 47 brain regions indicated along the x-axis. Increases in volume were observed in the cerebral white mater (left) and the left ventral DC. Decreases in volume were observed in the posterior corpus callosum and left choroid plexus. The fMRI images were also inspected for whole brain thickness at baseline and one month after treatment. Left hemisphere mean thickness one month after treatment showed no significant difference from baseline (two-tailed, p=0.7146, alpha=0.05); and right hemisphere mean thickness one month after treatment showed no significant difference from baseline (two-tailed, p=09452, alpha=0.05). FIG. 8B is a bar graph showing the effect size of a cortical thickness change for the brain regions indicated along the x-axis, from baseline to one month after treatment. Increases in cortical thickness one-month after treatment was observed in left entorhinal cortex, left-lateral-orbitofrontal pole, parahippocampal gyrus (bilaterally), left insular cortex, and right-pars triangularis (inferior frontal gyrus). The right-pars triangularis (inferior frontal gyrus) acts in response inhibition to suppress actions that are inappropriate in a given context and that interfere with goal-driven behavior. The right and left parahippocampal gyrus are involved in visuospatial processing, including scene perception, navigation, and emotional contextualization. The left orbitofrontal gyrus is involved in impulse control and reward valuation. The left insular cortex is associated with both the affective-perceptual and cognitive-evaluative forms of empathy, as well as awareness of hunger, pain and fatigue. The left entorhinal cortex is a widespread network hub for memory, navigation, and perception of time. The inspection of brain volume and thickness shows no apparent damage to the brain in the treated subjects.

In an embodiment, a method for slowing or reversing brain aging in a subject is provided. In an embodiment, the subject is a person a healthy individual or is a person with a neuropsychiatric disorder or is a person at risk of a neuropsychiatric disorder. In embodiments, the person has a TBI, a history of TBI, or is a risk of a TBI, or has a TBI and PTSD. The method comprises treating the subject with an *iboga* alkaloid in combination with a cardioprotective agent, as described herein. Neuroimaging data can be used to monitor and/or evaluate treatment. In an embodiment, the neuroimaging data is used to determine a predicted brain age that is compared with the subject's chronological age. Neuroimaging-derived age predictions have been explored in the context of different brain diseases (Cole, et al., *NeuroImage*. 163:115-124 (2017): Cole, et al., *Trends in Neurosciences*. 40 (12): 681 (2017))). By training models on healthy individuals, brain-based predictions of age can be made in independent clinical samples. If brain-predicted age' is greater than an individual's chronological age, this is thought to reflect some aberrant accumulation of age-related changes to the brain (Id.).

Figure 9A:
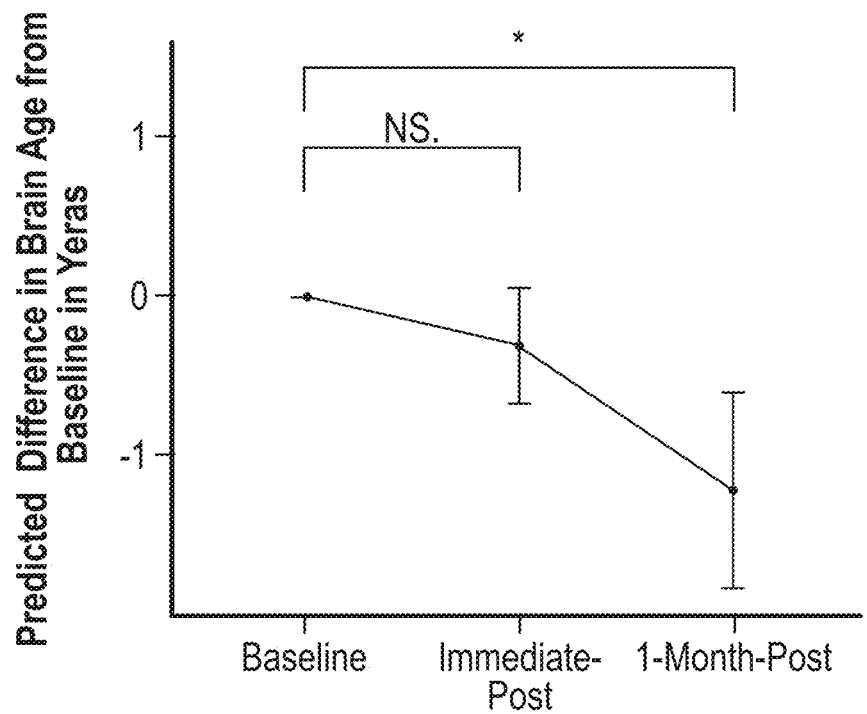
FIG. 9A shows the difference in predicted brain age from baseline, in years, for the subjects in the study of Example 1 at baseline, 4 days after treatment and one month after treatment.
Figure 9B:
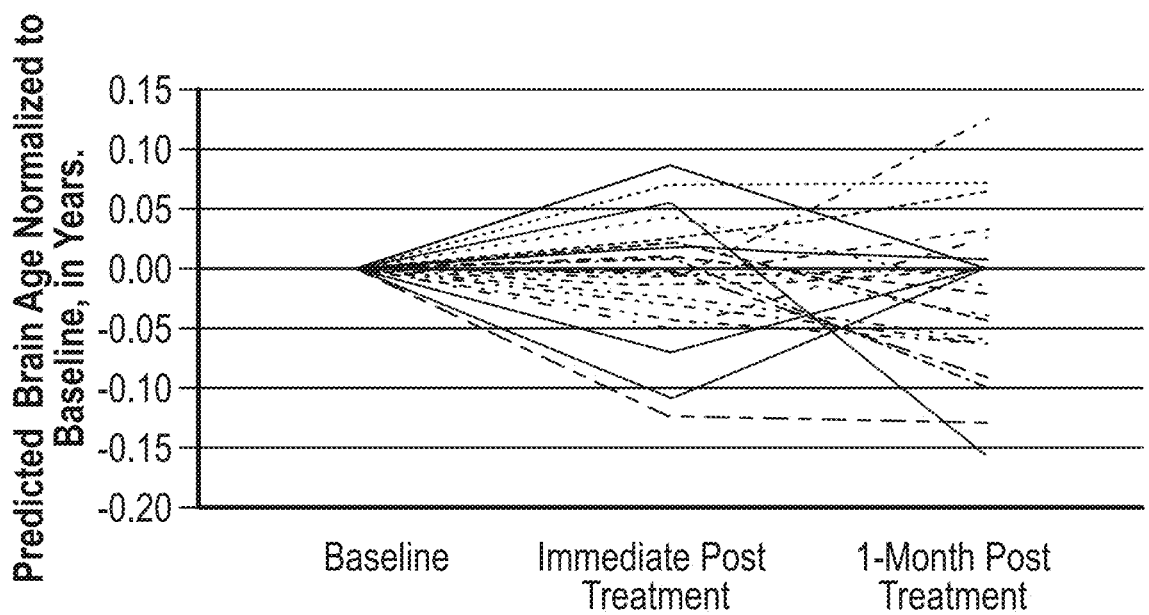
FIG. 9B shows the individual predicted brain age trajectories, normalized to baseline, in years, at baseline (v2), 4 days after treatment (v3) and one month after treatment (v4).

It has been reported that the long-term effects of traumatic brain injury (TBI) can resemble those observed in normal ageing, suggesting that TBI may accelerate the ageing process (Cole, et al., *Annals of Neurology*, 77 (4): 571 (2015)). A predictive model of normal aging defined using machine learning in healthy individuals, based on magnetic resonance imaging-derived estimates of gray matter and white matter (Id.) was applied to the MRI images from the subjects enrolled in the study of Example 1. FIG. 9A shows the difference in predicted brain age from baseline, in years, for the subjects in the study of Example 1 at baseline, four days after treatment and one month after treatment. There was a significant reversal of brain age from baseline to one month after treatment. The mean decrease in brain age was 1.3 years (corrected p=0.03). FIG. 9B shows the individual brain age trajectories, normalized to baseline, in years, at baseline (v2), 4 days after treatment (v3) and one month after treatment (v4). While the effects of ibogaine on brain aging are complex, a majority of the individual trajectories trend to a decrease in brain age after treatment.

Figure 9C:
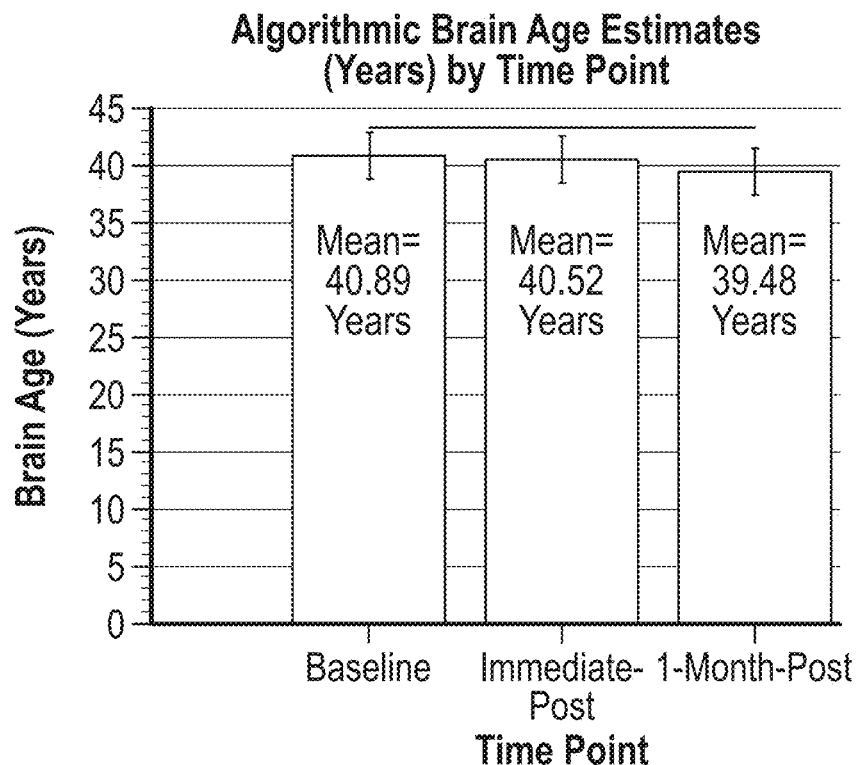
FIG. 9C is a bar graph showing algorithm brain age, in years, for 24 of the subjects in the study of Example 1 prior to treatment (baseline), one week after treatment and one month after treatment.

FIG. 9C is a bar graph showing algorithm brain age, in years, for 24 of the subjects in the study of Example 1 prior to ibogaine treatment (baseline), one week after treatment and one month after treatment. At baseline, the brain age estimate for the 24 subjects was 40.89 years. About one week after treatment with ibogaine, the brain age estimate for the 24 subjects was 40.52 years, and one month after treatment, the brain age estimate was 39.48 years. The data is also presented in Tables 3A and 3B. The average decrease in brain age from baseline one month after treatment was 1.4 years. When baseline brain age is contrasted against 1 week post and 1 month post treatment together, there is a significant linear trend for 1 week post and 1 month post to exhibit lower brain ages relative to baseline (Table 3B). When 1 month post treatment is contrasted against baseline and 1 week post treatment, there is a significant linear trend for 1 month post treatment to exhibit lower brain ages relative to both baseline and 1 week post.

TABLE 3A

| Contrast | Mean Difference (Years) | SE | N | t-stat | p-val | p-adj | Cohen's d |
|---|---|---|---|---|---|---|---|
| Immediate post (~1 wk) - baseline | -0.3764 | 0.364 | 24 | 1.04 | 0.311 | 0.311 | -0.2114 |
| 1-mo. post - baseline | -1.408 | 0.468 | 24 | 3.006 | 0.006* | 0.019* | -0.6137 |
| 1 wk post - 1 mo. post | -1.031 | 0.445 | 24 | 2.32 | 0.030* | 0.089 | -0.4729 |

TABLE 3B

| Contrast | Weights | Sig | Estimate (years) | 95% lower | 95% upper |
|---|---|---|---|---|---|
| Baseline vs. 1 wk and 1 mo. | 1-.5-.5 | 0.019 | 0.892 | 0.157 | 1.627 |
| Baseline & 1 wk. vs 1 mo. | .5-.5-1 | 0.008 | 1.220 | 0.352 | 2.087 |

Figure 9D:
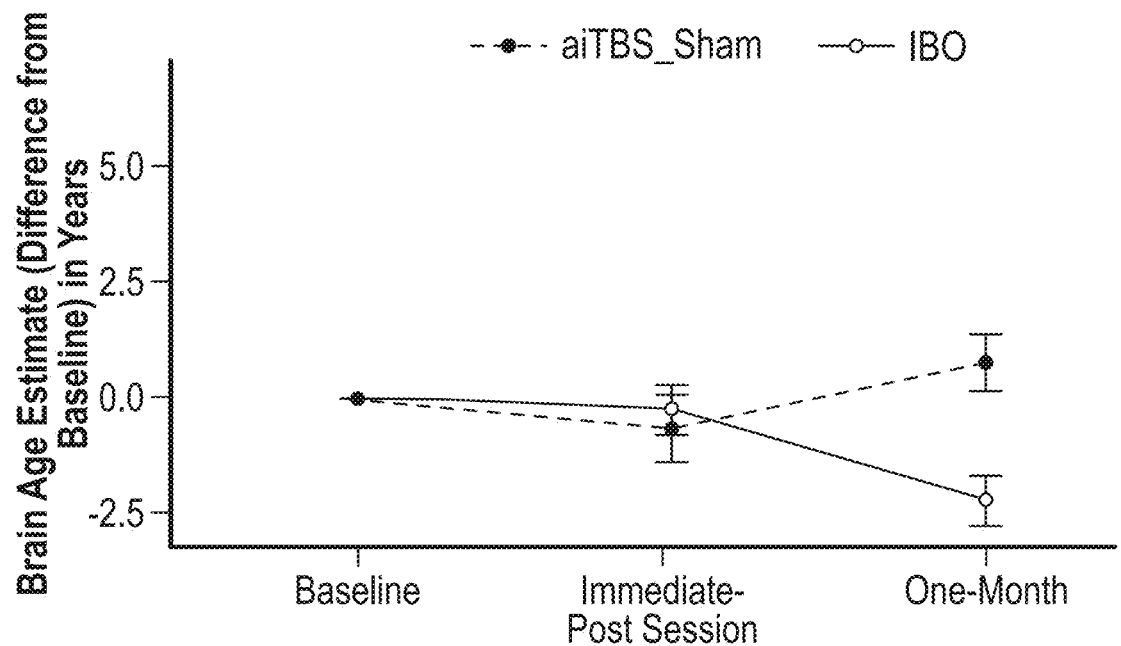
FIG. 9D is a graph at baseline, and 1-week and 1-month after treatment with ibogaine and a cardioprotective agent (open circles, solid line) and 1-week and 1-month after treatment with a transcranial magnetic stimulation technique, accelerated intermittent theta burst stimulation (aiTBS, solid circles, dashed line) of brain age estimate (difference from baseline), in years, for study participants

Results showing the effect of ibogaine treatment on brain age compared to transcranial magnetic stimulation is shown in FIG. 9D. FIG. 9D is a graph of brain age estimate (difference from baseline), in years, at baseline, and 1-week and 1-month after treatment with ibogaine and a cardioprotective agent (open circles, solid line) and 1-week and 1-month after treatment with accelerated intermittent theta burst stimulation (aiTBS, (solid circles, dashed line). Treatment with an *iboga* alkaloid provided a reducing in estimated brain age one-month post treatment compared to aiTBS.

Figure 10A:
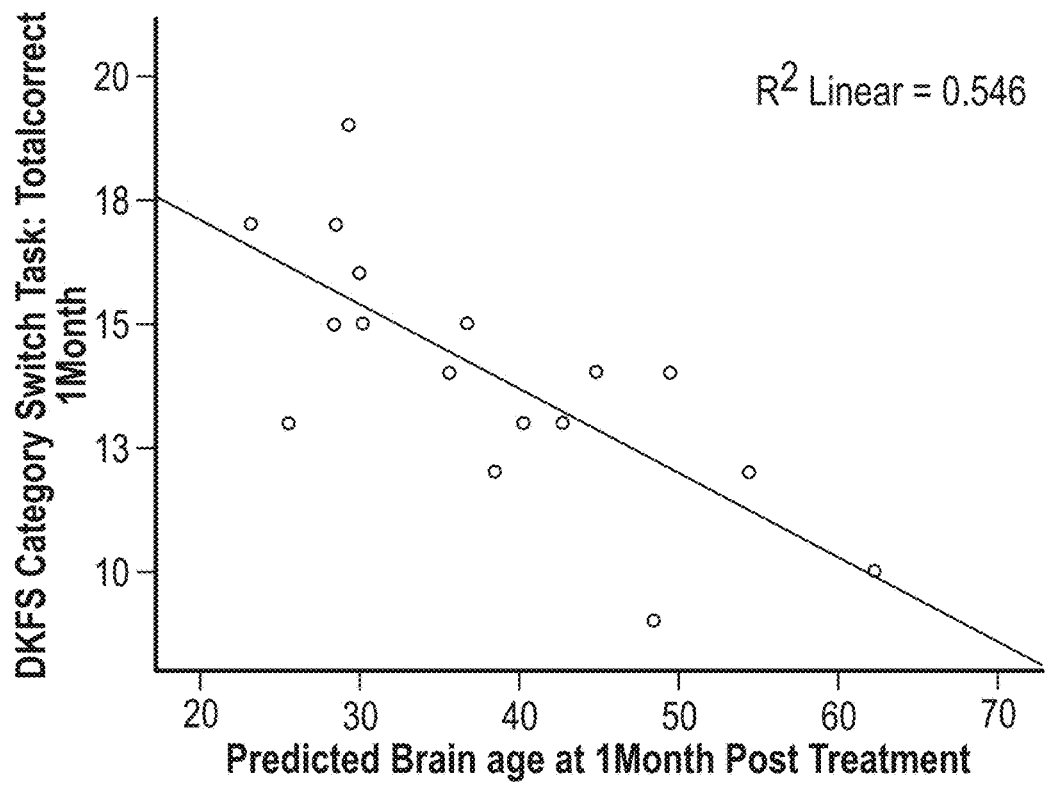
FIG. 10A is a graph of score on the Delis-Kaplan Executive Function System (DKFS) Category Switching Task for individuals one month after treatment as a function of predicted brain age, in years, one month after treatment.
Figure 10B:
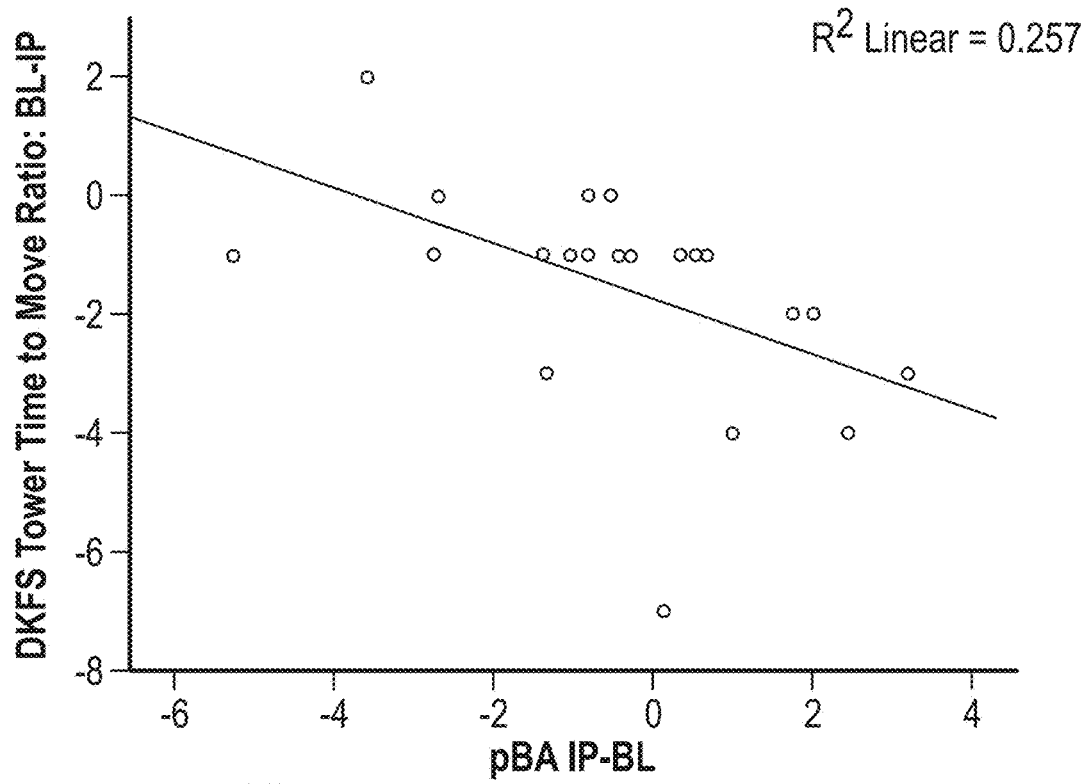
FIG. 10B is a graph of the difference between time per move on the Delis-Kaplan Executive Function System Tower Test between one month after treatment and baseline, as a function of difference between predicted brain age one month after treatment and baseline, in years.

The predicted brain age one month after treatment was predictive of an individual's score on a test of executive function (p=0.001, beta=−0.739), as seen in FIG. 10A. This correlation persisted even when chronological age was controlled for (p=0.008, beta=−0.660). The difference between predicted brain age one month after treatment and baseline was predictive of the difference between time per move on the Delis-Kaplan Executive Function System Tower Test between one month after treatment and baseline, as seen in FIG. 10B. Participants whose brain age became younger from baseline to one month post treatment needed less time on the test from baseline to one month post treatment (p=0.014, beta=−0.507). Controlling for chronological age removed this effect, but it still had a higher beta than chronological age.

Figure 10C:
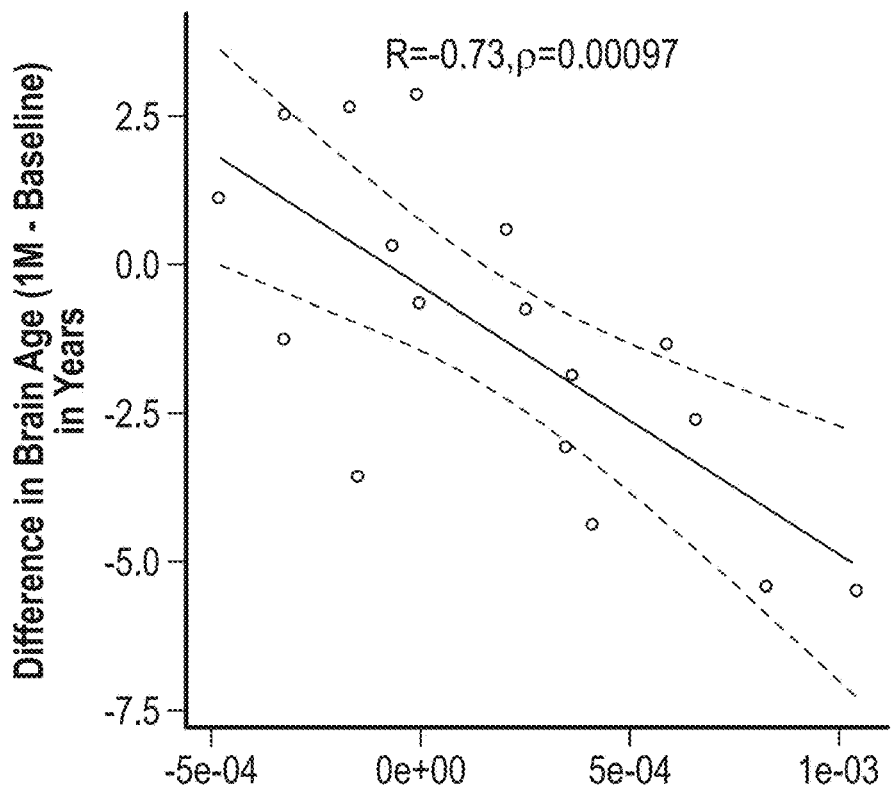
FIG. 10C is a graph of difference in predicted brain age one month after treatment relative to baseline, in years, in subcortical (thalamus, caudate, putamen, hippocampus, amygdala, accumbens and ventral DC) grey matter volume one month after treatment relative to baseline.
Figure 10D:
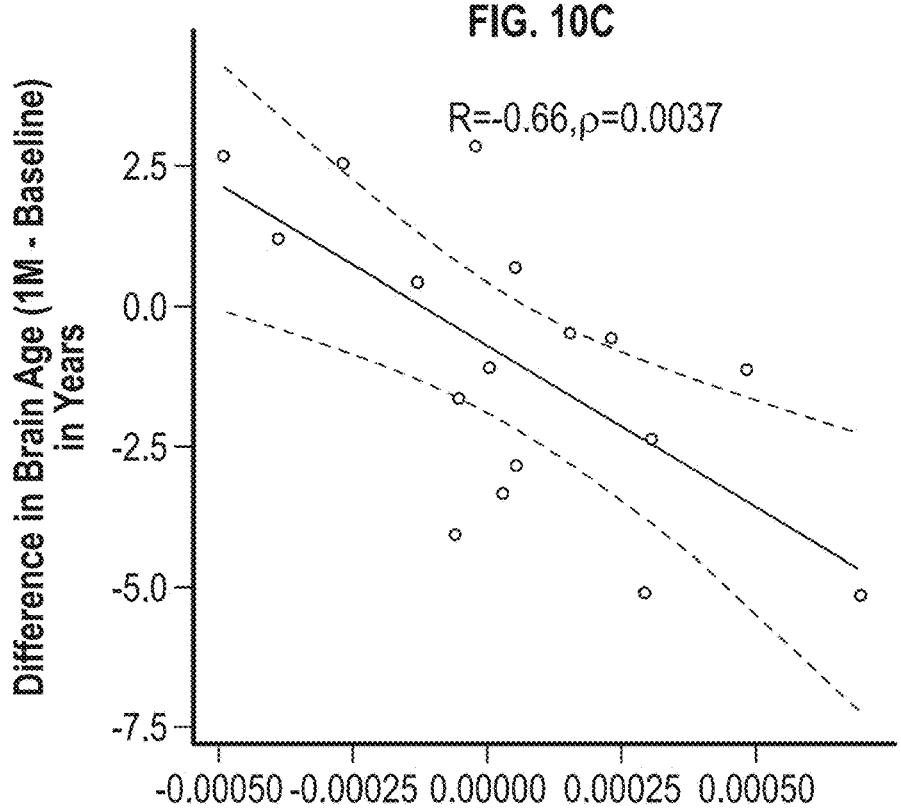
FIG. 10D is a graph of difference in predicted brain age one month after treatment relative to baseline, in years, in brain stem volume one month after treatment relative to baseline.

FIGS. 10C-10D show the volumetric contributions to brain age change in the subjects treated with ibogaine, where FIG. 10C shows the difference in brain age one month after treatment relative to baseline, in years, in subcortical grey matter volume one month after treatment relative to baseline. The subcortical volume combined the thalamus, caudate, putamen, hippocampus, amygdala, accumbens and ventral DC. FIG. 10D shows the difference in brain age one month after treatment relative to baseline, in years, in brain stem volume one month after treatment relative to baseline.

Accordingly, a method to slow brain aging or to reverse brain aging is contemplated. The method comprises administering to a subject an *iboga* alkaloid, such as ibogaine, as described herein. In an embodiment, the method further comprises performing an imaging technique on the subject after treatment, to assess effect of the *iboga* alkaloid on the brain. In an embodiment, the *iboga* alkaloid is ibogaine. In an embodiment, ibogaine is administered at a dose of between 2-50 mg/kg. In an embodiment, the *iboga* alkaloid is administered when the subject is under the care of a medical practitioner and/or a psychotherapist. In an embodiment, after a first administration of the *iboga* alkaloid, the subject rests for 1-7 days and a structural MRI is performed during the rest period or after the rest period. The MRI is analyzed to assess brain age. In an embodiment, the method further comprises administering a cardioprotective agent, before, during and/or after the *iboga* alkaloid.

In embodiments, a method of treatment to slow or reverse brain aging comprises the steps of performing a screening of the subject to gather medical and/or psychological information: optionally performing a structural MRI and analyzing the MRI with an algorithm to estimate brain age: administering or instructing to administer an *iboga* alkaloid to the subject: allowing for a period of rest, recovery and/or integration: optionally performing a structural MRI and analyzing the MRI with an algorithm to estimate brain age; and evaluating the subject after the *iboga* alkaloid treatment. It will be appreciated that the method is not limited to a scan via MRI, and that other imaging techniques may be suitable, such as an image from a computerized tomography (CT) scan, an image from a positron emission tomography (PET) scan, or an image from a single-positron emission computerized tomography (SPECT) scan. In an embodiment, MRIs before and/or after the *iboga* alkaloid treatment and analysis with a brain aging algorithm are performed on the subject. In embodiments, the *iboga* alkaloid is given over a 4-12 hour period and at a dose of 2-50) mg/kg, or at a dose as described herein. In an embodiment, the rest, recovery and/or integration period is from 1-3, 1-4, 1-5, 1-6 or 1-7 days. In an embodiment, the *iboga* alkaloid is ibogaine. In an embodiment, the method further comprises administering a cardioprotective agent, before, during and/or after the *iboga* alkaloid.

In an embodiment, a method for treating a neuropsychiatric condition in a subject is provided. The method comprises analyzing a first image data of a subject's brain using a brain age model to determine a first estimated brain age of the brain, where the first image data is captured prior to administration of an *iboga* alkaloid or salt thereof: administering, or instructing to administer, to the subject a cardioprotective agent in an amount effective to achieve a physiologic effect to reduce risk of long QT syndrome and the *iboga* alkaloid or salt thereof: analyzing a second image data of the subject's brain using the brain age model to determine a second estimated brain age of the brain, where the second image data is captured after administration of the *iboga* alkaloid or salt thereof; and evaluating or verifying treatment efficacy based on the first and second estimate brain ages. In an embodiment, when the first estimated brain age is greater than the second estimated brain age treatment efficacy is verified. The image data, in embodiments, is obtained from an MRI scan, a CT scan, a PET scan, a SPECT scan, and the like.

In one embodiment, verifying treatment efficacy comprises verifying a previously administered dose of *iboga* alkaloid or salt thereof is a correct dosage amount for the subject. In one embodiment, verifying treatment efficacy comprises verifying a previously administered dose of *iboga* alkaloid or salt thereof is an incorrect dosage amount for the subject. In one embodiment, the method further comprises recommending an adjustment in the dosage amount, the route of administration, the drug administered, and/or the pharmaceutical formulation.

In one embodiment, the method further comprises administering, or instructing to administer, to the subject an additional dose of the cardioprotective agent in an amount effective to achieve a physiologic effect to reduce risk of long QT syndrome and the *iboga* alkaloid or salt thereof.

As can be appreciated from the data and Examples, methods for treating a neuropsychiatric condition in a subject, for improving brain health, and/or for slowing progression of brain aging or reversing brain aging are provided. The methods comprise administering, or instructing to administer, to a subject a cardioprotective agent in an amount effective to achieve a physiologic effect to reduce risk of long QT syndrome and an *iboga* alkaloid or salt thereof; and monitoring the subject by analyzing image data from a brain image. The image data is analyzed with a model to determine a predicted brain age. The predicted brain age is compared with the subject's chronological age, in years or in years and months, generally at the time of treatment. In embodiments, if the predicted brain age is different than the chronological age by a predetermined value, the method further comprises repeating the administering or instructing to administer. In one embodiment, the predetermined value difference between the predicted brain age and the greater is the predicted brain age greater than the chronological age by 1 year or more, 2 years or more, 3 years or more, 4 years or more, 5 years or more, 6 years or more, 7 years or more, 8 years or more, 9 years or more or 10 years or more. In an embodiment, the predicted brain age is greater than the chronological age by between about 1-10 years, 1-8 years, 1-6 years, 1-5 years, 1-4 years, 1-3 years, 1-2 years, 2-10 years, 2-8 years, 2-6 years, 2-5 years, 2-4 years, or 2-3 years.

In an embodiment, when the predicted brain age differs from the chronological age before treatment and/or after treatment, the method further comprises continuing to administer, or the instructing to administer, a second or further dose of the *iboga* alkaloid and cardioprotective agent. That is, the method further comprises repeating the administering or instructing to administer if the predicted brain age is greater than the chronological age. In one embodiment, the repeating the administering or instructing to administer is with the same *iboga* alkaloid and/or the same cardioprotective agent as the prior administering or instructing to administer. In an embodiment, repeating the administering or instructing to administer is at the same dose and/or the same route of administration and/or with the same *iboga* alkaloid and/or the same cardioprotective agent as the prior administering or instructing to administer. In an embodiment, the repeating the administering or instructing to administer is at a different dose and/or a different route of administration and/or with a different *iboga* alkaloid (or other drug) and/or a different cardioprotective agent as the prior administering or instructing to administer.

In an embodiment, when the predicted brain age differs from the chronological age before treatment and/or after treatment, the method further comprises recommending an alternative to the administering or instructing to administer, based on the monitoring of the subject and/or based on the analyzing image data.

For example, a subject with a neuropsychiatric condition or a subject at risk of cognitive decline due to a neuropsychiatric condition is treated with an *iboga* alkaloid and cardioprotective agent, as described herein. Before treatment and/or after treatment, image data of the subject's brain is analyzed with a brain prediction model to determine a predicted brain age. The predicted brain age is compared with the subject's chronological age. If the predicted brain age is (i) greater than the subject's chronological age or (ii) equal to or greater than a previously determined predicted brain age for the subject, a treatment protocol from these following options is recommended:
  (a) repeating the administering (or instructing to administer) the *iboga* alkaloid or salt thereof and/or cardioprotective agent.
  (b) waiting a period of time and repeating the monitoring by obtaining a brain scan, an image of a brain scan, or data from a brain scan image,
  (c) recommending or providing no further treatment with the *iboga* alkaloid, and
  (d) recommending or administering a therapy other than an *iboga* alkaloid In one embodiment, if the predicted brain age is (i) equal to or less than the subject's chronological age or (ii) less than a previously determined predicted brain age for the subject, a treatment protocol from these following options is recommended:
  (a) repeating the administering (or instructing to administer) the *iboga* alkaloid or salt thereof and/or cardioprotective agent,
  (b) waiting a period of time and repeating the monitoring by obtaining a brain scan, an image of a brain scan, or data from a brain scan image,
  (c) recommending or providing no further treatment with the *iboga* alkaloid, and
  (d) recommending or administering a therapy other than an *iboga* alkaloid.

In an embodiment, the period of time for waiting is 1 day, 3 days, 5 days, 1 week, 2 weeks, 1 month or 2 months.

As can be appreciated, repeating the step of monitoring the subject by analyzing data from a brain scan determines a post-treatment predicted brain age. The post-treatment predicted brain age is compared to the chronological age and/or to a previously determined predicted brain age. In embodiments, if the post-treatment predicted brain age is greater than the chronological age, treatment with the *iboga* alkaloid or salt thereof and a cardioprotective agent is repeated. The repeated treatment can be at the same or different dose of each agent or with a same or different cardioprotective agent or the same or different route of administration. In one embodiment, the method comprises repeating the administering or instructing to administer if the post-treatment predicted brain age is equal to or less than the precited brain age.

In one embodiment, the method comprises recommending an alternative to treatment with an *iboga* alkaloid or salt thereof if a post-treatment predicted brain age is equal to or greater than a prior determined predicted brain age. In one embodiment, the prior determined predicted brain age was determined prior to treatment with an *iboga* alkaloid or salt thereof. In an embodiment, the prior determined precited brain age is after one or more doses of an *iboga* alkaloid or salt thereof.

As can be appreciated from the data, the image data is obtained from an image obtain using magnetic resonance imaging (MRI), an image from a computerized tomography (CT) scan, an image from a positron emission tomography (PET) scan, or an image from a single-positron emission computerized tomography (SPECT) scan. In one embodiment, the MRI is a T1-weighted MRI image or a diffusion-weighted MRI (DWI). In one embodiment, the T1-weighted MRI image data is raw T1-weighted structural MRI image data. In one embodiment, the DWI is diffusion tensor imaging (DTI). The image data can be processed using voxel-based morphometry. In one embodiment, the voxel-based morphometry is applied to a brain tissue selected from gray matter and white matter. The image data can also be analyzed to obtain a measure of one or more of total intracranial volume, cortical thickness, surface area and subcortical volume.

Analysis of image data from a brain image using an algorithm or brain age prediction model can take the form any number of known models. For example, in one embodiment, the brain age model, also referred to herein as an algorithm, is a linear model or non-linear model. In one embodiment, the brain age model is a parametric model, a non-parametric model, or an ensemble learning model. In one embodiment, the brain age model is the brain age prediction model BrainAGE (Franke, K. et al., Frontiers in Neurology, 10(789): 1-26 (2019)). The algorithm, or model, can be a linear algorithm or non-linear algorithm a parametric algorithm, a non-parametric algorithm, or an ensemble learning algorithm, as detailed for example in Han, et al., *Sensors,* 22:8077 (2022).

In one embodiment, the subject is a healthy individual. In one embodiment, the subject has a known risk of cognitive decline or is at risk of a cognitive decline due to a neuropsychiatric condition. In one embodiment, the subject is at risk of a cognitive decline due to a genetic disorder. In one embodiment, the genetic disorder is presence of a gene variant or presence of a gene mutation. In one embodiment, the subject the genetic disorder is presence of a gene variant selected from apolipoprotein E-4 (ApoE4) gene, amyloid precursor protein (APP), presenilin 1 (PSEN1) and presenilin 2 (PSEN2). In one embodiment, the subject the genetic disorder is a mutation selected from a leucine rich repeat kinase 2 (LRRK2) mutation, a tau gene mutation, and a glucocerebrosidase (GBA) gene mutation.

In one embodiment, the subject is at risk of a cognitive decline due to a family history of cognitive decline or substance abuse disorder. In one embodiment, the subject the substance abuse disorder is alcohol abuse. In one embodiment, the subject the subject is diagnosed with mild cognitive impairment.

In one embodiment, the subject has a traumatic brain injury or has a history of one or more traumatic brain injuries. In one embodiment, the subject the subject has a post-traumatic stress disorder.

In an embodiment, the subject to be treated is a healthy subject. In an embodiment, the subject is one at risk of or diagnosed with Alzheimer's disease. In an embodiment, the subject is one at risk of or diagnosed with schizophrenia, multiple sclerosis, alcohol dependence, viral infection, depression, impulsivity or impulse-control disorder, cognitive impairment, excessive sleepiness, chronic low back pain, cigarette smoking, human immunodeficiency virus (HIV). TBI, long COVID-19 and/or obesity. In an embodiment, the subject has mild cognitive impairment. In an embodiment, an imaging technique is used to measure the neuroprotective consequences of ibogaine treatment. In an embodiment, the imaging technique is MRI and the image(s) are used to inform ibogaine dosing or re-dosing.

In an embodiment, brain aging refers to a set of processes which occur in an organism over time, most of which involve the accumulation of diverse and deleterious changes in cells and tissues that increase the likelihood of disease, dysfunction and/or death. Aging changes can be attributed to: (1) developmental and genetic defects. (2) the environment. (3) disease processes, and/or (4) to an inherent process, referred to as the aging process. In an embodiment, aging as used herein refers to a subject's biological age as opposed to chronological age. In an embodiment, the biological age is ascertained by a measure selected from telomere length, grip strength, gum health, lung function, HbA1C level, mean arterial pressure, white blood cell count, cell membrane viscosity, corneal endothelial thickness, cholesterol level, and/or cytomegalovirus optical density. In another embodiment, brain aging is measured with a macroscopic method (e.g., enlarged ventricles, cortical thinning, white matter hyperintensities), a cellular method (e.g. synaptic pruning, axonal loss, mitochondrial changes, alterations to glial cell numbers), a molecular method (altered gene expression, disrupted calcium signaling, epigenetic changes) and/or a behavioral method (cognitive decline, reduced well-being or mood).

MR perfusion techniques measure the quantity of blood that flows through a particular volume of brain tissue, i.e., a voxel, rather than a particular mass. Pseudo-continuous arterial spin labeling (pcASL) MRI is a non-invasive tool to measure cerebral blood flow: Cerebral blood flow is a physiological parameter reflecting the rate of blood supply to the brain and is typically written in units of mL of blood per 100 grams tissue per minute (mL/100 g/min). Cerebral blood flow plays a role in the maintenance of neuronal integrity, and is kept essentially constant in a normal brain over the wide range of systemic blood pressures it encounters. Cerebral blood flow has been shown to be a sensitive marker for cerebrovascular diseases such as stroke and vascular dementia. Changes in perfusion often precede observable structural changes such as atrophy in neurodegenerative diseases.

Arterial spin labeling (ASL) MR was used to measure cerebral blood flow in some of the subjects of the study enrolled in the study of Example 1. As described in Example 3, pseudo-continuous ASL (pcASL) was performed on the subject at baseline, about 1 week after treatment, and one-month after treatment. The subjects in Example 3 were treated with ibogaine in combination with a cardioprotective agent as detailed in Example 1. A first metric of interest was change in net quantity (mL/100 g tissue/min) of blood entering different regions of the brain. Images of the left posterior orbital gyrus, left anterior insula, left and right cerebral white matter at baseline and 1-week post treatment (images not shown) were analyzed and compared. Images of the right anterior cingulate gyrus, right middle cingulate gyrus, right superior frontal gyrus medial segment, right posterior orbital gyrus, right cerebral white matter, right and left insula, and right planum polare at baseline and one-month post treatment (images not shown) were analyzed and compared. A paired t-test across 3 time points-baseline (pre-treatment), 1 week post-treatment, and 1 month post-treatment—was employed. No significant changes were seen in absolute cerebral blood flow after treatment with ibogaine ($p<0.001$).

A second metric of interest was regression between change in clinical scores versus change in relative cerebral blood perfusion from baseline to one-month post treatment. Multiple regression with clinical scores at baseline and one-month post treatment was used. Images of the right anterior and middle cingulate gyrus, a component of the limbic system, were obtained (images not shown). The anterior cingulate cortex connects to the emotional limbic system and the cognitive prefrontal cortex. The middle cingulate gyrus is thought to play a role in social behavior and is engaged when monitoring the outcomes of decisions during social interactions. Results are shown in FIGS. 11A-11F.

Figure 11A:
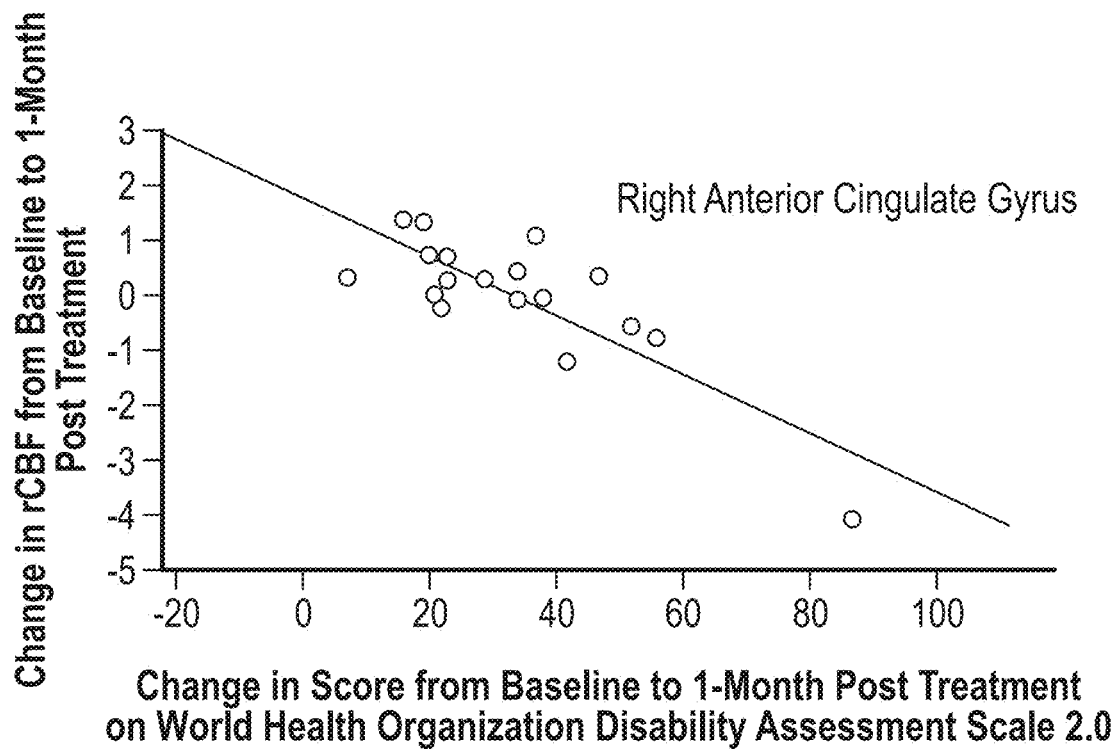
FIG. 11A is a graph showing the correlation between change in relative cerebral blood perfusion (rCBF) and change in score on World Health Organization Disability Assessment Scale 2.0 (WHODAS 2.0) in the right anterior cingulate gyrus [MINI coordinates 12, 40, 18] from baseline to one-month post ibogaine treatment.

FIG. 11A shows the correlation between change in relative cerebral blood perfusion in the right anterior cingulate gyrus and change in WHODAS 2.0 score (changes from baseline to one-month post treatment). An increase in relative blood flow in the right anterior cingulate gyrus one month after treatment predicts greater improvement in the disability score.

Figure 11B:
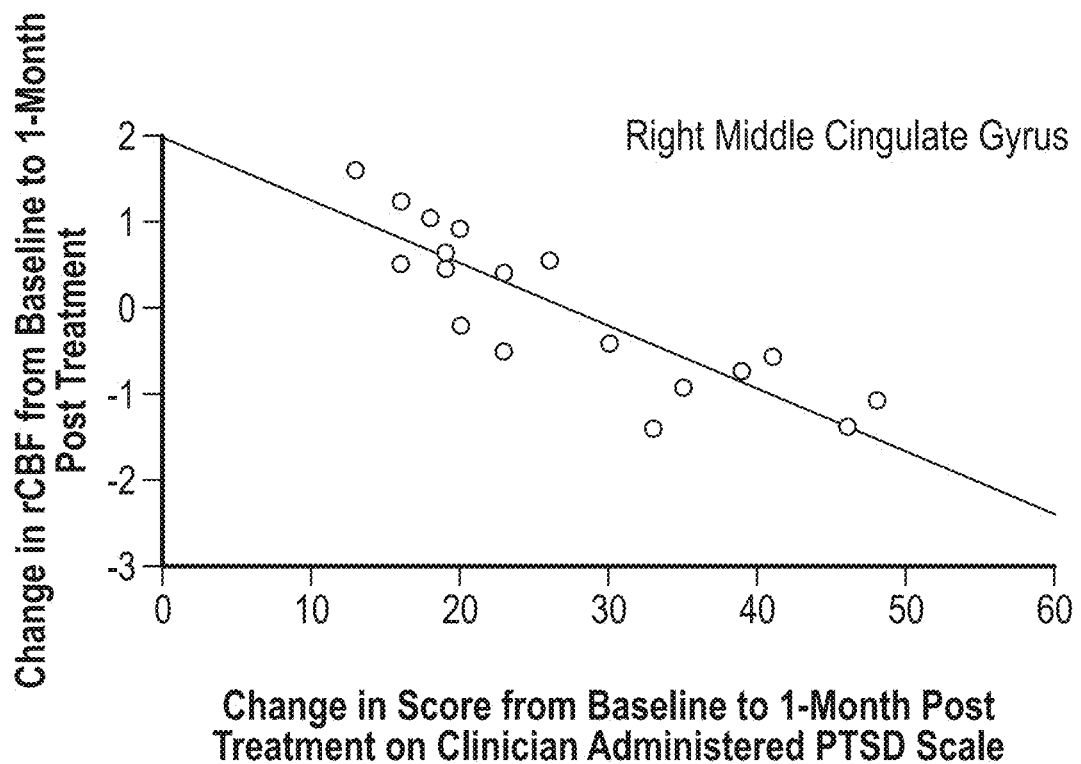
FIG. 11B is a graph showing the correlation between change in cerebral blood flow and change in score on the Clinician-administered PTSD Scale for DSM-5 (CAPS-5) in the right middle cingulate gyrus [MINI coordinates 6, 8, 38], the change from baseline to one-month post treatment.

FIG. 11B is a graph showing the correlation between change in relative cerebral blood perfusion and change in score on the CAPS-5 (a clinician-administered PTSD scale) in the right middle cingulate gyrus, the change from baseline to one-month post treatment. An increase in relative blood flow in the right middle cingulate gyrus one month after treatment predicts greater improvement in the PTSD score.

Figure 11C:
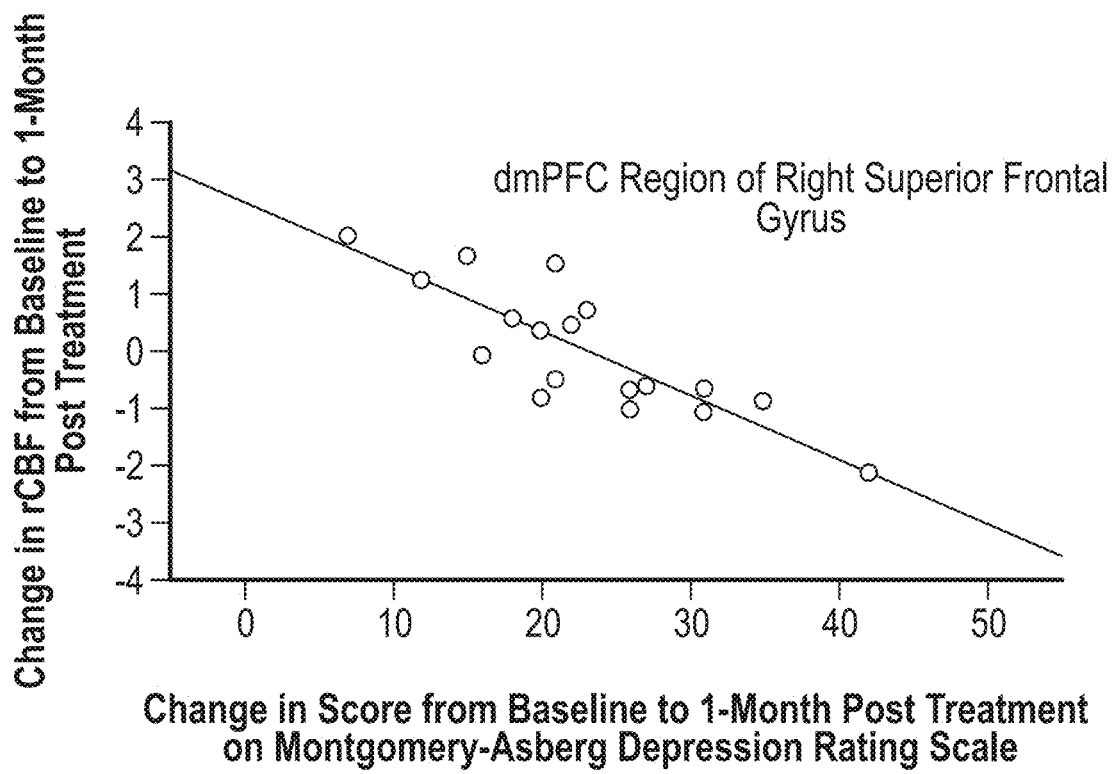
FIG. 11C is a graph showing the correlation between change in relative cerebral blood perfusion (rCBF) and change in score on the Montgomery-Asberg Depression Rating Scale (MADRS) in the dorsomedial prefrontal cortex (dmPFC) region within the right superior frontal gyrus [MINI coordinates 4, 42, 34], the change from baseline to one-month post treatment.

FIG. 11C is a graph showing the correlation between change in relative cerebral blood perfusion and change in score on the Montgomery-Asberg Depression Rating Scale (MADRS) in the dorsomedial prefrontal cortex (dmPFC) region within the right superior frontal gyrus, the change from baseline to one-month post treatment. The dmPFC plays a role in self-awareness, estimating and executing behavioral responses in a social context. An increase in relative blood flow in a small cluster of the right dmPFC at one month after treatment predicts greater improvement in the depression score.

Figure 11D:
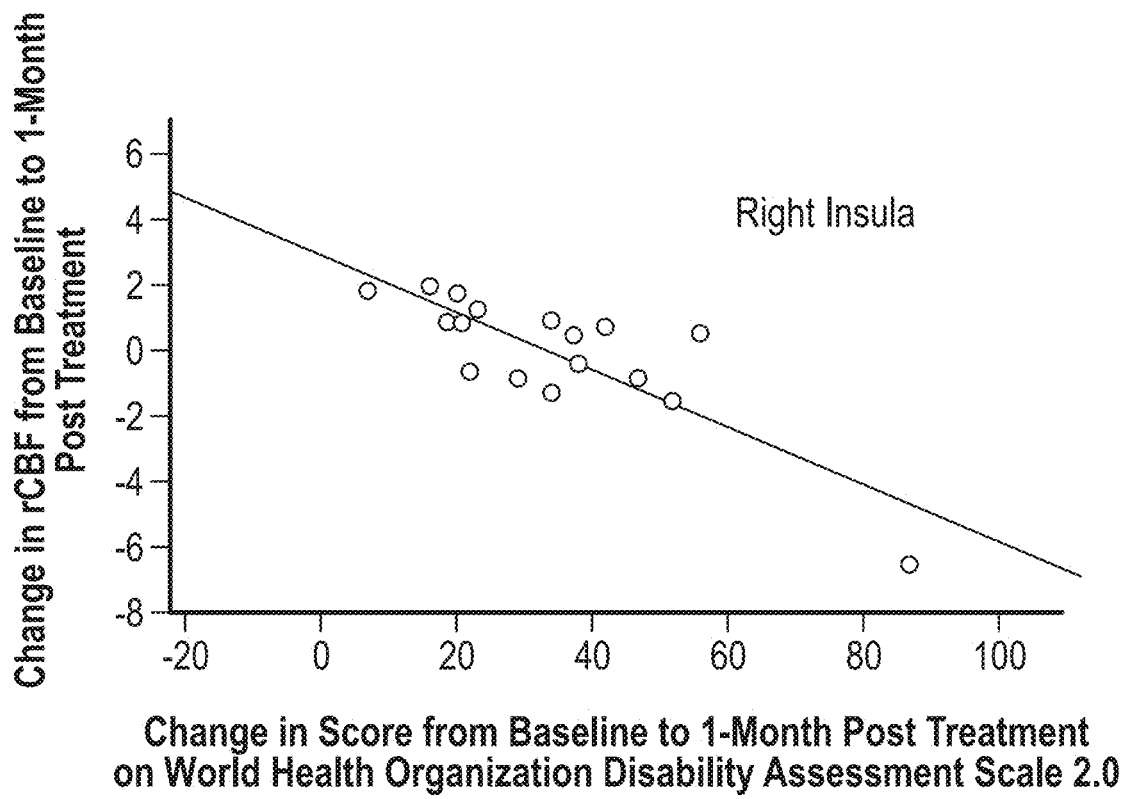
FIG. 11D is a graph showing the correlation between change in relative cerebral blood perfusion (rCBF) and change in score on WHODAS 2.0 in the right insula [MINI coordinates 42, 4, −8], from baseline to one-month post treatment.

FIG. 11D shows the correlation between change in relative cerebral blood perfusion in the right insula and change in WHODAS 2.0 score (changes from baseline to one-month post treatment). The insula is associated with the affective-perceptual and cognitive-evaluative forms of empathy. Convergent point of interoceptive processing, or sense of inner self. It may be the cornerstone of our overall awareness. The correlation in FIG. 21D shows that an increase in relative blood flow in the right insula one month after treatment predicts greater improvement in the disability score.

Figure 11E:
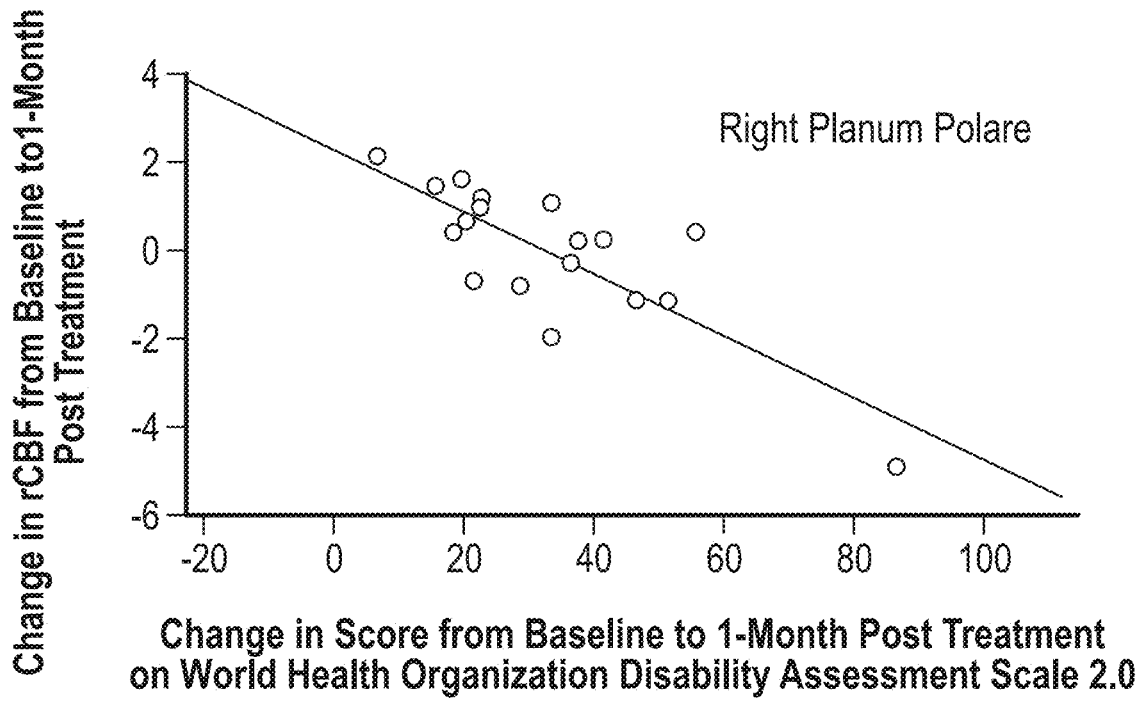
FIG. 11E is a graph showing the correlation between change in relative cerebral blood perfusion (rCBF) and change in score on WHODAS 2.0 in the right planum polare [MINI coordinates 46, 4, −10], from baseline to one-month post treatment.

FIG. 11E shows the correlation between change in relative cerebral blood perfusion and change in score on WHO- DAS 2.0 in the right planum polare, from baseline to one-month post treatment. The right planum polare is a part of the superior temporal gyrus and is involved in auditory processing and receptive language. An increase in relative blood flow in the right planum polare one month after treatment predicts greater improvement in the disability score.

Figure 11F:
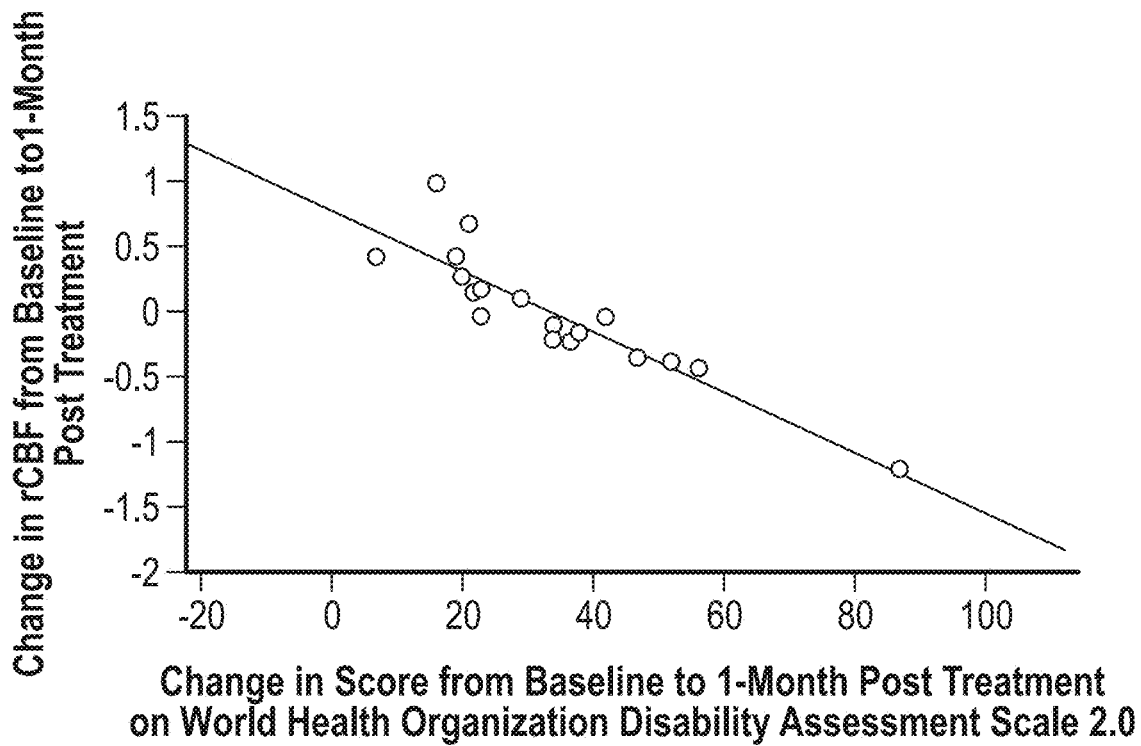
FIG. 11F is a graph showing the correlation between change in relative cerebral blood perfusion (rCBF) and change in score on WHODAS 2.0 in the right posterior orbital gyrus [MINI coordinates 34, 20, −14], from baseline to one-month post treatment.

FIG. 11F shows the correlation between change in relative cerebral blood perfusion in the right posterior orbital gyrus and change in WHODAS 2.0 score (changes from baseline to one-month post treatment). The right posterior orbital gyrus receives inputs from the limbic regions of the brain and has a role in processing olfactory and gustatory inputs and in integration of emotions and memories associated with sensory experiences. An increase in relative blood flow in the right posterior orbital gyrus one month after treatment predicts greater improvement in the disability score.

Figure 11G:
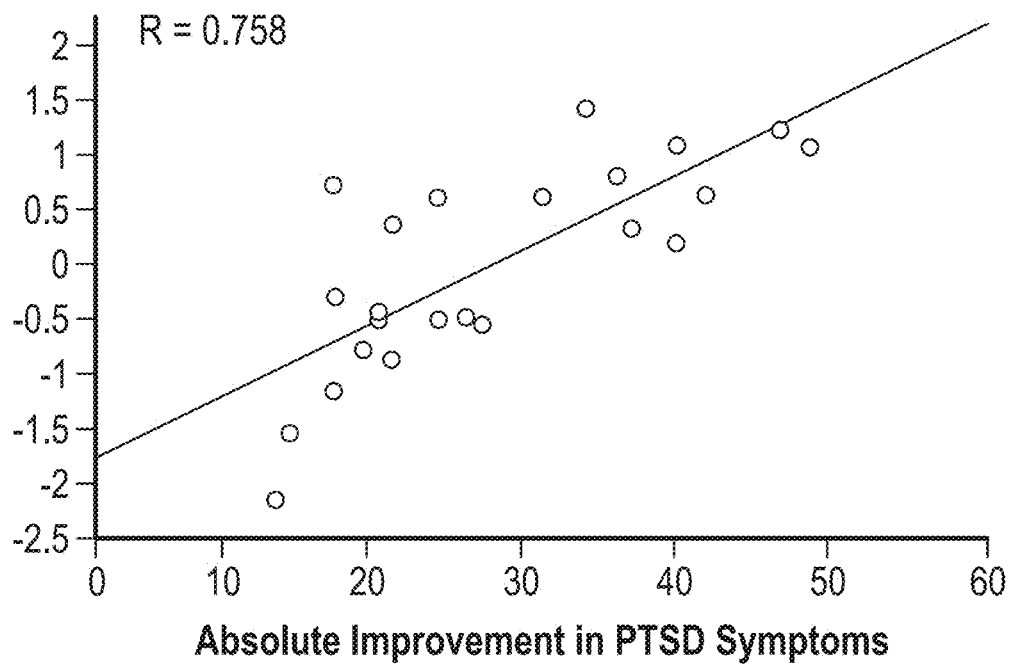
FIG. 11G shows the change in relative cerebral blood flow in the right middle cingulate gyrus one month after treatment as a function of absolute improvement in PTSD symptoms using the CAPS assessment.
Figure 11H:
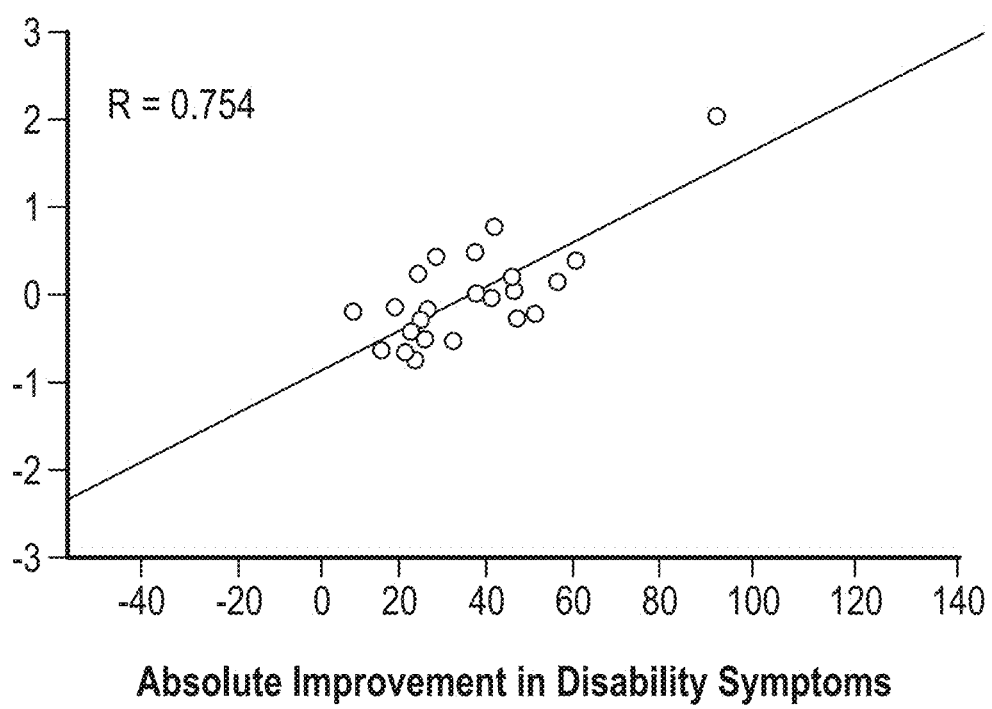
FIG. 11H shows the change in relative cerebral blood flow in the dorsomedial prefrontal cortex brain region one month after treatment as a function of absolute improvement in disability symptoms using the WHODAS assessment.
Figure 11I:
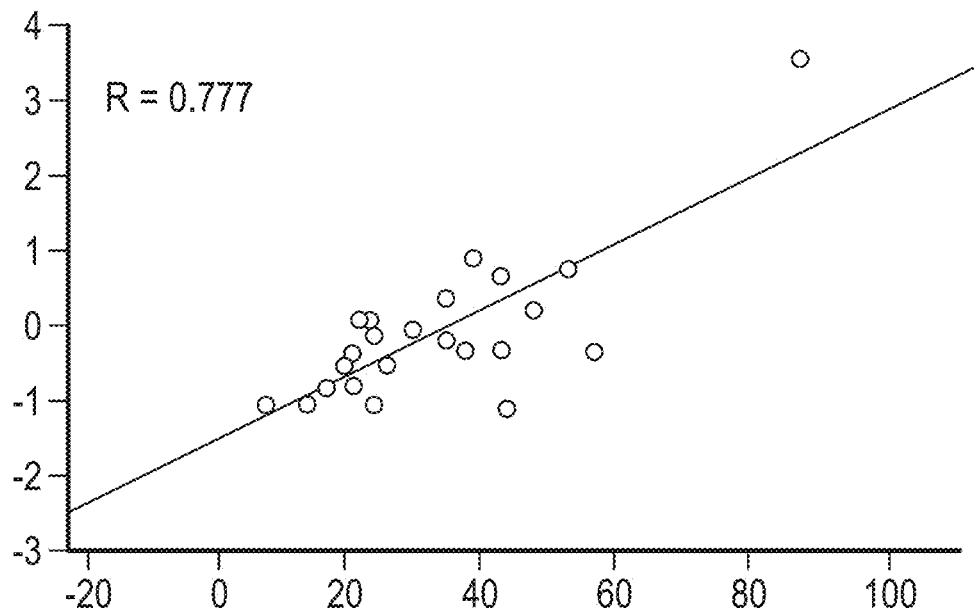
FIG. 11I shows the change in relative cerebral blood flow in the right anterior insula one month after treatment as a function of absolute improvement in disability symptoms using the WHODAS assessment.
Figure 11J:
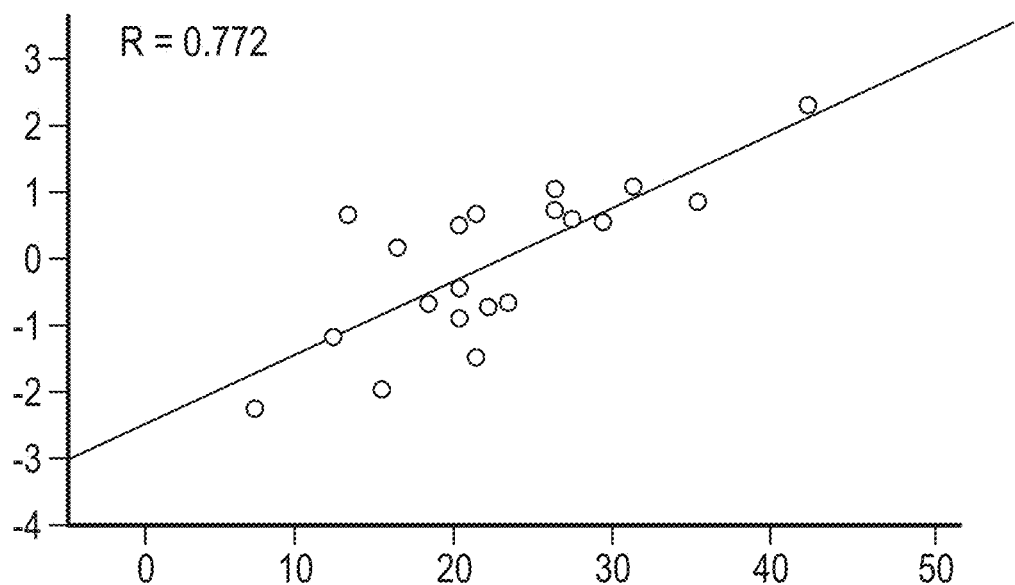
FIG. 11J shows the change in relative cerebral blood flow in the dorsomedial prefrontal cortex brain region one month after treatment as a function of absolute improvement in disability symptoms using the MADRAS assessment.

In summary, from the BOLD data, resting state functional connectivity shows reorganization of 22 functional connection pairs in the brain networks within a few days after treatment with ibogaine. This result persisted to the one-month post treatment check in. The ASL data shows relative increases in blood flow post treatment with ibogaine with a change in distribution of blood to different regions of the brain relative to base line blood flow measured prior to ibogaine treatment. Alterations of functional connectivity pairs in the brain network are caused by ibogaine treatment, with a persistent post treatment effect. FIGS. 11G-11J are graphs showing this effect, where the change in relative cerebral blood flow in certain brain regions is correlated with the absolute improvement in the indicated clinical assessment. FIG. 11G shows the change in relative cerebral blood flow in the right middle cingulate gyrus one month after treatment as a function of absolute improvement in PTSD symptoms using the CAPS assessment. FIG. 11H shows the change in relative cerebral blood flow in the dorsomedial prefrontal cortex brain region one month after treatment as a function of absolute improvement in disability symptoms using the WHODAS assessment. FIG. 11I shows the change in relative cerebral blood flow in the right anterior insula one month after treatment as a function of absolute improvement in disability symptoms using the WHODAS assessment. FIG. 11J shows the change in relative cerebral blood flow in the dorsomedial prefrontal cortex brain region one month after treatment as a function of absolute improvement in depression symptoms using the MADRS assessment.

Figure 12:
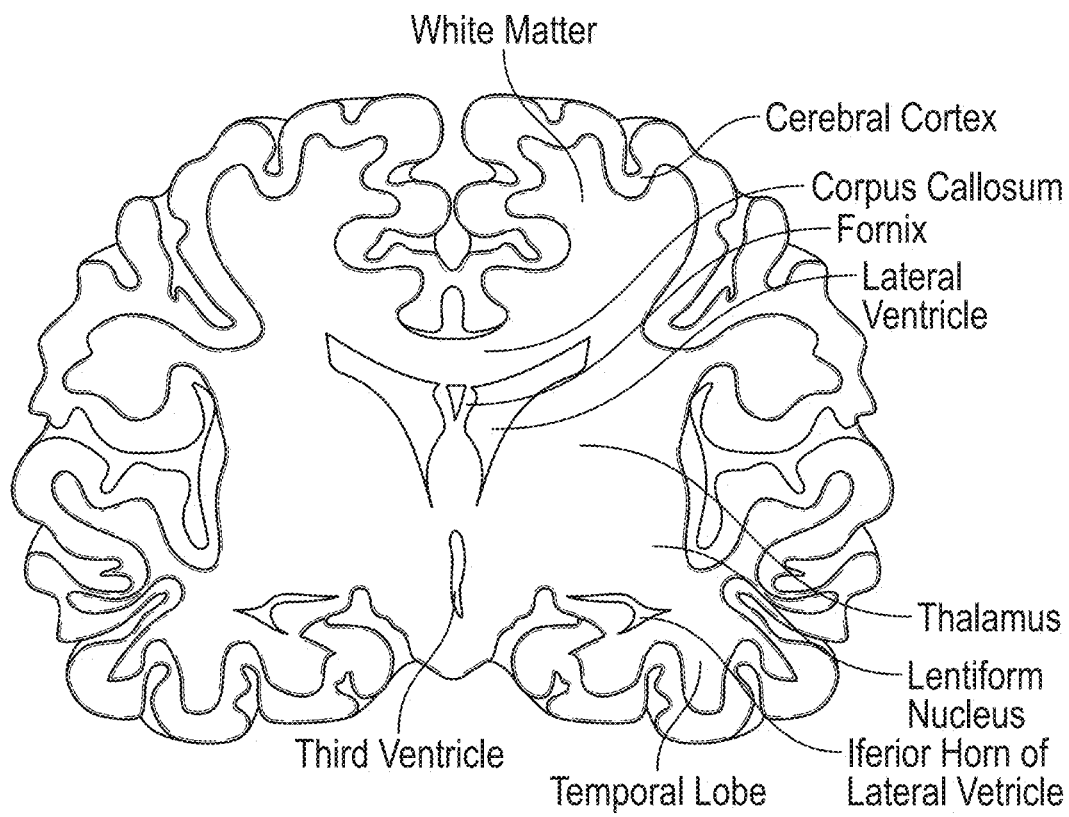
FIG. 12 is a cross-sectional diagram of the brain showing regions of interest.
Figure 13A:
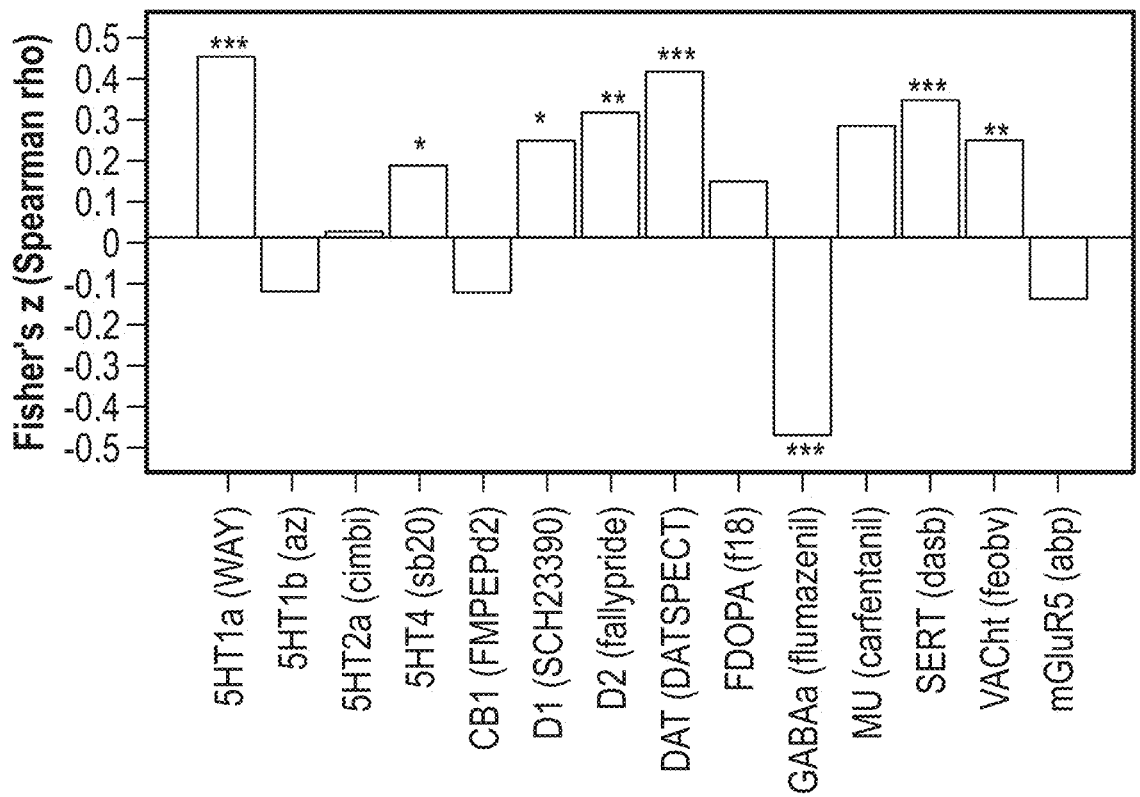
FIGS. 13A-13B are bar graphs showing the relative cerebral brain perfusion change from baseline to four days after treatment (FIG. 13A) or from baseline to one month after treatment (FIG. 13B), measured using Fisher's Z (Spearman rho), for the indicated PET map receptors abbreviated as follows: 5-HT1a (serotonin 5-hydroxytryptamine receptor subtype 1a), 5-HT1b (5-HT subtype 1b), 5-HT2a (5-HT subtype 2a), 5-HT4 (5-HT subtype 4), CB1 (cannabinoid receptor 1), D1 (dopamine D1), D2 (dopamine D2), DAT (dopamine transporter), F-DOPA (dopamine synthesis capacity), GABAa (gamma-aminobutric acid), Mu (Mu opioid receptor), SERT (serotonin transporter), vesicular acetylcholine transporter (VAChT), and mGluR5 (metabotropic glutamate receptor subtype 5).
Figure 13B:
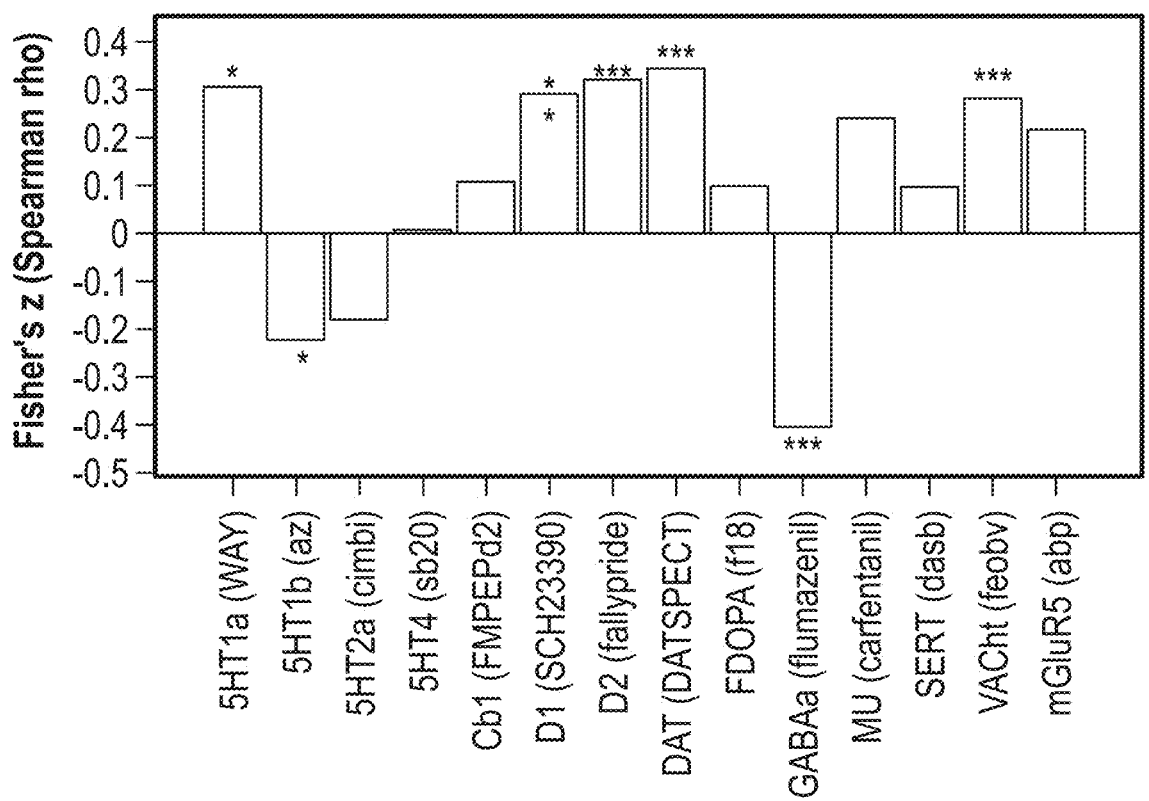

White matter lies beneath the gray matter cortex in the brain. FIG. 12 is a cross-sectional diagram of the brain showing the white matter and other regions of interest. White matter is composed of millions of bundles of axons (nerve fibers) that connect neurons in different brain regions into functional circuits. A correlation between perfusion disturbances and extent of white matter disease has been reported, where subjects with later-stage white matter lesions exhibit decreased cerebral blood flow in both white and gray matter (Bastos-Leite, et al., *Am. J. Neuroradiol*, 29 (7): 1296-1301 (2008)). The relative changes in cerebral blood perfusion from baseline to one month post treatment with ibogaine in receptors mapped with positron emission tomography (PET) was evaluated (Dukart, J. et al., *Hum. Brain Mapp.*, 42:555-556 (2021)). The receptors included 5-HT1a (serotonin 5-hydroxytryptamine receptor subtype 1a), 5-HT1b (5-HT subtype 1b), 5-HT2a (5-HT subtype 2a), 5-HT4 (5-HT subtype 4), CB1 (cannabinoid receptor 1), D1 (dopamine D1), D2 (dopamine D2), DAT (dopamine transporter), F-DOPA (dopamine synthesis capacity), GABAa (gamma-aminobutric acid), Mu receptor, SERT (serotonin trans-porter), vesicular acetylcholie transporter (VAChT), and mGluR5 (metabotropic glutamate receptor subtype 5). FIG. 13A is a bar graph showing the relative cerebral brain perfusion change from baseline to four days after treatment, using Fisher's Z (Spearman rho), for the indicated PET map receptor. Also indicated on the x-axis is the PET tracer used for the receptor map (Dukart et al. supra). FIG. 13B is a similar graph for change in relative cerebral brain perfusion from baseline to one-month after treatment.

IV. Examples

The following examples are illustrative in nature and are in no way intended to be limiting.

Example 1

Safety and Efficacy of Ibogaine Treatment in Special Operations Veterans

Thirty, male, navy seal or army special forces veterans, ages 33-58 years (mean 44.5 years), were enrolled. Of the 30 participants, 27 were Caucasian, 1 was Hispanic and 2 were Native American. Body mass index was between 17-35 kg/m$^2$. Baseline characteristics of the subjects is set forth in Table 1-1.

TABLE 1-1

Baseline characteristics of the subjects enrolled in study

| Characteristic | Number of subjects enrolled with characteristic |
|---|---|
| TBI (by history) | mTBI: 28 |
| | moderate TBI: 1 |
| | moderately severe TBI: 1 |
| TBI with loss of consciousness (LOC) (by history) | 28 |
| PTSD Lifetime (per MINI[1]) | Full diagnosis: 25 |
| | Subclinical: 4 |
| | No PTSD: 1 |
| Major depressive disorder (MDD) Lifetime (Per MINI) | Current: 15 |
| | Past: 6 |
| | No MDD: 9 |
| Substance use disorder (SUD) (per MINI) | None: 15 |
| | Alcohol use disorder: 10 |
| | Alcohol and SUD: 5 |
| History of suicidal ideation (per SCID[2], MINI) | None: 12 |
| | With suicidal ideation: 11 |
| History of suicide attempts | 7 |
| Combat exposure (score per CES[3]) | Range: 17-37 |
| | 27/30 had score 25+ |

[1]MINI = Mini International Neuropsychiatric Interview
[2]SCID = structured clinical interview for DSM Disorders
[3]CES = Combat Exposure Scale Enrolled subjects were assessed using clinical intake, diagnostic and psychological evaluations (Table 1-1), subjective reporting of symptoms, MRI, EEG and blood draw. In particular, following enrollment, participants undertook initial baseline evaluations over a secure video platform with a clinical neuropsychologist between two months and one week prior to in-person assessments, including review of medical and psychiatric history, history of combat exposures, history of TBI and blast exposure, and a psychodiagnostic interview. All participants presented with a history of TBI, according to the Ohio State University Screening for TBI exposure and the DoD TBI classification (Maas, A. I. R. et al., *Lancet Neurol.* 21, 1004-1060 (2022)). In addition, to quantify blast exposure, the Boston Assessment of TBI-Lifetime was administered (Administration, U. D. of V. A., Veterans Health. VA.gov|Veterans Affairs).

To prepare for treatment with ibogaine, a medication washout period was designed for each subject and expectation and intentions were discussed. Two to three days prior to treatment, each subject underwent neuropsychological testing, mood measures, structural and functional imaging and EEG.

With subjects in the fasting state, an intravenous infusion of 1 gram of magnesium sulfate was administered 1-2 hours prior to treatment. The oral ibogaine dosing protocol consisted of an initial test dose of 2-3 mg/kg of ibogaine hydrochloride (98+% pure). Depending on response, after about 40 minutes additional doses of ibogaine up to a total of <14 mg/kg were administered within a total 2-hour period. Approximately 12 hours after administration of ibogaine, participants were administered another intravenous infusion of 1 gram magnesium sulfate. Medical staff (MD, RN, or EMT) were onsite at a ratio of at least 1 staff per 2 patients throughout treatment for monitoring and management, but no specific coaching or psychological support was provided during treatment. For 12-16 hours following ibogaine administration, blood pressure and pulse oximetry were monitored three times a day, and QTc was monitored via continuous 5-lead ECG.

Post treatment, each subject was assessed four days after treatment, one month after treatment, and, if willing, one year after treatment. The post-treatment assessments conducted at four days and at one month after treatment included neuropsychological testing, measures of PTSD, depression, anxiety, mystical experiences, functional imaging and EEG. Post-treatment assessments conducted at one year after treatment included PTSD, depression, and anxiety measures.

Statistical analysis of the data used a p-value to ascertain the likelihood that the differences seen do not reflect a true difference, where a p-value below 5% (0.05) was considered significant. Effect size was measured using Cohen's D, and effects larger than 0.8 were considered strong. When testing for changes in multiple factors, the more the factors the more potential for erroneous inferences. A statistical method for correction of multiple tests was implemented.

World Health Organization Disability Assessment Scale 2.0 (WHODAS 2.0) was used as a measure of function. WHODAS was used to assess the impact of health conditions across six life domains (cognition, mobility, self-care, interpersonal, life activities, and community participation) and it is sensitive to change over time (Gold, L. H., *J. Am. Acad. Psychiatry Law* 42, 9 (2014). Each item in the assessment is rated on a scale ranging from no problems to extreme problems (Üstün, T. B. et al., *Measuring health and disability: Manual for WHO disability assessment schedule WHODAS* 2.0. (World Health Organization, 2010)). To capture inter-individual variability in disability the WHODAS complex scoring method was used. Raw scores were converted to a metric ranging from 0 (no disability) to 100 (full disability), by calculating the ratio of the participant's score relative to the maximum possible score in each domain as well as to the total score (Id.). A score of 20%-39% was considered mild, 40%-59% was moderate, 60%-79% was moderate-severe and 80%-100% was severe. Scores from baseline were compared to scores from one-month post treatment.

Cognitive assessments were done to determine the effect of ibogaine treatment on various cognitive domains including executive functions, memory, processing speed, attention, and working memory.

Assessments for psychological symptoms were conducted to determine the effect of treatment on clinician-rated depressive, anxious, and post-traumatic symptoms.

Imaging and EEG were performed to determine the effect of treatment on brain functional connectivity, structure, blood flow/perfusion and electrical activity.

Functional magnetic resonance imaging (fMRI) was used as a biomarker to assess whole brain connectivity, default mode and task positive network (DMN-TPN) cross-talk and connectivity with PCC as seed. Superior rostral anterior cingulate cortex (srACC) increased coupling with parahippocampal, hippocampal, amygdala, and medial temporal lobe (MTL) regions.

Neuropsychological testing of the enrolled subjects was designed to examine abilities over several domains of cognitive functioning, including estimated intelligence quotient (IQ), verbal fluency, working memory (visual and auditory), long term memory (visual and auditory), processing speed, sustained attention, problem solving, ability to perceive patterns, executive functioning, such as ability to hold and manipulate or update information in the head, inhibition, ability to organize, plan, and develop solutions to problems. In addition, assessments examining cognitive abilities over several domains of functioning were done to evaluate the safety of ibogaine use. The neuropsychological tests included WASI-II (Weschler Abbreviated Scale Intelligence) for estimated IQ (verbal comprehension and perceptual reasoning), WAIS-IV (Wechsler Adult Intelligence Scale) for working memory and processing speed (digit span, arithmetic symbol search, coding), D-KEFS (Delis-Kaplan Executive Function System) for executive functioning (trail making test, verbal fluency, color-word inhibition, tower test), HVLT (Hopkins Verbal Learning Test) and BVMT-R (Brief Visuospatial Memory Test) for learning and memory, and CPT-3 (Conner's Continuous Performance Test) for attention.

Domains of cognition included language (verbal fluency, receptive language), working memory (hold and use small amounts of temporarily stored information, time taken to compete tasks), executive functioning (cognitive switching, flexibility, multitasking), organizing, planning and finding solutions, inhibition, filtering distractions), learning and memory (ability to learn, store and retrieve auditory and visual information), attention (ability to filter distractions and remain focused).

Self-reporting measures by enrolled subjects included PTSD symptoms, mood, hopelessness, sleep, pain, function, moral injury, mystical experiences, personality (baseline only), childhood trauma (baseline only) and combat experiences (baseline only).

Clinician administered scales included CAPS-5 (Clinician-administered PTSD Scale for DSM-5), which is a gold standard assessment of PTSD symptom severity: MADRS (Montgomery-Asberg Depression Rating Scale), a measure for depressive symptom severity; and Hamilton-Anxiety Rating Scale (HAM-A) (Shear, M. K. et al., *Depress. Anxiety* 13, 166-178 (2001)) a measure for anxiety symptom severity: SCID-5 (Structured Clinical Interview for DSM-5) Overview for a historical and environmental context of symptom presentation: MINI DSM-5 (Mini International Neuropsychiatric Interview from DSM-5) for a structured psychodiagnostics assessment: BAT-L (Boston Assessment of TBI-Lifetime) for a lifetime history of TBI and blast exposure; and Ohio State University TBI Identification Method (Short Form) for a lifetime history of TBI. MADRS testing provides an indication of depressive symptoms, CAPS-5 provides an indication of PTSD and SIGH-A provides an indication of anxiety. Collectively these overlap to provide indication of mood, concentration, sleep and tension.

For the CAPS-5, the test version with a 30-item structured interview of PTSD symptoms over the past week was used, using a 0) ("Absent") to 4 ("Extreme/Incapacitating") scale, with possible total scores ranging from 0 to 80. The score range 23 to 34 is considered moderate PTSD while a higher score represents severe PTSD (Weathers, F. W. et al., *Psychol. Assess.* 30, 383-395 (2018)).

The MADRS is a clinician-administered 10-item scale assessing the severity of depression symptoms. Items are rated on a scale of 0) (no abnormality) to 6 (severe) (Montgomery, S. A. et al., *Br. J. Psychiatry J. Ment. Sci.* 134, 382-389 (1979)). A total score of 0-6 indicates no depression, 7-19 mild depression, 20-34 moderate depression, 35-59 severe depression, and 60+ very severe depressive symptoms (Müller, M. J., *J. Affect. Disord.* 77, 255-260 (2003)).

To assess anxiety symptoms, the Hamilton Anxiety Rating Scale was used. This scale includes 14-items assessing both psychic and physical symptoms of anxiety. Items are rated on a scale from 0) (no symptoms) to 4 (severe symptoms). Total score ranges were: no or minimal anxiety (≤7), mild (8-14), moderate (15-23), and severe anxiety symptoms (≥24) (Matza et al., *Int. J. Methods Psychiatr. Res.* 19, 223-232 (2010)).

Results are shown in Table 1, Table 1-2, Table 1-3, Table 1-4, Table 1-5, and Table 1-6.

TABLE 1-2

WHODAS 2.0 Subscales.

| WHODAS 2.0 Subscale | Baseline | Post-Treatment | Baseline vs Post-Treatment | | | One-Month (Mean ± SD) | Baseline vs One-Month | | |
|---|---|---|---|---|---|---|---|---|---|
| | | | $F(1, 75)$ | p(FDR) | D | | $F(1, 75)$ | p(FDR) | D |
| Cognition | 36.1% ± 14.6% | 19.2% ± 18.7% | 40.38 | <0.001 | 0.96 | 5.0% ± 7.9% | 94.84 | <0.001 | 2.38 |
| Community Participation | 35.6% ± 21.1% | 24.7% ± 22.7% | 8.24 | 0.006 | 0.53 | 5.9% ± 13.1% | 50.15 | <0.001 | 1.78 |
| Life Activities | 41.1% ± 24.8% | 31.6% ± 26.8% | 8.25 | 0.006 | 0.48 | 9.1% ± 16.2% | 57.02 | <0.001 | 1.44 |
| Interpersonal | 32.3% ± 20.4 | 21.7% ± 19.6% | 13.34 | 0.001 | 0.60 | 4.8% ± 9.5% | 63.07 | <0.001 | 1.63 |
| Self Care | 5.2% ± 9.2% | 1.9% ± 4.7% | 5.01 | 0.028 | 0.37 | 1.0% ± 2.9% | 7.21 | 0.009 | 0.51 |
| Mobility | 14.7% ± 15.7% | 7.2% ± 13.5% | 11.33 | 0.001 | 0.53 | 1.3% ± 3.3% | 22.06 | <0.001 | 0.83 |

TABLE 1-3

Sensitivity analyses including only participants meeting relevant diagnostic criteria according to the MINI at baseline. For suicidal ideation, analysis included only participants with non-zero suicidal ideation at baseline.

| | Baseline | 1-wk post | Baseline vs 1-wk. post | | | | | Baseline vs 1-mo. post | | | | |
|---|---|---|---|---|---|---|---|---|---|---|---|---|
| | | | Included N | F | df | p(FDR) | D | 1-mo. post | Included N | F | df | p(FDR) | D |
| CAPS-5 | 35.7 ± 11.0 | 4.4 ± 5.2 | 23 | 221.16 | (1, 57) | <0.001 | 2.75 | 6.0 ± 8.7 | 23 | 197.84 | (1, 57) | <0.001 | 2.98 |
| MADRS | 31.3 ± 6.5 | 3.6 ± 3.6 | 15 | 217.62 | (1, 36) | <0.001 | 4.11 | 6.4 ± 7.7 | 15 | 178.49 | (1, 36) | <0.001 | 3.15 |
| HAM-A | 23.8 ± 7.6 | 4.2 ± 3.4 | 14 | 100.36 | (1, 36) | <0.001 | 2.52 | 5.1 ± 6.3 | 14 | 100.36 | (1, 36) | <0.001 | 2.33 |

| | % Reporting | % Reporting | Included | $X^2$ | | p(FDR) | | % Reporting | Included | $X^2$ | | p(FDR) | |
|---|---|---|---|---|---|---|---|---|---|---|---|---|---|
| Suicidal Ideation (MADRS Q10)[1] | 100% | 0% | 14 | 28.00 | — | <0.001 | — | 14% | 14 | 21.00 | — | <0.001 | — |

| | % Reduction vs Baseline | | Response Rate | | Remission Rate | |
|---|---|---|---|---|---|---|
| | 1-wk. post | 1-mo. post | 1-wk. post | 1-mo. post | 1-wk. post | 1-mo. post |
| CAPS-5 | 87% ± 17% | 86% ± 19% | 96% | 100% | 83% | 83% |
| MADRS | 89% ± 11% | 81% ± 21% | 100% | 93% | 73% | 67% |
| HAM-A | 82% ± 14% | 80% ± 23% | 100% | 86% | 86% | 71% |

TABLE 1-4

Sensitivity analyses including only participants with mild TBI

| | Baseline | 1-wk. post | Included N | F | df | p(FDR) | D | 1-mo. post | Included N | F | df | p(FDR) | D |
|---|---|---|---|---|---|---|---|---|---|---|---|---|---|
| | | | | | Baseline vs 1-wk post | | | | | | Baseline vs 1-mo. post | | |
| CAPS-5 | 31.7 ± 13.0 | 3.6 ± 4.5 | 28 | 187.23 | (1, 72) | <0.001 | 2.28 | 4.8 ± 8.1 | 28 | 170.80 | (1, 72) | <0.001 | 2.49 |
| MADRS | 25.2 ± 8.7 | 2.7 ± 3.2 | 28 | 211.50 | (1, 72) | <0.001 | 2.55 | 3.6 ± 5.9 | 28 | 196.12 | (1, 72) | <0.001 | 2.70 |
| HAM-A | 20.7 ± 8.6 | 3.3 ± 3.3 | 28 | 145.63 | (1, 72) | <0.001 | 2.02 | 3.7 ± 4.6 | 28 | 144.31 | (1, 72) | <0.001 | 2.07 |

| | % Reporting SI | % Reporting SI | Included N | $X^2$ | — | p(FDR) | — | % Reporting | Included N | $X^2$ | — | p(FDR) | — |
|---|---|---|---|---|---|---|---|---|---|---|---|---|---|
| Suicidal Ideation (MADR Q10) | 46% | 0% | 28 | 16.93 | — | <0.001 | — | 7% | 28 | 11.02 | — | <0.001 | — |

| | % Reduction vs Baseline | | Response Rate | | Remission Rate | |
|---|---|---|---|---|---|---|
| | 1-wk. post | 1-mo. post | 1-wk. post | 1-mo. post | 1-wk. post | 1-mo. post |
| CAPS-5 | 89% ± 14% | 88% ± 17% | 96% | 100% | 89% | 85% |
| MADRS | 87% ± 24% | 87% ± 17% | 100% | 96% | 85% | 85% |
| HAM-A | 82% ± 19% | 82% ± 21% | 96% | 93% | 89% | 85% |

TABLE 1-5

Statistical results (t, df, and FDR-corrected p-values) associated with main effects of time point for each LME model

| | t | df | P(FDR) |
|---|---|---|---|
| All participants included | | | |
| WHODAS Total | 9.25 | 76 | <0.001 |
| WHODAS Cognition | 9.62 | 76 | <0.001 |
| WHODAS Community Participation | 6.99 | 76 | <0.001 |
| WHODAS Life Activities | 7.38 | 76 | <0.001 |
| WHODAS Interpersonal | 7.91 | 76 | <0.001 |
| WHODAS Self Care | 2.71 | 76 | 0.009 |
| WHODAS Mobility | 4.70 | 76 | <0.001 |
| CAPS-5 | 9.06 | 79 | <0.001 |
| MADRS | 9.65 | 79 | <0.001 |
| HAM-A | 9.25 | 79 | <0.001 |
| Including only participants meeting relevant diagnostic criteria | | | |
| CAPS-5 | 8.47 | 58 | <0.001 |
| MADRS | 6.93 | 37 | <0.001 |
| HAM-A | 6.07 | 40 | <0.001 |
| Including only participants with mild TBI | | | |
| CAPS-5 | 8.56 | 73 | <0.001 |
| MADRS | 9.30 | 73 | <0.001 |
| HAM-A | 8.94 | 73 | <0.001 |

TABLE 1-6

Neuropsychological tests statistical results (t, df, and FDR-corrected p-values) associated with main effects of time point for each LME model.

| Neuropsychological Construct | T | Df | P(FDR) |
|---|---|---|---|
| Detection | 4.50 | 64 | <0.001 |
| Reaction time | 3.02 | 64 | 0.008 |
| Sustained attention | 0.59 | 64 | 0.589 |
| Verbal memory | 2.52 | 76 | 0.024 |
| Visuospatial memory | 2.08 | 77 | 0.052 |
| Processing speed | 6.39 | 77 | <0.001 |
| Cognitive inhibition | 3.77 | 77 | 0.001 |
| Cognitive flexibility composite | 4.20 | 77 | <0.001 |
| Phonemic fluency | 4.70 | 77 | <0.001 |
| Working memory | 2.44 | 76 | 0.027 |
| Problem solving | 2.51 | 76 | 0.024 |
| Semantic fluency | 1.35 | 77 | 0.215 |

Example 2

Functional Imaging as a Biomarker

The subjects enrolled in the study described in Example 1 were evaluated by functional MRI at baseline, one week after treatment and one month after treatment with ibogaine and a cardioprotective agent, as described in Example 1. The subjects were asked to clear their mind of any particular thoughts in order to capture the brain at rest or in its 'default' state. An a priori region of interest was determined for analysis and 5000 functional connectivity pairs were tested. The underlying alteration in brain patterns (connectivity) due to an intervention was evaluated. The functional connectivity networks evaluated are listed in Table 2-1.

TABLE 2-1

Functional connectivity networks

| Functional Network | Description | Abbreviation |
| --- | --- | --- |
| Central executive | Executive function and goal oriented, cognitively demanding tasks, working memory, decision making | CEN |
| Dorsal attention | Goal-directed, voluntary control of visuospatial attention | DAN |
| Default mode | Self-referential processing and the so-called "stream of consciousness," introspective mental imagery, self-reflection and self-awareness | DMN |
| Limbic | Processing emotion and memory, including the hippocampus, the amygdala and the hypothalamus | LN |
| Somatomotor | Sensor motor integration | SMN |
| Salience | Modulating the switch between DMN and CEN (attention) | SN |
| Visual | Visual perception and processing | VN |

Results are shown in FIGS. 1A-1C, FIG. 2, FIGS. 3A-3B, FIGS. 4A-4C, FIG. 5 and FIG. 6.

Example 3

Cerebral Blood Flow

Arterial spin labeling (ASL) MRW was used to measure cerebral blood flow. Eighteen subjects of the subjects enrolled in the study of Example 1, all male veterans with a history of TBI, were evaluated with pseudo-continuous ASL (pcASL) at baseline, 1-2 days after treatment with ibogaine (orally administered), and one-month after treatment with ibogaine, in combination with a cardioprotective agent as described in Example 1.

A first metric of interest was change in net quantity (mL/100 g tissue/min) of blood entering different regions of the brain. Images of the left posterior orbital gyrus, left anterior insula, left and right cerebral white matter at baseline and 1-2 days post treatment (images not shown) were analyzed and compared. Images of the right anterior cingulate gyrus, right middle cingulate gyrus, right superior frontal gyrus medial segment, right posterior orbital gyrus, right cerebral white matter, right and left insula, and right planum polare at baseline and one-month post treatment (images not shown) were analyzed and compared.

A paired t-test across 3 time points—baseline (pre-treatment), 1-2 days post-treatment, and one month post-treatment—was employed. No significant changes were seen in absolute cerebral blood flow after treatment with ibogaine ($p<0.001$).

A second metric of interest was regression between change in clinical scores versus change in relative cerebral blood perfusion from baseline to one-month post treatment. Multiple regression with clinical scores at baseline and one-month post treatment was used. Images of the right anterior and middle cingulate gyrus, a component of the limbic system, were obtained (not shown). Results showing correlation of clinical scores from some of the assessments described in Example 1 with change in cerebral blood flow from baseline to one-month post treatment for certain brain regions are shown in FIGS. 11A-11J.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A method for treating a neuropsychiatric condition selected from traumatic brain injury and post-traumatic stress disorder in a subject, comprising:
   administering, or instructing to administer, to a subject a cardioprotective agent in an amount effective to achieve a physiologic effect to reduce risk of long QT syndrome and an iboga alkaloid or salt thereof, wherein the cardioprotective agent is a magnesium salt and the iboga alkaloid is ibogaine; and
   monitoring the subject by analyzing image data from a brain image to determine a predicted brain age.

2. The method of claim 1, further comprising based on said monitoring, continuing said administering or instructing to administer or recommending an alternative to said administering or instructing to administer.

3. The method of claim 1, wherein the subject has a chronological age, the method further comprising comparing the predicted brain age to the chronological age.

4. The method of claim 3, further comprising repeating said administering or instructing to administer if the predicted brain age is greater than the chronological age.

5. The method of claim 4, further comprising repeating said monitoring to determine a post-treatment predicted brain age, and comparing said post-treatment predicted brain age to the chronological age.

6. The method of claim 5, further comprising repeating said administering or instructing to administer if the post-treatment predicted brain age is greater than the chronological age.

7. The method of claim 5, further comprising repeating said administering or instructing to administer if the post-treatment predicted brain age is equal to or less than the precited brain age.

8. The method of claim 5, further comprising recommending an alternative to said administering or instructing to administer if the post-treatment predicted brain age is equal to or greater than the predicted brain age.

9. A method for treating a neuropsychiatric condition selected from traumatic brain injury and post-traumatic stress disorder in a subject, comprising:
   analyzing a first image data of a subject's brain using a brain age model to determine a first estimated brain age of the brain, where the first image data is captured prior to administration of an iboga alkaloid or salt thereof;

administering, or instructing to administer, to the subject a cardioprotective agent in an amount effective to achieve a physiologic effect to reduce risk of long QT syndrome and the iboga alkaloid or salt thereof;

analyzing a second image data of the subject's brain using the brain age model to determine a second estimated brain age of the brain, where the second image data is captured after administration of the iboga alkaloid or salt thereof; and verifying treatment efficacy when the first estimated brain age is greater than the second estimated brain age, wherein the iboga alkaloid is ibogaine and the cardioprotective agent is a magnesium salt.

10. The method of claim 9, wherein verifying treatment efficacy comprises verifying a correct dosage amount.

11. The method of claim 9, further comprising administering, or instructing to administer, to the subject an additional dose of the cardioprotective agent in an amount effective to achieve a physiologic effect to reduce risk of long QT syndrome and the iboga alkaloid or salt thereof.

12. The method of claim 1, wherein the neuropsychiatric condition is traumatic brain injury.

13. The method of claim 1, wherein the neuropsychiatric condition is post-traumatic stress disorder.

* * * * *